US007202029B2

(12) United States Patent
Busfield

(10) Patent No.: US 7,202,029 B2
(45) Date of Patent: Apr. 10, 2007

(54) NUCLEIC ACIDS ENCODING HUMAN TANGO 195

(75) Inventor: Samantha J. Busfield, Maddington (AU)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 345 days.

(21) Appl. No.: 10/254,426

(22) Filed: Sep. 25, 2002

(65) Prior Publication Data

US 2003/0113865 A1      Jun. 19, 2003

Related U.S. Application Data

(63) Continuation of application No. 09/731,449, filed on Dec. 7, 2000, now abandoned, which is a continuation-in-part of application No. 09/410,359, filed on Sep. 30, 1999, now abandoned, which is a continuation-in-part of application No. 09/163,523, filed on Sep. 30, 1998, now abandoned.

(51) Int. Cl.
    *G01N 33/53*     (2006.01)
    *C12N 5/10*     (2006.01)
    *C12N 15/19*     (2006.01)
    *C12N 15/63*     (2006.01)

(52) U.S. Cl. .................. 435/6; 536/23.5; 435/69.5; 435/325; 435/252.3; 435/254.11; 435/320.1

(58) Field of Classification Search ..................... None
See application file for complete search history.

(56) References Cited

U.S. PATENT DOCUMENTS 6,326,472 B1    12/2001    Timans et al.
6,620,912 B2 *    9/2003    Young et al. ............... 530/350

FOREIGN PATENT DOCUMENTS

| WO | WO 99/19480 | 4/1999 |
|---|---|---|
| WO | WO 99/37772 | 7/1999 |
| WO | WO 99/37773 | 7/1999 |
| WO | WO 99/41084 | 8/1999 |

OTHER PUBLICATIONS

Murdoch et al. 2000, Blood, 95:3032-3043.*
Ji et al. 1998, J. Biol. Chem. 273:17299-17302.*
Skolnick et al. Nature Biotechnology. Mar. 2000, vol. 18, pp. 283-287.*
Reiger et al. (1996) Glossary of Genetics and Cytogenetics, 4th edition. Springer-verlag, pp. 16-19.*
Mikayama et al. Proc. Natl. Acad. Sci. USA vol. 90, pp. 10056-10060, 1993.*
Voet et al. Biochemistry. John Wiley & Sons, Inc., pp. 126-128 and 228-234, 1990.*
Doerks, T., et al., "Protein Annotation: Detective Work for Function Prediction," *Trends in Genetics*, 14(6):248-250 (1998).
Dong, et al. "B7-H1, a Third Member of the B7 Family, Co-stimulates T-cell Proliferation and Interleukin-10 Secretion," *Nature Medicine* (5): 1356-1369 (1999).
Holst, et al. "Steric Hindrance Mutagenesis versus Alanine Scan in Mapping of Ligand Binding Sites in the Tachykinin $NK_1$ Receptor," *Molecular Pharmacology* 53:166-175 (1998).
Aversa et al., *Engagement of the signaling lymphocytic activation molecule (SLAM) on acativated T cells . . .* , J. of Immunol. 158(9):4036-4044, 1997.
Aversa et al., *SLAM and its role in T cell activation and Th cell responses*, Immunol. And Cell Biol., 75:202-205, 1997.
Carballido et al., *Reversal of human allergic T helper 2 responses by engagement of signaling lymphocytic activation molecule*, J. of Immunol., 159(9):4316-4321. 1997.
Cocks et.al., *A novel receptor involved in T-cell activation*, Nature, 376:260-263, 1995.
Cunningham et al., "High-Resolution Epitope Mapping of hGH-Receptor Interactions by Alanine-Scanning Mutagenesis" Science 244:1081, 1989.
Ferrante et al., *Cytokine Production and Surface Marker Expression in Acute and Stable Multiple Sclerosis: Altered IL-12 Production and Augmented Signaling Lymphocytic Activation Molecule (SLAM)-Expressing Lymphocytes in Acute Multiple Sclerorsis*, The Journal of Immunology, vol. 160, No. 3, pp. 1514-1521, 1998.
George et al., *Current Methods in Sequence Comparison and Analysis*, Macromolecular Sequencing and Synthesis: Selected Methods and Applications, pp. 127-149, 1988.
GenBank Accession No. G22227, Hudson, T., May 31, 1996.
GenBank Accession No. U33017, Cocks et al., Sep. 14, 1995.
Isomaki et al., *Increased expression of signaling lymphocytic activation molecule in patients with Rheumatoid Arthritis in its role . . .* , J. of Immunol., 159(5):2986-2993, 1997.
Punnonen et al., *Soluble and Membrane-bound Forms of Signaling Lymphocytic Activation Molecule (SLAM) Induce Proliferation and Ig Synthesis by Activated Human B Lymphocytes*, J. Exp. Med., vol. 185, No. 6, pp. 993-1004, 1997.
Rieger et al., *Glossary of Genetics and Cytogenetics: Classical and Molecular*, Fourth Ed., Spinger-Verlag, New York, 1976.

\* cited by examiner

*Primary Examiner*—Prema Mertz
(74) *Attorney, Agent, or Firm*—Hamilton, Brook, Smith & Reynolds, P.C.

(57) ABSTRACT

The invention concerns cDNA molecules encoding TANGO 191 and TANGO 195, both of which are transmembrane proteins.

The nucleic acids and polypeptides of the present invention are useful as modulating agents in regulating a variety of cellular processes. Accordingly, in one aspect, this invention provides isolated nucleic acid molecules encoding a polypeptide of the invention or biologically active portion thereof. The present invention also provides nucleic acid molecules which are suitable as primers or hybridization probes for the detection of nucleic acids encoding a polypeptide of the invention.

13 Claims, 13 Drawing Sheets

```
   1 GTCGACCCACGCGTCCGCAGAGAAGAGTTTGAGATGCTTCTTCTTCAGAGCACTTCCTAC
  61 TGAAAGAGGTATCTCTCTGGATAGGAAGAAATATAGTAGAACCCTTTGAAAATGGATATT
 121 TTCACATATTTTCGTTCAGATACAAAAGCTGGCAGTTACTGAAATAAGGACTTGAAGTTC
 181 CTTCCTCTTTTTTTTATGTCTTAAGAGCAGGAAATAAAGAGACAGCTGAAGGTGTAGCCT
 241 TGACCAACTGAAAGGGAAATCTTCATCCTCTGAAAAAACATATGTGATTCTCAAAAAACG
 301 CATCTGGAAAATTGATAAAGAAGCGATTCTGTAGATTCTCCCAGCGCTGTTGGGCTCTCA
 361 ATTCCTTCTGTGAAGGACAACATATGGTGATGGGGAAATCAGAAGCTTTGAGACCCTCTA
 421 CACCTGGATATGAATCCCCCTTCTAATACTTACCAGAAATGAAGGGGATACTCAGGGCAG
 481 AGTTCTGAATCTCAAAACACTCTACTCTGGCAAAGGAATGAAGTTATTGGAGTGATGACA
 541 GGAACACGGGAGAACAATGCTCTGTTTGGGCTGGATATTTCTTTGGCTTGTTGCAGGAGA
   1                 M  L  C  L  G  W  I  F  L  W  L  V  A  G  E

601 GCGAATTAAAGGATTTAATATTTCAGGTTGTTCCACAAAAAAACTCCTTTGGACATATTC
  16  R  I  K  G  F  N  I  S  G  C  S  T  K  K  L  L  W  T  Y  S

661 TACAAGGAGTGAAGAGGAATTTGTCTTATTTTGTGATTTACCAGAGCCACAGAAATCACA
  36  T  R  S  E  E  E  F  V  L  F  C  D  L  P  E  P  Q  K  S  H

721 TTTCTGCCACAGAAATCGACTCTCACCAAAACAAGTCCCTGAGCACCTGCCCTTCATGGG
  56  F  C  H  R  N  R  L  S  P  K  Q  V  P  E  H  L  P  F  M  G

781 TAGTAACGACCTATCTGATGTCCAATGGTACCAACAACCTTCGAATGGAGATCCATTAGA
  76  S  N  D  L  S  D  V  Q  W  Y  Q  Q  P  S  N  G  D  P  L  E

841 GGACATTAGGAAAAGCTATCCTCACATCATTCAGGACAAATGTACCCTTCACTTTTTGAC
  96  D  I  R  K  S  Y  P  H  I  I  Q  D  K  C  T  L  H  F  L  T

901 CCCAGGGGTGAATAATTCTGGGTCATATATTTGTAGACCCAAGATGATTAAGAGCCCCTA
 116  P  G  V  N  N  S  G  S  Y  I  C  R  P  K  M  I  K  S  P  Y

961 TGATGTAGCCTGTTGTGTCAAGATGATTTTAGAAGTTAAGCCCCAGACAAATGCATCCTG
 136  D  V  A  C  C  V  K  M  I  L  E  V  K  P  Q  T  N  A  S  C

1021 TGAGTATTCCGCATCACATAAGCAAGACCTACTTCTTGGGAGCACTGGCTCTATTTCTTG
 156  E  Y  S  A  S  H  K  Q  D  L  L  L  G  S  T  G  S  I  S  C

1081 CCCCAGTCTCAGCTGCCAAAGTGATGCACAAAGTCCAGCGGTAACCTGGTACAAGAATGG
 176  P  S  L  S  C  Q  S  D  A  Q  S  P  A  V  T  W  Y  K  N  G

1141 AAAACTCCTCTCTGTGGAAAGGAGCAACCGAATCGTAGTGGATGAAGTTTATGACTATCA
 196  K  L  L  S  V  E  R  S  N  R  I  V  V  D  E  V  Y  D  Y  H

1201 CCAGGGCACATATGTATGTGATTACACTCAGTCGGATACTGTGAGTTCGTGGACAGTCAG
 216  Q  G  T  Y  V  C  D  Y  T  Q  S  D  T  V  S  S  W  T  V  R

1261 AGCTGTTGTTCAAGTGAGAACCATTGTGGGAGACACTAAACTCAAACCAGATATTCTGGA
 236  A  V  V  Q  V  R  T  I  V  G  D  T  K  L  K  P  D  I  L  D

1321 TCCTGTCGAGGACACACTGGAAGTAGAACTTGGAAAGCCTTTAACTATTAGCTGCAAAGC
 256  P  V  E  D  T  L  E  V  E  L  G  K  P  L  T  I  S  C  K  A

1381 ACGATTTGGCTTTGAAAGGGTCTTTAACCCTGTCATAAAATGGTACATCAAAGATTCTGA
 276  R  F  G  F  E  R  V  F  N  P  V  I  K  W  Y  I  K  D  S  D
```

FIG. 1A

```
1441  CCTAGAGTGGGAAGTCTCAGTACCTGAGGCGAAAAGTATTAAATCCACTTTAAAGGATGA
 296    L   E   W   E   V   S   V   P   E   A   K   S   I   K   S   T   L   K   D   E

1501  AATCATTGAGCGTAATATCATCTTGGAAAAAGTCACTCAGCGTGATCTTCGCAGGAAGTT
 316    I   I   E   R   N   I   I   L   E   K   V   T   Q   R   D   L   R   R   K   F

1561  TGTTTGCTTTGTCCAGAACTCCATTGGAAACACAACCCAGTCCGTCCAACTGAAAGAAAA
 336    V   C   F   V   Q   N   S   I   G   N   T   T   Q   S   V   Q   L   K   E   K

1621  GAGAGGAGTGGTGCTCCTGTACATCCTGCTTGGCACCATCGGGACCCTGGTGGCCGTGCT
 356    R   G   V   V   L   L   Y   I   L   L   G   T   I   G   T   L   V   A   V   L

1681  GGCGGCGAGTGCCCTCCTCTACAGGCACTGGATTGAAATAGTGCTGCTGTACCGGACCTA
 376    A   A   S   A   L   L   Y   R   H   W   I   E   I   V   L   L   Y   R   T   Y

1741  CCAGAGCAAGGATCAGACGCTTGGGGATAAAAAGGATTTTGATGCTTTCGTATCCTATGC
 396    Q   S   K   D   Q   T   L   G   D   K   K   D   F   D   A   F   V   S   Y   A

1801  AAAATGGAGCTCTTTTTCCAAGTGAGGCCACTTCATCTCTGAGTGAAGAACACTTGGCCCT
 416    K   W   S   S   F   P   S   E   A   T   S   S   L   S   E   E   H   L   A   L

1861  GAGCCTATTTCCTGATGTTTTAGAAAACAAATATGGATATAGCCTGTGTTTGCTTGAAAG
 436    S   L   F   P   D   V   L   E   N   K   Y   G   Y   S   L   C   L   L   E   R

1921  AGATGTGGCTCCAGGAGGAGTGTATGCAGAAGACATTGTGAGCATTATTAAGAGAAGCAG
 456    D   V   A   P   G   G   V   Y   A   E   D   I   V   S   I   I   K   R   S   R

1981  AAGAGGAATATTTATCTTGAGCCCCAACTATGTCAATGGACCCAGTATCTTTGAACTACA
 476    R   G   I   F   I   L   S   P   N   Y   V   N   G   P   S   I   F   E   L   Q

2041  AGCAGCAGTGAATCTTGCCTTGGATGATCAAACACTGAAACTCATTTTAATTAAGTTCTG
 496    A   A   V   N   L   A   L   D   D   Q   T   L   K   L   I   L   I   K   F   C

2101  TTACTTCCAAGAGCCAGAGTCTCTACCTCATCTCGTGAAAAAAGCTCTCAGGGTTTTGCC
 516    Y   F   Q   E   P   E   S   L   P   H   L   V   K   K   A   L   R   V   L   P

2161  CACAGTTACTTGGAGAGGCTTAAAATCAGTTCCTCCCAATTCTAGGTTCTGGGCCAAAAT
 536    T   V   T   W   R   G   L   K   S   V   P   P   N   S   R   F   W   A   K   M

2221  GCGCTACCACATGCCTGTGAAAAACTCTCAGGGATTCACGTGGAACCAGCTCAGAATTAC
 556    R   Y   H   M   P   V   K   N   S   Q   G   F   T   W   N   Q   L   R   I   T

2281  CTCTAGGATTTTTCAGTGGAAAGGACTCAGTAGAACAGAAACCACTGGGAGGAGCTCCCA
 576    S   R   I   F   Q   W   K   G   L   S   R   T   E   T   T   G   R   S   S   Q

2341  GCCTAAGGAATGGTGAAATGAGCCCTGGAGCCCCCTCCAGTCCAGTCCCTGGGATAGAGA
 596    P   K   E   W   *

2401  TGTTGCTGGACAGAACTCACAGCTCTGTGTGTGTGTTCAGGCTGATAGGAAATTCAAA
2461  GAGTCTCCTGCCAGCACCAAGCAAGCTTGATGGACAATGGAGTGGGATTGAGACTGTGGT
2521  TTAGAGCCTTTGATTTCCTGGACTGGACTGACGGCGAGTGAATTCTCTAGACCTTGGGTA
2581  CTTTCAGTACACAACACCCCTAAGATTTCCCAGTGGTCCGAGCAGAATCAGAAAATACAG
2641  CTACTTCTGCCTTATGGCTAGGGAACTGTCATGTCTACCATGTATTGTACATATGACTTT
2701  ATGTATACTTGCAATCAAATAAATATTATTTTATTAGAAAAAAAAAAAAAAAAA
```

FIG. 1B

```
   1  GCGTCCGATGTTTTCACTTTTGGGACATCCTGTTCTGAGTCAAGATTCCTCCTTCTGAA
  61  CATGGGACTTTCCAGAAGGACCACAGCTCCTCCCGTGCATCCACTCGGCCTGGGAGGTTC
 121  TGGATTTTGGCTGTCGAGGGAGTTTGCCTGCCTCTCCAGAGAAAGATGGTCATGAGGCCC
   1                                                    M  V  M  R  P

181  CTGTGGAGTCTGCTTCTCTGGGAAGCCCTACTTCCCATTACAGTTACTGGTGCCCAAGTG
   6   L  W  S  L  L  L  W  E  A  L  L  P  I  T  V  T  G  A  Q  V

241  CTGAGCAAAGTCGGGGGCTCGGTGCTGCTGGTGGCAGCGCGTCCCCCTGGCTTCCAAGTC
  26   L  S  K  V  G  G  S  V  L  L  V  A  A  R  P  P  G  F  Q  V

301  CGTGAGGCTATCTGGCGATCTCTCTGGCCTTCAGAAGAGCTCCTGGCCACGTTTTTCCGA
  46   R  E  A  I  W  R  S  L  W  P  S  E  E  L  L  A  T  F  F  R

361  GGCTCCCTGGAGACTCTGTACCATTCCCGCTTCCTGGGCCGAGCCCAGCTACACAGCAAC
  66   G  S  L  E  T  L  Y  H  S  R  F  L  G  R  A  Q  L  H  S  N

421  TTCAGCCTGGAGCTCGGGCCGCTGGAGTCTGGAGACAGCGGCAACTTCTCCGTGTTGATG
  86   L  S  L  E  L  G  P  L  E  S  G  D  S  G  N  F  S  V  L  M

481  GTGGACACAAGGGGCCAGCCCTGGACCCAGACCCTCCAGCTCAAGGTGTACGATGCAGTG
 106   V  D  T  R  G  Q  P  W  T  Q  T  L  Q  L  K  V  Y  D  A  V

541  CCCAGGCCCGTGGTACAAGTGTTCATTGCTGTAGAAAGGGATGCTCAGCCCTCCAAGACC
 126   P  R  P  V  V  Q  V  F  I  A  V  E  R  D  A  Q  P  S  K  T

601  TGCCAGGTTTTCTTGTCCTGTTGGGCCCCCAACATCAGCGAAATAACCTATAGCTGGCGA
 146   C  Q  V  F  L  S  C  W  A  P  N  I  S  E  I  T  Y  S  W  R

661  CGGGAGACAACCATGGACTTTGGTATGGAACCACACAGCCTCTTCACAGACGGACAGGTG
 166   R  E  T  T  M  D  F  G  M  E  P  H  S  L  F  T  D  G  Q  V

721  CTGAGCATTTCCCTGGGACCAGGAGACAGAGATGTGGCCTATTCCTGCATTGTCTCCAAC
 186   L  S  I  S  L  G  P  G  D  R  D  V  A  Y  S  C  I  V  S  N

781  CCTGTCAGCTGGGACTTGGCCACAGTCACGCCCTGGGATAGCTGTCATCATGAGGCAGCA
 206   P  V  S  W  D  L  A  T  V  T  P  W  D  S  C  H  H  E  A  A

841  CCAGGGAAGGCCTCCTACAAAGATGTGCTGCTGGTGGTGGTGCCTGTCTCGCTGCTCCTG
 226   P  G  K  A  S  Y  K  D  V  L  L  V  V  V  P  V  S  L  L  L

901  ATGCTGGTTACTCTCTTCTCTGCCTGGCACTGGTGCCCCTGCTCAGGGCCCCACCTCAGA
 246   M  L  V  T  L  F  S  A  W  H  W  C  P  C  S  G  P  H  L  R

961  TCAAAGCAGCTCTGGATGAGATGGGACCTGCAGCTCTCCCTCCCCAAGGTGACTCTTAGC
 266   S  K  Q  L  W  M  R  W  D  L  Q  L  S  L  P  K  V  T  L  S

1021  AACCTCATTTCGACAGTGGTTTGTAGCGTGGTGCACCAGGGCCTTGTTGAACAGATCCAC
 286   N  L  I  S  T  V  V  C  S  V  V  H  Q  G  L  V  E  Q  I  H

1081  ACGTGCTCTAATAAAGTTCCCA
 306   T  C  S  N  K  V  P
```

FIG. 3

```
                      10         20         30         40
TANGO 195 MVMRPLWSL----LLWEALLPITVTGAQ------VLSKVGGSVLLV-------AARPPGP
          :  . :  ::     .:  :. .    ::..      .: ...:. :::      .   ..
    SLAM  MDPKGLLSLTFVLFLSLAFGASYGTGGRMMNCPKILRQLGSKVLLPLTYERINKSMNKSI
               10         20         30         40         50         60

50         60         70         80         90        100
          QVREAIWRSLWPSEELLATFFRGSLETLYHSRFLG-RAQLHSNLSLELGPLESGDSGNFS
          ..   .. .:: :  : :   ..  : .   .:.::  :  ..  .: :: .::    ..
          HIVVTMAKSLENSVENKIVSLDPSEAG--PPRYLGDRYKFYLE-NLTLGIRESRKEDEGW
               70         80         90        100        110

110        120        130        140        150        160
          VLMVDTRGQPWTQT--LQLKVYDAVPRPVVQVFIAVERDAQPSKTCQVFLSCWAPNISEI
          ::.   ..  .. .:  :::...: :. :  ...:     .: . :: ...:.:  . .
          YLMTLEKNVS-VQRFCLQLRLYEQVSTPEIKVL----NKTQENGTCTLILGCTVEKGDHV
               120        130        140        150        160        170

170        180        190        200        210        220
          TYSWRRETTMDFGMEPHSLFTDGQVLSISLGPGDRDVAYSCIVSNPVSWDLATVTPWDSC
          .:::   :  .    :   :  .    .....:.:..:: . :   : :..:::::.:  .   :  .:: .:
          AYSWS-EKA---GTHPLNPANSSHLLSLTLGPQHADNIYICTVSNPISNNSQTFSPWPGC
               180        190        200        210        220

230        240        250        260        270
          HHEAAPGKASYKDVLLVVVPVSLLLMLVTL-FSAWHWCPCSGPHLRSKQLWMRWDLQLSL
          . ...   :.    . :.    . .:.:.:..  .             . : .   ...  .
          RTDPSETKPWAVYAGLLGGVIMILIMVVILQLRRRGKTNHYQTTVEKKSLTIYAQVQKPG
               230        240        250        260        270        280

280        290        300        310
          P-KVTLSNLISTVVCSVVHQGLVEQIHTC---SNKVPX---------
          :  . :.... .   :.... . .:..     .: . .
          PLQKKLDSFPAQDPCTTIYVAATEPVPESVQETNSITVYASVTLPES
               290        300        310        320        330
```

FIG. 5

```
Score: 7.10    Seq: 71 128    Model: 6 47
             *r.rYmVsthPpdYtIwwY...rNaqpi............tLtInsWq

TANGO 191  71  LPFMGSNDLSDVQ--WYQQPSNGDPLEDIRKSYPHIIQDKCTLHFLTPG  117 yEDsGtYwCmV*

118  VNNSGSYICRP  128

Score: 12.19   Seq: 168 223   Model: 1 47
             *GqsVTLTCmVs..fhPpdYt.IwwYrNaqpi......tLtInsWqvEDs

TANGO 191  168 GSTGSISCPSLSCQSDAQSPAVTWYKNGKLLSVERSNRIVVDEVYDYHQ  216

GtYwCmV*

217  GTYVCDY  223

Score: 4.61    Seq: 266 339   Model: 1 47
             *GqsVTLTCmVs..fhPpdYt.IwwYrNaqpi.............

TANGO 191  266 GKPLTISCKARFGFERVFNPVIKWYIKDSDLEWEVSVPEAKSIKSTLKD  314

....tLtInsWqvEDs.GtYwCmV*

315  EIIERNIILEKVTQRDLRRKFVCFV  339
```

FIG. 6

```
                                                          M   W   S   L   W   S   L   L   L     9
CCCACGCGTCCGCCCACGCGTCCGCAAGGGAGGACAACGGCC ATG TGG TCC CTC TGG AGT CTT CTT CTC             69

F   E   A   L   L   P   V   V   V   V   S   V   Q   V   L   S   K   V   G   D    29
TTT GAA GCT CTC CTT CCC GTT GTG GTT GTC AGT GTC CAA GTG CTA AGC AAG GTA GGG GAC    129

S   E   L   L   V   A   E   C   P   P   G   F   Q   V   R   E   A   I   W   R    49
TCA GAG CTG CTG GTG GCC GAG TGT CCT CCG GGC TTC CAA GTG CGT GAG GCT ATC TGG CGA    189

S   L   W   P   S   E   E   L   L   A   T   F   F   R   G   S   L   E   T   L    69
TCT CTG TGG CCA TCG GAG GAG CTC CTG GCC ACA TTT TTC CGA GGT TCC TTG GAG ACT CTG    249

Y   H   S   R   F   L   G   R   V   Q   L   Y   D   N   L   S   L   E   L   G    89
TAC CAC TCT CGT TTC CTG GGC CGA GTC CAG CTA TAT GAC AAC CTC AGC CTG GAG CTT GGA    309

P   L   K   P   G   D   S   G   N   F   S   V   L   M   V   D   T   R   G   Q   109
CCC CTG AAA CCT GGA GAC AGC GGC AAT TTC TCT GTG CTG ATG GTG GAT ACA AGG GGT CAA    369

T   W   T   Q   T   L   Y   L   K   V   Y   D   A   V   P   K   P   E   V   Q   129
ACC TGG ACC CAG ACC CTG TAT CTC AAG GTG TAC GAT GCA GTA CCC AAG CCC GAG GTT CAA    429

V   F   T   A   A   A   E   E   T   Q   P   L   N   T   C   Q   V   F   L   S   149
GTG TTC ACT GCT GCA GCA GAG GAG ACC CAA CCC CTC AAT ACC TGT CAG GTC TTC TTG TCC    489

C   W   A   P   N   I   S   D   I   T   Y   S   W   R   R   E   G   T   V   D   169
TGC TGG GCC CCC AAC ATC AGT GAC ATA ACC TAC AGC TGG CGA CGG GAG GGG ACA GTG GAC    549

F   N   G   E   V   H   S   H   F   S   N   G   Q   V   L   S   V   S   L   G   189
TTC AAT GGT GAA GTG CAC AGC CAT TTC TCA AAT GGA CAG GTG TTA AGT GTC TCA CTG GGA    609

L   G   D   K   D   V   A   F   T   C   I   A   S   N   P   V   S   W   D   M   209
CTG GGG GAC AAG GAT GTG GCC TTT ACC TGC ATT GCC TCC AAT CCT GTC AGC TGG GAT ATG    669

T   T   V   T   P   W   E   S   C   H   H   E   A   A   S   G   K   A   S   Y   229
ACC ACA GTC ACC CCC TGG GAG AGC TGC CAT CAC GAG GCA GCC TCC GGG AAG GCC TCC TAC    729

K   D   V   L   L   V   V   V   P   I   T   L   F   L   I   L   A   G   L   F   249
AAG GAC GTG CTA CTG GTA GTA GTG CCA ATT ACA CTG TTC CTG ATC CTG GCT GGT CTC TTT    789

G   A   W   H   H   G   L   C   S   G   K   K   K   D   A   C   T   D   G   V   269
GGG GCA TGG CAC CAT GGC CTC TGC TCA GGG AAG AAG AAG GAT GCT TGC ACT GAC GGG GTG    849

L   P   E   T   E   N   A   L   V   *                                             279
CTT CCA GAG ACA GAG AAT GCC CTC GTA TAG                                            879

AGGATGTCATGAGGGACAACATAAACTGGTGCTTGGACCATGATGAGATGCCCTGCTCAGCCACGTGATGCTCCACACC     958

TGGACACCTCCAGGATCCTCATAACTGCCACAAGTCGGCCTGCCTCTAGCGGACAGCCAAGAAAACCACCATCCTGGAA    1037

CGTCACCCTGGCCCAAACTTCCTCCTTCCTCCATCCTGTTCGCACATGCCGGATCCTCTCTGGGCAAGGTGAACTAGTA    1116
```

FIG. 7A

```
GGATGCTTCCTTCAGAACACAGGACTTTCTCTAGGATCCACAGAGACATTGATTATCCAAGGCATCCATTCTTCTATCA  1195
CTGTACATAAGGTCTTGCCCAACAGCCACCAAGGGACGGCCTCCAGGCCAGGACCTTGGCTCAAAGAGAGATGAGATGT  1274
TTGAACTAACATGGAAATTGAGCTAACCATTGCCAACTCCAGCCCCTGGGGTCTGAGTTCCTGTGTTCAAGA         1353
TGTTATTATAAGAAAAGGCAAAGAACAGGAAATGATGAGGGTGGGCATTCTCTTTCTGGTCTGAAGGACTTTAAGAT    1432
TATCTGAGTTCAAGGCCATCAAAGTAAATTGAGATTACAGATGATGAGGGGTTGGTAGCTAATGTGCCATGTTGGGA    1511
TCAAAGCCATTTTTCTGGTAGCACTATATTAATAGACACCTTTGTTGCCATTAAAAAAAAAAAAAAAAAAAAAAAAA    1590
AAAAAAAAAAAAA                                                                    1603
```

FIG. 7B

```
GATGTTTTCACTTTTGGGACATCCTGTTCTGAGTCAAGATTCCTCCTTCTGAACATGGGACTTTCCAGAAGGACCACAG   79

CTCCTCCCGTGCATCCACTCGGCCTGGGAGGTTCTGGATTTTGGCTGTCGAGGGAGTTTGCCTGCCTCTCCAGAGAAAG  158

M   V   M   R   P   L   W   S   L   L   L   W   E   A   L   L   P   I   T   V    20
    ATG GTC ATG AGG CCC CTG TGG AGT CTG CTT CTC TGG GAA GCC CTA CTT CCC ATT ACA GTT   218

T   G   A   Q   V   L   S   K   V   G   G   S   V   L   L   V   A   A   R   P    40
    ACT GGT GCC CAA GTG CTG AGC AAA GTC GGG GGC TCG GTG CTG CTG GTG GCA GCG CGT CCC   278

P   G   F   Q   V   R   E   A   I   W   R   S   L   W   P   S   E   E   L   L    60
    CCT GGC TTC CAA GTC CGT GAG GCT ATC TGG CGA TCT CTC TGG CCT TCA GAA GAG CTC CTG   338

A   T   F   F   R   G   S   L   E   T   L   Y   H   S   R   F   L   G   R   A    80
    GCC ACG TTT TTC CGA GGC TCC CTG GAG ACT CTG TAC CAT TCC CGC TTC CTG GGC CGA GCC   398

Q   L   H   S   N   L   S   L   E   L   G   P   L   E   S   G   D   S   G   N   100
    CAG CTA CAC AGC AAC CTC AGC CTG GAG CTC GGG CCG CTG GAG TCT GGA GAC AGC GGC AAC   458

F   S   V   L   M   V   D   T   R   G   Q   P   W   T   Q   T   L   Q   L   K   120
    TTC TCC GTG TTG ATG GTG GAC ACA AGG GGC CAG CCC TGG ACC CAG ACC CTC CAG CTC AAG   518

V   Y   D   A   V   P   R   P   V   V   Q   V   F   I   A   V   E   R   D   A   140
    GTG TAC GAT GCA GTG CCC AGG CCC GTG GTA CAA GTG TTC ATT GCT GTA GAA AGG GAT GCT   578

Q   P   S   K   T   C   Q   V   F   L   S   C   W   A   P   N   I   S   E   I   160
    CAG CCC TCC AAG ACC TGC CAG GTT TTC TTG TCC TGT TGG GCC CCC AAC ATC AGC GAA ATA   638

T   Y   S   W   R   R   E   T   T   M   D   F   G   M   E   P   H   S   L   F   180
    ACC TAT AGC TGG CGA CGG GAG ACA ACC ATG GAC TTT GGT ATG GAA CCA CAC AGC CTC TTC   698

T   D   G   Q   V   L   S   I   S   L   G   P   G   D   R   D   V   A   Y   S   200
    ACA GAC GGA CAG GTG CTG AGC ATT TCC CTG GGA CCA GGA GAC AGA GAT GTG GCC TAT TCC   758

C   I   V   S   N   P   V   S   W   D   L   A   T   V   T   P   W   D   S   C   220
    TGC ATT GTC TCC AAC CCT GTC AGC TGG GAC TTG GCC ACA GTC ACG CCC TGG GAT AGC TGT   818

H   H   E   A   A   P   G   K   A   S   Y   K   D   V   L   L   V   V   V   P   240
    CAT CAT GAG GCA GCA CCA GGG AAG GCC TCC TAC AAA GAT GTG CTG CTG GTG GTG GTG CCT   878

V   S   L   L   L   M   L   V   T   L   F   S   A   W   H   W   C   P   C   S   260
    GTC TCG CTG CTC CTG ATG CTG GTT ACT CTC TTC TCT GCC TGG CAC TGG TGC CCC TGC TCA   938

G   P   H   L   R   S   K   Q   L   W   M   R   W   D   L   Q   L   S   L   H   280
    GGG CCC CAC CTC AGA TCA AAG CAG CTC TGG ATG AGA TGG GAC CTG CAG CTC TCC CTC CAC   998

K   V   T   L   S   N   L   I   S   T   V   V   C   S   V   V   H   Q   G   L   300
    AAG GTG ACT CTT AGC AAC CTC ATT TCG ACA GTG GTT TGT AGC GTG GTG CAC CAG GGC CTT  1058

V   E   Q   I   H   T   A   L   I   K   F   P   S   L   M   K   K   K   K   K   320
    GTT GAA CAG ATC CAC ACT GCT CTA ATA AAG TTC CCA TCC TTA ATG AAA AAA AAA AAA AAA  1118
```

FIG. 8

```
                                    M   V   M   R   P   L   W   S   L   L   L   W   E    13
CCCACGCGTCCGCTCCAGAGAAAG ATG GTC ATG AGG CCC CTG TGG AGT CTG CTT CTC TGG GAA             63

A   L   L   P   I   T   V   T   G   A   Q   V   L   S   K   V   G   G   S   V           33
GCC CTA CTT CCC ATT ACA GTT ACT GGT GCC CAA GTG CTG AGC AAA GTC GGG GGC TCG GTG          123

L   L   V   A   A   R   P   P   G   F   Q   V   R   E   A   I   W   R   S   L           53
CTG CTG GTG GCA GCG CGT CCC CCT GGC TTC CAA GTC CGT GAG GCT ATC TGG CGA TCT CTC          183

W   P   S   E   E   L   L   A   T   F   F   R   G   S   L   E   T   L   Y   H           73
TGG CCT TCA GAA GAG CTC CTG GCC ACG TTT TTC CGA GGC TCC CTG GAG ACT CTG TAC CAT          243

S   R   F   L   G   R   A   Q   L   H   S   N   L   S   L   E   L   G   P   L           93
TCC CGC TTC CTG GGC CGA GCC CAG CTA CAC AGC AAC CTC AGC CTG GAG CTC GGG CCG CTG          303

E   S   G   D   S   S   N   F   S   V   L   M   V   D   T   R   G   Q   P   W          113
GAG TCT GGA GAC AGC AGC AAC TTC TCC GTG TTG ATG GTG GAC ACA AGG GGC CAG CCC TGG          363

T   Q   T   L   Q   L   K   V   Y   D   A   V   P   R   P   V   V   Q   V   F          133
ACC CAG ACC CTC CAG CTC AAG GTG TAC GAT GCA GTG CCC AGG CCC GTG GTA CAA GTG TTC          423

I   A   V   E   R   D   A   Q   P   S   K   T   C   Q   V   F   L   S   C   W          153
ATT GCT GTA GAA AGG GAT GCT CAG CCC TCC AAG ACC TGC CAG GTT TTC TTG TCC TGT TGG          483

A   P   N   I   S   E   I   T   Y   S   W   R   R   E   T   T   M   D   F   G          173
GCC CCC AAC ATC AGC GAA ATA ACC TAT AGC TGG CGA CGG GAG ACA ACC ATG GAC TTT GGT          543

M   E   P   H   S   L   F   T   D   G   Q   V   L   S   I   S   L   G   P   G          193
ATG GAA CCA CAC AGC CTC TTC ACA GAC GGA CAG GTG CTG AGC ATT TCC CTG GGA CCA GGA          603

D   R   D   V   A   Y   S   C   I   V   S   N   P   V   S   W   D   L   A   T          213
GAC AGA GAT GTG GCC TAT TCC TGC ATT GTC TCC AAC CCT GTC AGC TGG GAC TTG GCC ACA          663

V   T   P   W   D   S   C   H   H   E   A   A   P   G   K   A   S   Y   K   D          233
GTC ACG CCC TGG GAT AGC TGT CAT CAT GAG GCA GCA CCA GGG AAG GCC TCC TAC AAA GAT          723

V   L   V   V   V   V   P   V   S   L   L   L   M   L   V   T   L   F   S   A          253
GTG CTG GTG GTG GTG GTG CCT GTC TCG CTC CTC CTG ATG CTG GTT ACT CTC TTC TCT GCC          783

W   H   W   C   P   C   S   G   K   K   K   K   D   V   H   A   D   R   V   G          273
TGG CAC TGG TGC CCC TGC TCA GGG AAA AAG AAA AAG GAT GTC CAT GCT GAC AGA GTG GGT          843

P   E   T   E   N   P   L   V   Q   D   L   P   *                                      286
CCA GAG ACA GAG AAC CCC CTT GTG CAG GAT CTG CCA TAA                                      882

AGGACAATATGAACTGATGCCTGGACTATCAGTAACCCCACTGCACAGGCACACGATGCTCTGGGACATAACTGGTGCC          961

TGGAAATCACCATGGTCCTCATATCTCCCATGGGAATCCTGTCCTGCCTCGAAGGAGCAGCCTGGGCAGCCATCACACC         1040

ACGAGGACAGGAAGCACCAGCACGTTTCACACCTCCCCCTTCCCTCTCCCATCTTCTCATATCCTGGCTCTTCTCTGGG         1119
```

FIG. 9A

```
CAAGATGAGCCAAGCAGAACATTCCATCCAGGACACTGGAAGTTCTCCAGGATCCAGATCCATGGGGACATTAATAGTC    1198
CAAGGCATTCCCTCCCCCACCACTATTCATAAAGTATTAACCAACTGGCACCAAGGAATTGCCTCCAGCCTGAGTCCTA    1277
GGCTCTAAAAGATATTACATATTTGAACTAATAGAGGAACTCTGAGTCACCCATGCCAGCATCAGCTTCAGCCCCAGAC    1356
CCTGCAGTTTGAGATCTGATGCTTCCTGAGGGCCAAGGCATTGCTGTAAGAAAAGGTCTAGAAATAGGTGAAAGTGAGA    1435
GGTGGGGACAGGGGTTTCTCTTTCTGGCCTAAGGACTTTCAGGTAATCAGAGTTCATGGGCCCTCAAAGGTAAATTGC    1514
AGTTGTAGACACCGAGGATGGTTGACAACCCATGGTTGAGATGGGCACCGTTTTGCAGGAAACACCATATTAATAGACA    1593
TCCTCACCATCTCCATCCGCTCTCACGCCTCCTGCAGGATCTGGGAGTGAGGGTGGAGAGTCTTTCCTCACGCTCCAGC    1672
ACAGTGGCCAGGAAAAGAAATACTGAATTTGCCCCAGCCAACAGGACGTTCTTGCACAACTTCAAGAAAAGCAGCTCAG    1751
CTCAGGATGAGTCTTCCTGCCTGAAACTGAGAGAGTGAAGAACCATAAAACGCTATGCAGAAGGAACATTATGGAGAGA    1830
AAGGGTACTGAGGCACTCTAGAATCTGCCACATTCATTTTCAAATGCAAATGCAGAAGACTTACCTTAGTTCAAGGGGA    1909
GGGGACAAAGACCCCACAGCCCAACAGCAGGACTGTAGAGGTCACTCTGACTCCATCAAACTTTTTATTGTGGCCATCT    1988
TAGGAAAATACATTCTGCCCCTGAATGATTCTGTCTAGAAAAGCTCTGGAGTATTGATCACTACTGGAAAAACACTTAA    2067
GGAGCTAAACTTACCTTCGGGGATTATTAGCTGATAAGGTTCACAGTTTCTCTCACCCAGGTGTAACTGGATTTTTTCT    2146
GGGGCCTCAATCCAGTCTTGATAACAGCGAGGAAAGAGGTATTGAAGAAACAGGGGTGGGTTTGAAGTACTATTTTCCC    2225
AGGGTGGCTTCAATCTCCCCACCTAGGATGTCAGCCCTGTCCAAGGACCTTCCCTCTTCTCCCCAGTTCCTGGGCAATC    2304
ACTTCACCTTGGACAAAGGATCAGCACAGCTGGCCTCCAGATCCACATCACCACTCTTCCACTCGATTGTTCCCAGATC    2383
CTCCCTGCCTGGCCTGCTCAGAGGTTCCCTGTTGGTAACCTGGCTTTATCAAATTCTCATCCCTTTCCCACACCCACTT    2462
CTCTCCTATCACCTTCCCCCAAGATTACCTGAACAGGGTCCATGGCCACTCAACCTGTCAGCTTGCACCATCCCCACCT    2541
GCCACCTACAGTCAGGCCACATGCCTGGTCACTGAATCATGCAAAACTGGCCTCAGTCCCTAAAAATGATGTGGAAAGG    2620
AAAGCCCAGGATCTGACAATGAGCCCTGGTGGATTTGTGGGGAAAAAATACACAGCACTCCCCACCTTTCTTTCGTTCA    2699
TCTCCAGGGCCCCACCTCAGATCAAAGCAGCTCTGGATGAGATGGGACCTGCAGCTCTCCCTCCACAAGGTGACTCTTA    2778
GCAACCTCATTTCGACAGTGGTTTGTAGCGTGGTGCACCAGGGCCTTGTTAACAGATCCACACTGCTCTAATAAAGTT    2857
CCCATCCTTAATGAAAAAAAAAAAAAAAAAAAAAAAA                                            2894
```

FIG. 9B

| | | | | | |
|---|---|---|---|---|---|
| T195 full length | MVMRPLWSLL | LWEALLPITV | TGAQVLSKVG | GSVLLVAARP | PGFQVREAIW |
| T195 form 2 | MVMRPLWSLL | LWEALLPITV | TGAQVLSKVG | GSVLLVAARP | PGFQVREAIW |
| T195 form 1 | MVMRPLWSLL | LWEALLPITV | TGAQVLSKVG | GSVLLVAARP | PGFQVREAIW |
| T195 full length | RSLWPSEELL | ATFFRGSLET | LYHSRFLGRA | QLHSNLSLEL | GPLESGDSSN |
| T195 form 2 | RSLWPSEELL | ATFFRGSLET | LYHSRFLGRA | QLHSNLSLEL | GPLESGDSGN |
| T195 form 1 | RSLWPSEELL | ATFFRGSLET | LYHSRFLGRA | QLHSNLSLEL | GPLESGDSGN |
| T195 full length | FSVLMVDTRG | QPWTQTLQLK | VYDAVPRPVV | QVFIAVERDA | QPSKTCQVFL |
| T195 form 2 | FSVLMVDTRG | QPWTQTLQLK | VYDAVPRPVV | QVFIAVERDA | QPSKTCQVFL |
| T195 form 1 | FSVLMVDTRG | QPWTQTLQLK | VYDAVPRPVV | QVFIAVERDA | QPSKTCQVFL |
| T195 full length | SCWAPNISEI | TYSWRRETTM | DFGMEPHSLF | TDGQVLSISL | GPGDRDVAYS |
| T195 form 2 | SCWAPNISEI | TYSWRRETTM | DFGMEPHSLF | TDGQVLSISL | GPGDRDVAYS |
| T195 form 1 | SCWAPNISEI | TYSWRRETTM | DFGMEPHSLF | TDGQVLSISL | GPGDRDVAYS |
| T195 full length | CIVSNPVSWD | LATVTPWDSC | HHEAAPGKAS | YKDVLLVVVP | VSLLLMLVTL |
| T195 form 2 | CIVSNPVSWD | LATVTPWDSC | HHEAAPGKAS | YKDVLLVVVP | VSLLLMLVTL |
| T195 form 1 | CIVSNPVSWD | LATVTPWDSC | HHEAAPGKAS | YKDVLLVVVP | VSLLLMLVTL |
| T195 full length | FSAWHWCPCS | GKKKKDVHAD | R......VG | PETENPLVQD | LP......... |
| T195 form 2 | FSAWHWCPCS | GPHLRSKQLW | MRWDLQLSLH | KVTLSNLIST | VVCSVVHQGL |
| T195 form 1 | FSAWHWCPCS | GPHLRSKQLW | MRWDLQLSLH | KVTLSNLIST | VVCSVVHQGL |
| T195 full length | .......... | .......... | | | |
| T195 form 2 | VEQIHTALIK | FPSLMKKKKK | | | |
| T195 form 1 | VEQIHTCSNK | VP........ | | | |

FIG. 10

SEQUENCE LISTING

<160> NUMBER OF SEQ ID NOS: 62

<210> SEQ ID NO 1
<211> LENGTH: 2752
<212> TYPE: DNA
<213> ORGANISM: Homo sapiens
<220> FEATURE:
<221> NAME/KEY: CDS
<222> LOCATION: (557)...(2353)

<400> SEQUENCE: 1

```
gtcgacccac gcgtccgcag agaagagttt gagatgcttc ttcttcagag cacttcctac      60
tgaaagaggt atctctctgg ataggaagaa atatagtaga acccttttgaa atggatatt    120 ttcacatatt ttcgttcaga tacaaaagct ggcagttact gaaataagga cttgaagttc    180
cttcctcttt tttttatgtc ttaagagcag gaaataaaga cagctgaa ggtgtagcct     240 tgaccaactg aaagggaaat cttcatcctc tgaaaaaaca tatgtgattc tcaaaaaacg    300
catctggaaa attgataaag aagcgattct gtagattctc ccagcgctgt tgggctctca    360
attccttctg tgaaggacaa catatggtga tggggaaatc agaagctttg agaccctcta    420
cacctggata tgaatccccc ttctaatact taccagaaat gaaggggata ctcagggcag    480
agttctgaat ctcaaaacac tctactctgg caaaggaatg aagttattgg agtgatgaca    540
ggaacacggg agaaca atg ctc tgt ttg ggc tgg ata ttt ctt tgg ctt gtt    592
               Met Leu Cys Leu Gly Trp Ile Phe Leu Trp Leu Val
                 1               5                  10 gca gga gag cga att aaa gga ttt aat att tca ggt tgt tcc aca aaa    640
Ala Gly Glu Arg Ile Lys Gly Phe Asn Ile Ser Gly Cys Ser Thr Lys
        15                  20                  25 aaa ctc ctt tgg aca tat tct aca agg agt gaa gag gaa ttt gtc tta    688
Lys Leu Leu Trp Thr Tyr Ser Thr Arg Ser Glu Glu Glu Phe Val Leu
 30                  35                  40 ttt tgt gat tta cca gag cca cag aaa tca cat ttc tgc cac aga aat    736
Phe Cys Asp Leu Pro Glu Pro Gln Lys Ser His Phe Cys His Arg Asn
 45                  50                  55                  60 cga ctc tca cca aaa caa gtc cct gag cac ctg ccc ttc atg ggt agt    784
Arg Leu Ser Pro Lys Gln Val Pro Glu His Leu Pro Phe Met Gly Ser
             65                  70                  75 aac gac cta tct gat gtc caa tgg tac caa caa cct tcg aat gga gat    832
Asn Asp Leu Ser Asp Val Gln Trp Tyr Gln Gln Pro Ser Asn Gly Asp
         80                  85                  90 cca tta gag gac att agg aaa agc tat cct cac atc att cag gac aaa    880
Pro Leu Glu Asp Ile Arg Lys Ser Tyr Pro His Ile Ile Gln Asp Lys
     95                  100                 105 tgt acc ctt cac ttt ttg acc cca ggg gtg aat aat tct ggg tca tat    928
Cys Thr Leu His Phe Leu Thr Pro Gly Val Asn Asn Ser Gly Ser Tyr
 110                 115                 120 att tgt aga ccc aag atg att aag agc ccc tat gat gta gcc tgt tgt    976
Ile Cys Arg Pro Lys Met Ile Lys Ser Pro Tyr Asp Val Ala Cys Cys
125                 130                 135                 140 gtc aag atg att tta gaa gtt aag ccc cag aca aat gca tcc tgt gag   1024
Val Lys Met Ile Leu Glu Val Lys Pro Gln Thr Asn Ala Ser Cys Glu
             145                 150                 155 tat tcc gca tca cat aag caa gac cta ctt ctt ggg agc act ggc tct   1072
Tyr Ser Ala Ser His Lys Gln Asp Leu Leu Leu Gly Ser Thr Gly Ser
         160                 165                 170 att tct tgc ccc agt ctc agc tgc caa agt gat gca caa agt cca gcg   1120
Ile Ser Cys Pro Ser Leu Ser Cys Gln Ser Asp Ala Gln Ser Pro Ala
```

-continued

```
                 175                 180                 185
gta acc tgg tac aag aat gga aaa ctc ctc tct gtg gaa agg agc aac      1168
Val Thr Trp Tyr Lys Asn Gly Lys Leu Leu Ser Val Glu Arg Ser Asn
    190                 195                 200 cga atc gta gtg gat gaa gtt tat gac tat cac cag ggc aca tat gta      1216
Arg Ile Val Val Asp Glu Val Tyr Asp Tyr His Gln Gly Thr Tyr Val
205                 210                 215                 220 tgt gat tac act cag tcg gat act gtg agt tcg tgg aca gtc aga gct      1264
Cys Asp Tyr Thr Gln Ser Asp Thr Val Ser Ser Trp Thr Val Arg Ala
                225                 230                 235 gtt gtt caa gtg aga acc att gtg gga gac act aaa ctc aaa cca gat      1312
Val Val Gln Val Arg Thr Ile Val Gly Asp Thr Lys Leu Lys Pro Asp
            240                 245                 250 att ctg gat cct gtc gag gac aca ctg gaa gta gaa ctt gga aag cct      1360
Ile Leu Asp Pro Val Glu Asp Thr Leu Glu Val Glu Leu Gly Lys Pro
        255                 260                 265 tta act att agc tgc aaa gca cga ttt ggc ttt gaa agg gtc ttt aac      1408
Leu Thr Ile Ser Cys Lys Ala Arg Phe Gly Phe Glu Arg Val Phe Asn
    270                 275                 280 cct gtc ata aaa tgg tac atc aaa gat tct gac cta gag tgg gaa gtc      1456
Pro Val Ile Lys Trp Tyr Ile Lys Asp Ser Asp Leu Glu Trp Glu Val
285                 290                 295                 300 tca gta cct gag gcg aaa agt att aaa tcc act tta aag gat gaa atc      1504
Ser Val Pro Glu Ala Lys Ser Ile Lys Ser Thr Leu Lys Asp Glu Ile
                305                 310                 315 att gag cgt aat atc atc ttg gaa aaa gtc act cag cgt gat ctt cgc      1552
Ile Glu Arg Asn Ile Ile Leu Glu Lys Val Thr Gln Arg Asp Leu Arg
            320                 325                 330 agg aag ttt gtt tgc ttt gtc cag aac tcc att gga aac aca acc cag      1600
Arg Lys Phe Val Cys Phe Val Gln Asn Ser Ile Gly Asn Thr Thr Gln
        335                 340                 345 tcc gtc caa ctg aaa gaa aag aga gga gtg gtg ctg tac atc ctg          1648
Ser Val Gln Leu Lys Glu Lys Arg Gly Val Val Leu Leu Tyr Ile Leu
    350                 355                 360 ctt ggc acc atc ggg acc ctg gtg gcc gtg ctg gcg gcg agt gcc ctc      1696
Leu Gly Thr Ile Gly Thr Leu Val Ala Val Leu Ala Ala Ser Ala Leu
365                 370                 375                 380 ctc tac agg cac tgg att gaa ata gtg ctg ctc tac cgg acc tac cag      1744
Leu Tyr Arg His Trp Ile Glu Ile Val Leu Leu Tyr Arg Thr Tyr Gln
                385                 390                 395 agc aag gat cag acg ctt ggg gat aaa aag gat ttt gat gct ttc gta      1792
Ser Lys Asp Gln Thr Leu Gly Asp Lys Lys Asp Phe Asp Ala Phe Val
            400                 405                 410 tcc tat gca aaa tgg agc tct ttt cca agt gag gcc act tca tct ctg      1840
Ser Tyr Ala Lys Trp Ser Ser Phe Pro Ser Glu Ala Thr Ser Ser Leu
        415                 420                 425 agt gaa gaa cac ttg gcc ctg agc cta ttt cct gat gtt tta gaa aac      1888
Ser Glu Glu His Leu Ala Leu Ser Leu Phe Pro Asp Val Leu Glu Asn
    430                 435                 440 aaa tat gga tat agc ctg tgt ttg ctt gaa aga gat gtg gct cca gga      1936
Lys Tyr Gly Tyr Ser Leu Cys Leu Leu Glu Arg Asp Val Ala Pro Gly
445                 450                 455                 460 gga gtg tat gca gaa gac att gtg agc att att aag aga agc aga aga      1984
Gly Val Tyr Ala Glu Asp Ile Val Ser Ile Ile Lys Arg Ser Arg Arg
                465                 470                 475 gga ata ttt atc ttg agc ccc aac tat gtc aat gga ccc agt atc ttt      2032
Gly Ile Phe Ile Leu Ser Pro Asn Tyr Val Asn Gly Pro Ser Ile Phe
            480                 485                 490 gaa cta caa gca gca gtg aat ctt gcc ttg gat gat caa aca ctg aaa      2080
```

-continued

```
Glu Leu Gln Ala Ala Val Asn Leu Ala Leu Asp Asp Gln Thr Leu Lys
        495                 500                 505 ctc att tta att aag ttc tgt tac ttc caa gag cca gag tct cta cct    2128
Leu Ile Leu Ile Lys Phe Cys Tyr Phe Gln Glu Pro Glu Ser Leu Pro
510                 515                 520 cat ctc gtg aaa aaa gct ctc agg gtt ttg ccc aca gtt act tgg aga    2176
His Leu Val Lys Lys Ala Leu Arg Val Leu Pro Thr Val Thr Trp Arg
525                 530                 535                 540 ggc tta aaa tca gtt cct ccc aat tct agg ttc tgg gcc aaa atg cgc    2224
Gly Leu Lys Ser Val Pro Pro Asn Ser Arg Phe Trp Ala Lys Met Arg
                545                 550                 555 tac cac atg cct gtg aaa aac tct cag gga ttc acg tgg aac cag ctc    2272
Tyr His Met Pro Val Lys Asn Ser Gln Gly Phe Thr Trp Asn Gln Leu
            560                 565                 570 aga att acc tct agg att ttt cag tgg aaa gga ctc agt aga aca gaa    2320
Arg Ile Thr Ser Arg Ile Phe Gln Trp Lys Gly Leu Ser Arg Thr Glu
        575                 580                 585 acc act ggg agg agc tcc cag cct aag gaa tgg tgaaatgagc cctggagccc   2373
Thr Thr Gly Arg Ser Ser Gln Pro Lys Glu Trp
590                 595 cctccagtcc agtccctggg atagagatgt tgctggacag aactcacagc tctgtgtgtg   2433
tgtgttcagg ctgataggaa attcaaagag tctcctgcca gcaccaagca agcttgatgg   2493
acaatggagt gggattgaga ctgtggttta gagcctttga tttcctggac tggactgacg   2553
gcgagtgaat tctctagacc ttgggtactt tcagtacaca acaccctaa  gatttcccag   2613 tggtccgagc agaatcagaa aatacagcta cttctgcctt atggctaggg aactgtcatg   2673
tctaccatgt attgtacata tgactttatg tatacttgca atcaaataaa tattattta   2733 ttagaaaaaa aaaaaaaa                                                2752
```

<210> SEQ ID NO 2
<211> LENGTH: 599
<212> TYPE: PRT
<213> ORGANISM: Homo sapiens
<220> FEATURE:
<221> NAME/KEY: SIGNAL
<222> LOCATION: (1)...(19)

<400> SEQUENCE: 2

```
Met Leu Cys Leu Gly Trp Ile Phe Leu Trp Leu Val Ala Gly Glu Arg
            -15                 -10                  -5

Ile Lys Gly Phe Asn Ile Ser Gly Cys Ser Thr Lys Lys Leu Leu Trp
 1               5                  10

Thr Tyr Ser Thr Arg Ser Glu Glu Phe Val Leu Phe Cys Asp Leu
    15                  20                  25

Pro Glu Pro Gln Lys Ser His Phe Cys His Arg Asn Arg Leu Ser Pro
30                  35                  40                  45

Lys Gln Val Pro Glu His Leu Pro Phe Met Gly Ser Asn Asp Leu Ser
                50                  55                  60

Asp Val Gln Trp Tyr Gln Gln Pro Ser Asn Gly Asp Pro Leu Glu Asp
            65                  70                  75

Ile Arg Lys Ser Tyr Pro His Ile Ile Gln Asp Lys Cys Thr Leu His
        80                  85                  90

Phe Leu Thr Pro Gly Val Asn Asn Ser Gly Ser Tyr Ile Cys Arg Pro
    95                 100                 105

Lys Met Ile Lys Ser Pro Tyr Asp Val Ala Cys Cys Val Lys Met Ile
110                 115                 120                 125
```

```
Leu Glu Val Lys Pro Gln Thr Asn Ala Ser Cys Glu Tyr Ser Ala Ser
            130                 135                 140

His Lys Gln Asp Leu Leu Gly Ser Thr Gly Ser Ile Ser Cys Pro
        145                 150                 155

Ser Leu Ser Cys Gln Ser Asp Ala Gln Ser Pro Ala Val Thr Trp Tyr
            160                 165                 170

Lys Asn Gly Lys Leu Leu Ser Val Glu Arg Ser Asn Arg Ile Val Val
            175                 180                 185

Asp Glu Val Tyr Asp Tyr His Gln Gly Thr Tyr Val Cys Asp Tyr Thr
190                 195                 200                 205

Gln Ser Asp Thr Val Ser Ser Trp Thr Val Arg Ala Val Val Gln Val
                210                 215                 220

Arg Thr Ile Val Gly Asp Thr Lys Leu Lys Pro Asp Ile Leu Asp Pro
            225                 230                 235

Val Glu Asp Thr Leu Glu Val Glu Leu Gly Lys Pro Leu Thr Ile Ser
            240                 245                 250

Cys Lys Ala Arg Phe Gly Phe Glu Arg Val Phe Asn Pro Val Ile Lys
    255                 260                 265

Trp Tyr Ile Lys Asp Ser Asp Leu Glu Trp Glu Val Ser Val Pro Glu
270                 275                 280                 285

Ala Lys Ser Ile Lys Ser Thr Leu Lys Asp Glu Ile Ile Glu Arg Asn
                290                 295                 300

Ile Ile Leu Glu Lys Val Thr Gln Arg Asp Leu Arg Arg Lys Phe Val
                305                 310                 315

Cys Phe Val Gln Asn Ser Ile Gly Asn Thr Thr Gln Ser Val Gln Leu
        320                 325                 330

Lys Glu Lys Arg Gly Val Val Leu Leu Tyr Ile Leu Leu Gly Thr Ile
    335                 340                 345

Gly Thr Leu Val Ala Val Leu Ala Ala Ser Ala Leu Leu Tyr Arg His
350                 355                 360                 365

Trp Ile Glu Ile Val Leu Leu Tyr Arg Thr Tyr Gln Ser Lys Asp Gln
                370                 375                 380

Thr Leu Gly Asp Lys Lys Asp Phe Asp Ala Phe Val Ser Tyr Ala Lys
            385                 390                 395

Trp Ser Ser Phe Pro Ser Glu Ala Thr Ser Ser Leu Ser Glu Glu His
            400                 405                 410

Leu Ala Leu Ser Leu Phe Pro Asp Val Leu Glu Asn Lys Tyr Gly Tyr
    415                 420                 425

Ser Leu Cys Leu Leu Glu Arg Asp Val Ala Pro Gly Gly Val Tyr Ala
430                 435                 440                 445

Glu Asp Ile Val Ser Ile Ile Lys Arg Ser Arg Arg Gly Ile Phe Ile
            450                 455                 460

Leu Ser Pro Asn Tyr Val Asn Gly Pro Ser Ile Phe Glu Leu Gln Ala
        465                 470                 475

Ala Val Asn Leu Ala Leu Asp Asp Gln Thr Leu Lys Leu Ile Leu Ile
        480                 485                 490

Lys Phe Cys Tyr Phe Gln Glu Pro Glu Ser Leu Pro His Leu Val Lys
    495                 500                 505

Lys Ala Leu Arg Val Leu Pro Thr Val Thr Trp Arg Gly Leu Lys Ser
510                 515                 520                 525

Val Pro Pro Asn Ser Arg Phe Trp Ala Lys Met Arg Tyr His Met Pro
            530                 535                 540

Val Lys Asn Ser Gln Gly Phe Thr Trp Asn Gln Leu Arg Ile Thr Ser
```

-continued

```
                545                 550                 555
        Arg Ile Phe Gln Trp Lys Gly Leu Ser Arg Thr Glu Thr Thr Gly Arg
                560                 565                 570

Ser Ser Gln Pro Lys Glu Trp
                575                 580
```

<210> SEQ ID NO 3
<211> LENGTH: 1797
<212> TYPE: DNA
<213> ORGANISM: Homo sapiens

<400> SEQUENCE: 3

```
atgctctgtt tgggctggat atttctttgg cttgttgcag gagagcgaat taaaggattt      60
aatatttcag gttgttccac aaaaaaactc ctttggacat attctacaag gagtgaagag     120
gaatttgtct tattttgtga tttaccagag ccacagaaat cacatttctg ccacagaaat     180
cgactctcac aaaacaagt ccctgagcac ctgcccttca tgggtagtaa cgacctatct     240
gatgtccaat ggtaccaaca accttcgaat ggagatccat tagaggacat taggaaaagc     300
tatcctcaca tcattcagga caaatgtacc cttcactttt tgaccccagg ggtgaataat     360
tctgggtcat atatttgtag acccaagatg attaagagcc cctatgatgt agcctgttgt     420
gtcaagatga ttttagaagt taagccccag acaaatgcat cctgtgagta ttccgcatca     480
cataagcaag acctacttct gggagcact ggctctattt cttgccccag tctcagctgc     540
caaagtgatg cacaaagtcc agcggtaacc tggtacaaga atggaaaact cctctctgtg     600
gaaaggagca accgaatcgt agtggatgaa gtttatgact atcaccaggg cacatatgta     660
tgtgattaca ctcagtcgga tactgtagt cgtggacag tcagagctgt tgttcaagtg     720
agaaccattg tgggagacac taaactcaaa ccagatattc tggatcctgt cgaggacaca     780
ctggaagtag aacttggaaa gcctttaact attagctgca aagcacgatt tggctttgaa     840
agggtcttta accctgtcat aaaatggtac atcaaagatt ctgacctaga gtgggaagtc     900
tcagtacctg aggcgaaaag tattaaatcc acttttaaagg atgaaatcat tgagcgtaat     960
atcatcttgg aaaaagtcac tcagcgtgat cttcgcagga gtttgtttg ctttgtccag    1020
aactccattg gaaacacaac ccagtccgtc caactgaaag aaaagagagg agtggtgctc    1080
ctgtacatcc tgcttggcac catcgggacc ctggtggccg tgctggcggc gagtgccctc    1140
ctctacaggc actggattga atagtgctgc ctgtaccgga cctaccagag caaggatcag    1200
acgcttgggg ataaaaagga ttttgatgct ttcgtatcct atgcaaaatg gagctctttt    1260
ccaagtgagg ccacttcatc tctgagtgaa gaacacttgg ccctgagcct atttcctgat    1320
gttttagaaa acaaatatgg atatagcctg tgtttgcttg aaagagatgt ggctccagga    1380
ggagtgtatg cagaagacat tgtgagcatt attaagagaa gcagaagagg aatatttatc    1440
ttgagcccca actatgtcaa tggacccagt atctttgaac tacaagcagc agtgaatctt    1500
gccttggatg atcaaacact gaaactcatt ttaattaagt tctgttactt ccaagagcca    1560
gagtctctac ctcatctcgt gaaaaaagct ctcagggttt tgcccacagt tacttggaga    1620
ggcttaaaat cagttcctcc caattctagg ttctgggcca aaatgcgcta ccacatgcct    1680
gtgaaaaact ctcagggatt cacgtggaac cagctcagaa ttacctctag gattttttcag    1740
tggaaaggac tcagtagaac agaaaccact gggaggagct cccagcctaa ggaatgg       1797
```

<210> SEQ ID NO 4
<211> LENGTH: 1102

```
<212> TYPE: DNA
<213> ORGANISM: Homo sapiens
<220> FEATURE:
<221> NAME/KEY: CDS
<222> LOCATION: (166)...(1102)

<400> SEQUENCE: 4
gcgtccggat gttttcactt ttgggacatc ctgttctgag tcaagattcc tccttctgaa      60
catgggactt tccagaagga ccacagctcc tcccgtgcat ccactcggcc tgggaggttc     120
tggattttgg ctgtcgaggg agtttgcctg cctctccaga gaaag atg gtc atg agg    177
                                                  Met Val Met Arg
                                                    1 ccc ctg tgg agt ctg ctt ctc tgg gaa gcc cta ctt ccc att aca gtt      225
Pro Leu Trp Ser Leu Leu Leu Trp Glu Ala Leu Leu Pro Ile Thr Val
  5              10                  15                  20 act ggt gcc caa gtg ctg agc aaa gtc ggg ggc tcg gtg ctg ctg gtg      273
Thr Gly Ala Gln Val Leu Ser Lys Val Gly Gly Ser Val Leu Leu Val
                 25                  30                  35 gca gcg cgt ccc cct ggc ttc caa gtc cgt gag gct atc tgg cga tct      321
Ala Ala Arg Pro Pro Gly Phe Gln Val Arg Glu Ala Ile Trp Arg Ser
         40                  45                  50 ctc tgg cct tca gaa gag ctg ctg gcc acg ttt ttc cga ggc tcc ctg      369
Leu Trp Pro Ser Glu Glu Leu Leu Ala Thr Phe Phe Arg Gly Ser Leu
     55                  60                  65 gag act ctg tac cat tcc cgc ttc ctg ggc cga gcc cag cta cac agc      417
Glu Thr Leu Tyr His Ser Arg Phe Leu Gly Arg Ala Gln Leu His Ser
 70                  75                  80 aac ctc agc ctg gag ctc ggg ccg ctg gag tct gga gac agc ggc aac      465
Asn Leu Ser Leu Glu Leu Gly Pro Leu Glu Ser Gly Asp Ser Gly Asn
 85                  90                  95                 100 ttc tcc gtg ttg atg gtg gac aca agg ggc cag ccc tgg acc cag acc      513
Phe Ser Val Leu Met Val Asp Thr Arg Gly Gln Pro Trp Thr Gln Thr
                105                 110                 115 ctc cag ctc aag gtg tac gat gca gtg ccc agg ccc gtg gta caa gtg      561
Leu Gln Leu Lys Val Tyr Asp Ala Val Pro Arg Pro Val Val Gln Val
            120                 125                 130 ttc att gct gta gaa agg gat gct cag ccc tcc aag acc tgc cag gtt      609
Phe Ile Ala Val Glu Arg Asp Ala Gln Pro Ser Lys Thr Cys Gln Val
        135                 140                 145 ttg ttg tcc tgt tgg gcc ccc aac atc agc gaa ata acc tat agc tgg      657
Phe Leu Ser Cys Trp Ala Pro Asn Ile Ser Glu Ile Thr Tyr Ser Trp
    150                 155                 160 cga cgg gag aca acc atg gac ttt ggt atg gaa cca cac agc ctc ttc      705
Arg Arg Glu Thr Thr Met Asp Phe Gly Met Glu Pro His Ser Leu Phe
165                 170                 175                 180 aca gac gga cag gtg ctg agc att tcc ctg gga cca gga gac aga gat      753
Thr Asp Gly Gln Val Leu Ser Ile Ser Leu Gly Pro Gly Asp Arg Asp
                185                 190                 195 gtg gcc tat tcc tgc att gtc tcc aac cct gtc agc tgg gac ttg gcc      801
Val Ala Tyr Ser Cys Ile Val Ser Asn Pro Val Ser Trp Asp Leu Ala
            200                 205                 210 aca gtc acg ccc tgg gat agc tgt cat cat gag gca gca cca ggg aag      849
Thr Val Thr Pro Trp Asp Ser Cys His His Glu Ala Ala Pro Gly Lys
        215                 220                 225 gcc tcc tac aaa gat gtg ctg ctg gtg gtg cct gtc tcg ctg ctc          897
Ala Ser Tyr Lys Asp Val Leu Leu Val Val Pro Val Ser Leu Leu
    230                 235                 240 ctg atg ctg gtt act ctc ttc tct gcc tgg cac tgg tgc ccc tgc tca      945
Leu Met Leu Val Thr Leu Phe Ser Ala Trp His Trp Cys Pro Cys Ser
245                 250                 255                 260
```

-continued

| | | | | | | | | | | | | | |
|---|---|---|---|---|---|---|---|---|---|---|---|---|---|
| ggg | ccc | cac | ctc | aga | tca | aag | cag | ctc | tgg | atg | aga | tgg | gac | ctg | cag | 993 |
| Gly | Pro | His | Leu | Arg | Ser | Lys | Gln | Leu | Trp | Met | Arg | Trp | Asp | Leu | Gln | |
| | | | 265 | | | | | 270 | | | | | 275 | | | |
| ctc | tcc | ctc | ccc | aag | gtg | act | ctt | agc | aac | ctc | att | tcg | aca | gtg | gtt | 1041 |
| Leu | Ser | Leu | Pro | Lys | Val | Thr | Leu | Ser | Asn | Leu | Ile | Ser | Thr | Val | Val | |
| | | 280 | | | | | 285 | | | | | 290 | | | | |
| tgt | agc | gtg | gtg | cac | cag | ggc | ctt | gtt | gaa | cag | atc | cac | acg | tgc | tct | 1089 |
| Cys | Ser | Val | Val | His | Gln | Gly | Leu | Val | Glu | Gln | Ile | His | Thr | Cys | Ser | |
| | | 295 | | | | | 300 | | | | | 305 | | | | |
| aat | aaa | gtt | ccc | a | | | | | | | | | | | | 1102 |
| Asn | Lys | Val | Pro | | | | | | | | | | | | | |
| | 310 | | | | | | | | | | | | | | | |

<210> SEQ ID NO 5
<211> LENGTH: 312
<212> TYPE: PRT
<213> ORGANISM: Homo sapiens
<220> FEATURE:
<221> NAME/KEY: SIGNAL
<222> LOCATION: (1)...(22)

<400> SEQUENCE: 5

Met Val Met Arg Pro Leu Trp Ser Leu Leu Leu Trp Glu Ala Leu Leu
            -20                 -15                 -10

Pro Ile Thr Val Thr Gly Ala Gln Val Leu Ser Lys Val Gly Gly Ser
        -5                   1               5                  10

Val Leu Leu Val Ala Ala Arg Pro Pro Gly Phe Gln Val Arg Glu Ala
                    15                  20                  25

Ile Trp Arg Ser Leu Trp Pro Ser Glu Glu Leu Leu Ala Thr Phe Phe
                30                  35                  40

Arg Gly Ser Leu Glu Thr Leu Tyr His Ser Arg Phe Leu Gly Arg Ala
            45                  50                  55

Gln Leu His Ser Asn Leu Ser Leu Glu Leu Gly Pro Leu Glu Ser Gly
        60                  65                  70

Asp Ser Gly Asn Phe Ser Val Leu Met Val Asp Thr Arg Gly Gln Pro
75                  80                  85                  90

Trp Thr Gln Thr Leu Gln Leu Lys Val Tyr Asp Ala Val Pro Arg Pro
                95                  100                 105

Val Val Gln Val Phe Ile Ala Val Glu Arg Asp Ala Gln Pro Ser Lys
                110                 115                 120

Thr Cys Gln Val Phe Leu Ser Cys Trp Ala Pro Asn Ile Ser Glu Ile
            125                 130                 135

Thr Tyr Ser Trp Arg Arg Glu Thr Thr Met Asp Phe Gly Met Glu Pro
140                 145                 150

His Ser Leu Phe Thr Asp Gly Gln Val Leu Ser Ile Ser Leu Gly Pro
155                 160                 165                 170

Gly Asp Arg Asp Val Ala Tyr Ser Cys Ile Val Ser Asn Pro Val Ser
                175                 180                 185

Trp Asp Leu Ala Thr Val Thr Pro Trp Asp Ser Cys His His Glu Ala
            190                 195                 200

Ala Pro Gly Lys Ala Ser Tyr Lys Asp Val Leu Leu Val Val Val Pro
        205                 210                 215

Val Ser Leu Leu Leu Met Leu Val Thr Leu Phe Ser Ala Trp His Trp
    220                 225                 230

Cys Pro Cys Ser Gly Pro His Leu Arg Ser Lys Gln Leu Trp Met Arg
235                 240                 245                 250

```
Trp Asp Leu Gln Leu Ser Leu Pro Lys Val Thr Leu Ser Asn Leu Ile
            255                 260                 265

Ser Thr Val Val Cys Ser Val Val His Gln Gly Leu Val Glu Gln Ile
            270                 275                 280

His Thr Cys Ser Asn Lys Val Pro
            285                 290

<210> SEQ ID NO 6
<211> LENGTH: 936
<212> TYPE: DNA
<213> ORGANISM: Homo sapiens

<400> SEQUENCE: 6
atggtcatga ggcccctgtg gagtctgctt ctctgggaag ccctacttcc cattacagtt      60
actggtgccc aagtgctgag caaagtcggg ggctcggtgc tgctggtggc agcgcgtccc     120
cctggcttcc aagtccgtga ggctatctgg cgatctctct ggccttcaga agagctcctg     180
gccacgtttt tccgaggctc cctggagact ctgtaccatt cccgcttcct gggccgagcc     240
cagctacaca gcaacctcag cctggagctc gggccgctgg agtctggaga cagcggcaac     300
ttctccgtgt tgatggtgga cacaaggggc cagccctgga cccagaccct ccagctcaag     360
gtgtacgatg cagtgcccag gcccgtggta caagtgttca ttgctgtaga aagggatgct     420 cagcccctcca agacctgcca ggttttcttg tcctgttggg ccccaacat cagcgaaata     480 acctatagct ggcgacggga gacaaccatg gactttggta tggaaccaca cagcctcttc     540
acagacggac aggtgctgag catttccctg ggaccaggag acagagatgt ggcctattcc     600
tgcattgtct ccaaccctgt cagctgggac ttggccacag tcacgccctg ggatagctgt     660
catcatgagg cagcaccagg gaaggcctcc tacaaagatg tgctgctggt ggtggtgcct     720
gtctcgctgc tcctgatgct ggttactctc ttctctgcct ggcactggtg cccctgctca     780
gggccccacc tcagatcaaa gcagctctgg atgagatggg acctgcagct ctccctcccc     840
aaggtgactc ttagcaacct catttcgaca gtggtttgta gcgtggtgca ccagggcctt     900
gttgaacaga tccacacgtg ctctaataaa gttccc                                936

<210> SEQ ID NO 7
<211> LENGTH: 19
<212> TYPE: PRT
<213> ORGANISM: Homo sapiens
<220> FEATURE:
<221> NAME/KEY: SIGNAL
<222> LOCATION: (1)...(19)

<400> SEQUENCE: 7

Met Leu Cys Leu Gly Trp Ile Phe Leu Trp Leu Val Ala Gly Glu Arg
             -15                 -10                 -5

Ile Lys Gly

<210> SEQ ID NO 8
<211> LENGTH: 580
<212> TYPE: PRT
<213> ORGANISM: Homo sapiens

<400> SEQUENCE: 8

Phe Asn Ile Ser Gly Cys Ser Thr Lys Lys Leu Leu Trp Thr Tyr Ser
  1               5                  10                  15

Thr Arg Ser Glu Glu Glu Phe Val Leu Phe Cys Asp Leu Pro Glu Pro
             20                  25                  30
```

```
Gln Lys Ser His Phe Cys His Arg Asn Arg Leu Ser Pro Lys Gln Val
         35                  40                  45

Pro Glu His Leu Pro Phe Met Gly Ser Asn Asp Leu Ser Asp Val Gln
         50                  55                  60

Trp Tyr Gln Gln Pro Ser Asn Gly Asp Pro Leu Glu Asp Ile Arg Lys
 65                  70                  75                  80

Ser Tyr Pro His Ile Ile Gln Asp Lys Cys Thr Leu His Phe Leu Thr
                     85                  90                  95

Pro Gly Val Asn Asn Ser Gly Ser Tyr Ile Cys Arg Pro Lys Met Ile
                100                 105                 110

Lys Ser Pro Tyr Asp Val Ala Cys Cys Val Lys Met Ile Leu Glu Val
        115                 120                 125

Lys Pro Gln Thr Asn Ala Ser Cys Glu Tyr Ser Ala Ser His Lys Gln
        130                 135                 140

Asp Leu Leu Leu Gly Ser Thr Gly Ser Ile Ser Cys Pro Ser Leu Ser
145                 150                 155                 160

Cys Gln Ser Asp Ala Gln Ser Pro Ala Val Thr Trp Tyr Lys Asn Gly
                165                 170                 175

Lys Leu Leu Ser Val Glu Arg Ser Asn Arg Ile Val Val Asp Glu Val
                180                 185                 190

Tyr Asp Tyr His Gln Gly Thr Tyr Val Cys Asp Tyr Thr Gln Ser Asp
        195                 200                 205

Thr Val Ser Ser Trp Thr Val Arg Ala Val Val Gln Val Arg Thr Ile
        210                 215                 220

Val Gly Asp Thr Lys Leu Lys Pro Asp Ile Leu Asp Pro Val Glu Asp
225                 230                 235                 240

Thr Leu Glu Val Glu Leu Gly Lys Pro Leu Thr Ile Ser Cys Lys Ala
                245                 250                 255

Arg Phe Gly Phe Glu Arg Val Phe Asn Pro Val Ile Lys Trp Tyr Ile
                260                 265                 270

Lys Asp Ser Asp Leu Glu Trp Glu Val Ser Val Pro Glu Ala Lys Ser
        275                 280                 285

Ile Lys Ser Thr Leu Lys Asp Glu Ile Ile Glu Arg Asn Ile Ile Leu
        290                 295                 300

Glu Lys Val Thr Gln Arg Asp Leu Arg Arg Lys Phe Val Cys Phe Val
305                 310                 315                 320

Gln Asn Ser Ile Gly Asn Thr Thr Gln Ser Val Gln Leu Lys Glu Lys
                325                 330                 335

Arg Gly Val Val Leu Leu Tyr Ile Leu Leu Gly Thr Ile Gly Thr Leu
                340                 345                 350

Val Ala Val Leu Ala Ala Ser Ala Leu Leu Tyr Arg His Trp Ile Glu
        355                 360                 365

Ile Val Leu Leu Tyr Arg Thr Tyr Gln Ser Lys Asp Gln Thr Leu Gly
        370                 375                 380

Asp Lys Lys Asp Phe Asp Ala Phe Val Ser Tyr Ala Lys Trp Ser Ser
385                 390                 395                 400

Phe Pro Ser Glu Ala Thr Ser Ser Leu Ser Glu Glu His Leu Ala Leu
                405                 410                 415

Ser Leu Phe Pro Asp Val Leu Glu Asn Lys Tyr Gly Tyr Ser Leu Cys
                420                 425                 430

Leu Leu Glu Arg Asp Val Ala Pro Gly Gly Val Tyr Ala Glu Asp Ile
        435                 440                 445

Val Ser Ile Ile Lys Arg Ser Arg Arg Gly Ile Phe Ile Leu Ser Pro
```

```
                        450                 455                 460
Asn Tyr Val Asn Gly Pro Ser Ile Phe Glu Leu Gln Ala Ala Val Asn
465                 470                 475                 480

Leu Ala Leu Asp Asp Gln Thr Leu Lys Leu Ile Leu Lys Phe Cys
                485                 490                 495

Tyr Phe Gln Glu Pro Glu Ser Leu Pro His Leu Val Lys Lys Ala Leu
                500                 505                 510

Arg Val Leu Pro Thr Val Thr Trp Arg Gly Leu Lys Ser Val Pro Pro
                515                 520                 525

Asn Ser Arg Phe Trp Ala Lys Met Arg Tyr His Met Pro Val Lys Asn
530                 535                 540

Ser Gln Gly Phe Thr Trp Asn Gln Leu Arg Ile Thr Ser Arg Ile Phe
545                 550                 555                 560

Gln Trp Lys Gly Leu Ser Arg Thr Glu Thr Thr Gly Arg Ser Ser Gln
                565                 570                 575

Pro Lys Glu Trp
                580

<210> SEQ ID NO 9
<211> LENGTH: 338
<212> TYPE: PRT
<213> ORGANISM: Homo sapiens

<400> SEQUENCE: 9

Phe Asn Ile Ser Gly Cys Ser Thr Lys Lys Leu Leu Trp Thr Tyr Ser
1               5                   10                  15

Thr Arg Ser Glu Glu Phe Val Leu Phe Cys Asp Leu Pro Glu Pro
                20                  25                  30

Gln Lys Ser His Phe Cys His Arg Asn Arg Leu Ser Pro Lys Gln Val
                35                  40                  45

Pro Glu His Leu Pro Phe Met Gly Ser Asn Asp Leu Ser Asp Val Gln
            50                  55                  60

Trp Tyr Gln Gln Pro Ser Asn Gly Asp Pro Leu Glu Asp Ile Arg Lys
65                  70                  75                  80

Ser Tyr Pro His Ile Ile Gln Asp Lys Cys Thr Leu His Phe Leu Thr
                85                  90                  95

Pro Gly Val Asn Asn Ser Gly Ser Tyr Ile Cys Arg Pro Lys Met Ile
                100                 105                 110

Lys Ser Pro Tyr Asp Val Ala Cys Cys Val Lys Met Ile Leu Glu Val
            115                 120                 125

Lys Pro Gln Thr Asn Ala Ser Cys Glu Tyr Ser Ala Ser His Lys Gln
        130                 135                 140

Asp Leu Leu Leu Gly Ser Thr Gly Ser Ile Ser Cys Pro Ser Leu Ser
145                 150                 155                 160

Cys Gln Ser Asp Ala Gln Ser Pro Ala Val Thr Trp Tyr Lys Asn Gly
                165                 170                 175

Lys Leu Leu Ser Val Glu Arg Ser Asn Arg Ile Val Val Asp Glu Val
            180                 185                 190

Tyr Asp Tyr His Gln Gly Thr Tyr Val Cys Asp Tyr Thr Gln Ser Asp
        195                 200                 205

Thr Val Ser Ser Trp Thr Val Arg Ala Val Val Gln Val Arg Thr Ile
    210                 215                 220

Val Gly Asp Thr Lys Leu Lys Pro Asp Ile Leu Asp Pro Val Glu Asp
225                 230                 235                 240
```

```
Thr Leu Glu Val Glu Leu Gly Lys Pro Leu Thr Ile Ser Cys Lys Ala
                245                 250                 255

Arg Phe Gly Phe Glu Arg Val Phe Asn Pro Val Ile Lys Trp Tyr Ile
            260                 265                 270

Lys Asp Ser Asp Leu Glu Trp Glu Val Ser Val Pro Glu Ala Lys Ser
        275                 280                 285

Ile Lys Ser Thr Leu Lys Asp Glu Ile Ile Glu Arg Asn Ile Ile Leu
    290                 295                 300

Glu Lys Val Thr Gln Arg Asp Leu Arg Arg Lys Phe Val Cys Phe Val
305                 310                 315                 320

Gln Asn Ser Ile Gly Asn Thr Thr Gln Ser Val Gln Leu Lys Glu Lys
                325                 330                 335

Arg Gly

<210> SEQ ID NO 10
<211> LENGTH: 25
<212> TYPE: PRT
<213> ORGANISM: Homo sapiens

<400> SEQUENCE: 10

Val Val Leu Leu Tyr Ile Leu Leu Gly Thr Ile Gly Thr Leu Val Ala
1               5                   10                  15

Val Leu Ala Ala Ser Ala Leu Leu Tyr
            20                  25

<210> SEQ ID NO 11
<211> LENGTH: 217
<212> TYPE: PRT
<213> ORGANISM: Homo sapiens

<400> SEQUENCE: 11

Arg His Trp Ile Glu Ile Val Leu Leu Tyr Arg Thr Tyr Gln Ser Lys
1               5                   10                  15

Asp Gln Thr Leu Gly Asp Lys Lys Asp Phe Asp Ala Phe Val Ser Tyr
            20                  25                  30

Ala Lys Trp Ser Ser Phe Pro Ser Glu Ala Thr Ser Ser Leu Ser Glu
        35                  40                  45

Glu His Leu Ala Leu Ser Leu Phe Pro Asp Val Leu Glu Asn Lys Tyr
    50                  55                  60

Gly Tyr Ser Leu Cys Leu Leu Glu Arg Asp Val Ala Pro Gly Gly Val
65                  70                  75                  80

Tyr Ala Glu Asp Ile Val Ser Ile Ile Lys Arg Ser Arg Arg Gly Ile
                85                  90                  95

Phe Ile Leu Ser Pro Asn Tyr Val Asn Gly Pro Ser Ile Phe Glu Leu
            100                 105                 110

Gln Ala Ala Val Asn Leu Ala Leu Asp Asp Gln Thr Leu Lys Leu Ile
        115                 120                 125

Leu Ile Lys Phe Cys Tyr Phe Gln Glu Pro Glu Ser Leu Pro His Leu
    130                 135                 140

Val Lys Lys Ala Leu Arg Val Leu Pro Thr Val Thr Trp Arg Gly Leu
145                 150                 155                 160

Lys Ser Val Pro Pro Asn Ser Arg Phe Trp Ala Lys Met Arg Tyr His
                165                 170                 175

Met Pro Val Lys Asn Ser Gln Gly Phe Thr Trp Asn Gln Leu Arg Ile
            180                 185                 190

Thr Ser Arg Ile Phe Gln Trp Lys Gly Leu Ser Arg Thr Glu Thr Thr
```

195                 200                 205
Gly Arg Ser Ser Gln Pro Lys Glu Trp
    210                 215

<210> SEQ ID NO 12
<211> LENGTH: 22
<212> TYPE: PRT
<213> ORGANISM: Homo sapiens
<220> FEATURE:
<221> NAME/KEY: SIGNAL
<222> LOCATION: (1)...(22)

<400> SEQUENCE: 12

Met Val Met Arg Pro Leu Trp Ser Leu Leu Trp Glu Ala Leu Leu
        -20                 -15                 -10

Pro Ile Thr Val Thr Gly
    -5

<210> SEQ ID NO 13
<211> LENGTH: 290
<212> TYPE: PRT
<213> ORGANISM: Homo sapiens

<400> SEQUENCE: 13

Ala Gln Val Leu Ser Lys Val Gly Gly Ser Val Leu Leu Val Ala Ala
 1               5                  10                  15

Arg Pro Pro Gly Phe Gln Val Arg Glu Ala Ile Trp Arg Ser Leu Trp
                20                  25                  30

Pro Ser Glu Glu Leu Leu Ala Thr Phe Phe Arg Gly Ser Leu Glu Thr
            35                  40                  45

Leu Tyr His Ser Arg Phe Leu Gly Arg Ala Gln Leu His Ser Asn Leu
        50                  55                  60

Ser Leu Glu Leu Gly Pro Leu Glu Ser Gly Asp Ser Gly Asn Phe Ser
 65                 70                  75                  80

Val Leu Met Val Asp Thr Arg Gly Gln Pro Trp Thr Gln Thr Leu Gln
                85                  90                  95

Leu Lys Val Tyr Asp Ala Val Pro Arg Pro Val Val Gln Val Phe Ile
            100                 105                 110

Ala Val Glu Arg Asp Ala Gln Pro Ser Lys Thr Cys Gln Val Phe Leu
        115                 120                 125

Ser Cys Trp Ala Pro Asn Ile Ser Glu Ile Thr Tyr Ser Trp Arg Arg
130                 135                 140

Glu Thr Thr Met Asp Phe Gly Met Glu Pro His Ser Leu Phe Thr Asp
145                 150                 155                 160

Gly Gln Val Leu Ser Ile Ser Leu Gly Pro Gly Asp Arg Asp Val Ala
                165                 170                 175

Tyr Ser Cys Ile Val Ser Asn Pro Val Ser Trp Asp Leu Ala Thr Val
            180                 185                 190

Thr Pro Trp Asp Ser Cys His His Glu Ala Ala Pro Gly Lys Ala Ser
        195                 200                 205

Tyr Lys Asp Val Leu Leu Val Val Pro Val Ser Leu Leu Leu Met
        210                 215                 220

Leu Val Thr Leu Phe Ser Ala Trp His Trp Cys Pro Cys Ser Gly Pro
225                 230                 235                 240

His Leu Arg Ser Lys Gln Leu Trp Met Arg Trp Asp Leu Gln Leu Ser
                245                 250                 255

Leu Pro Lys Val Thr Leu Ser Asn Leu Ile Ser Thr Val Val Cys Ser

```
                260                 265                 270
Val Val His Gln Gly Leu Val Glu Gln Ile His Thr Cys Ser Asn Lys
            275                 280                 285

Val Pro
    290

<210> SEQ ID NO 14
<211> LENGTH: 211
<212> TYPE: PRT
<213> ORGANISM: Homo sapiens

<400> SEQUENCE: 14

Ala Gln Val Leu Ser Lys Val Gly Gly Ser Val Leu Leu Val Ala Ala
  1               5                  10                  15

Arg Pro Pro Gly Phe Gln Val Arg Glu Ala Ile Trp Arg Ser Leu Trp
                 20                  25                  30

Pro Ser Glu Glu Leu Leu Ala Thr Phe Phe Arg Gly Ser Leu Glu Thr
             35                  40                  45

Leu Tyr His Ser Arg Phe Leu Gly Arg Ala Gln Leu His Ser Asn Leu
         50                  55                  60

Ser Leu Glu Leu Gly Pro Leu Glu Ser Gly Asp Ser Gly Asn Phe Ser
 65                  70                  75                  80

Val Leu Met Val Asp Thr Arg Gly Gln Pro Trp Thr Gln Thr Leu Gln
                 85                  90                  95

Leu Lys Val Tyr Asp Ala Val Pro Arg Pro Val Val Gln Val Phe Ile
            100                 105                 110

Ala Val Glu Arg Asp Ala Gln Pro Ser Lys Thr Cys Gln Val Phe Leu
        115                 120                 125

Ser Cys Trp Ala Pro Asn Ile Ser Glu Ile Thr Tyr Ser Trp Arg Arg
    130                 135                 140

Glu Thr Thr Met Asp Phe Gly Met Glu Pro His Ser Leu Phe Thr Asp
145                 150                 155                 160

Gly Gln Val Leu Ser Ile Ser Leu Gly Pro Gly Asp Arg Asp Val Ala
                165                 170                 175

Tyr Ser Cys Ile Val Ser Asn Pro Val Ser Trp Asp Leu Ala Thr Val
            180                 185                 190

Thr Pro Trp Asp Ser Cys His His Glu Ala Ala Pro Gly Lys Ala Ser
        195                 200                 205

Tyr Lys Asp
    210

<210> SEQ ID NO 15
<211> LENGTH: 21
<212> TYPE: PRT
<213> ORGANISM: Homo sapiens

<400> SEQUENCE: 15

Val Leu Leu Val Val Val Pro Val Ser Leu Leu Met Leu Val Thr
  1               5                  10                  15

Leu Phe Ser Ala Trp
                 20

<210> SEQ ID NO 16
<211> LENGTH: 58
<212> TYPE: PRT
<213> ORGANISM: Homo sapiens

<400> SEQUENCE: 16
```

```
His Trp Cys Pro Cys Ser Gly Pro His Leu Arg Ser Lys Gln Leu Trp
 1               5                  10                  15

Met Arg Trp Asp Leu Gln Leu Ser Leu Pro Lys Val Thr Leu Ser Asn
             20                  25                  30

Leu Ile Ser Thr Val Val Cys Ser Val Val His Gln Gly Leu Val Glu
         35                  40                  45

Gln Ile His Thr Cys Ser Asn Lys Val Pro
     50                  55
```

<210> SEQ ID NO 17
<211> LENGTH: 58
<212> TYPE: PRT
<213> ORGANISM: Homo sapiens

<400> SEQUENCE: 17

```
Leu Pro Phe Met Gly Ser Asn Asp Leu Ser Asp Val Gln Trp Tyr Gln
 1               5                  10                  15

Gln Pro Ser Asn Gly Asp Pro Leu Glu Asp Ile Arg Lys Ser Tyr Pro
             20                  25                  30

His Ile Ile Gln Asp Lys Cys Thr Leu His Phe Leu Thr Pro Gly Val
         35                  40                  45

Asn Asn Ser Gly Ser Tyr Ile Cys Arg Pro
     50                  55
```

<210> SEQ ID NO 18
<211> LENGTH: 56
<212> TYPE: PRT
<213> ORGANISM: Homo sapiens

<400> SEQUENCE: 18

```
Gly Ser Thr Gly Ser Ile Ser Cys Pro Ser Leu Ser Cys Gln Ser Asp
 1               5                  10                  15

Ala Gln Ser Pro Ala Val Thr Trp Tyr Lys Asn Gly Lys Leu Leu Ser
             20                  25                  30

Val Glu Arg Ser Asn Arg Ile Val Val Asp Glu Val Tyr Asp Tyr His
         35                  40                  45

Gln Gly Thr Tyr Val Cys Asp Tyr
     50                  55
```

<210> SEQ ID NO 19
<211> LENGTH: 74
<212> TYPE: PRT
<213> ORGANISM: Homo sapiens

<400> SEQUENCE: 19

```
Gly Lys Pro Leu Thr Ile Ser Cys Lys Ala Arg Phe Gly Phe Glu Arg
 1               5                  10                  15

Val Phe Asn Pro Val Ile Lys Trp Tyr Ile Lys Asp Ser Asp Leu Glu
             20                  25                  30

Trp Glu Val Ser Val Pro Glu Ala Lys Ser Ile Lys Ser Thr Leu Lys
         35                  40                  45

Asp Glu Ile Ile Glu Arg Asn Ile Ile Leu Glu Lys Val Thr Gln Arg
     50                  55                  60

Asp Leu Arg Arg Lys Phe Val Cys Phe Val
 65                  70
```

<210> SEQ ID NO 20
<211> LENGTH: 335

```
<212> TYPE: PRT
<213> ORGANISM: Homo sapiens

<400> SEQUENCE: 20

Met Asp Pro Lys Gly Leu Leu Ser Leu Thr Phe Val Leu Phe Leu Ser
  1               5                  10                  15

Leu Ala Phe Gly Ala Ser Tyr Gly Thr Gly Arg Met Met Asn Cys
             20                  25                  30

Pro Lys Ile Leu Arg Gln Leu Gly Ser Lys Val Leu Leu Pro Leu Thr
             35                  40                  45

Tyr Glu Arg Ile Asn Lys Ser Met Asn Lys Ser Ile His Ile Val Val
     50                  55                  60

Thr Met Ala Lys Ser Leu Glu Asn Ser Val Glu Asn Lys Ile Val Ser
 65                  70                  75                  80

Leu Asp Pro Ser Glu Ala Gly Pro Pro Arg Tyr Leu Gly Asp Arg Tyr
                 85                  90                  95

Lys Phe Tyr Leu Glu Asn Leu Thr Leu Gly Ile Arg Glu Ser Arg Lys
             100                 105                 110

Glu Asp Glu Gly Trp Tyr Leu Met Thr Leu Glu Lys Asn Val Ser Val
         115                 120                 125

Gln Arg Phe Cys Leu Gln Leu Arg Leu Tyr Glu Gln Val Ser Thr Pro
 130                 135                 140

Glu Ile Lys Val Leu Asn Lys Thr Gln Glu Asn Gly Thr Cys Thr Leu
145                 150                 155                 160

Ile Leu Gly Cys Thr Val Glu Lys Gly Asp His Val Ala Tyr Ser Trp
                 165                 170                 175

Ser Glu Lys Ala Gly Thr His Pro Leu Asn Pro Ala Asn Ser Ser His
             180                 185                 190

Leu Leu Ser Leu Thr Leu Gly Pro Gln His Ala Asp Asn Ile Tyr Ile
         195                 200                 205

Cys Thr Val Ser Asn Pro Ile Ser Asn Asn Ser Gln Thr Phe Ser Pro
 210                 215                 220

Trp Pro Gly Cys Arg Thr Asp Pro Ser Glu Thr Lys Pro Trp Ala Val
225                 230                 235                 240

Tyr Ala Gly Leu Leu Gly Gly Val Ile Met Ile Leu Ile Met Val Val
                 245                 250                 255

Ile Leu Gln Leu Arg Arg Arg Gly Lys Thr Asn His Tyr Gln Thr Thr
             260                 265                 270

Val Glu Lys Lys Ser Leu Thr Ile Tyr Ala Gln Val Gln Lys Pro Gly
         275                 280                 285

Pro Leu Gln Lys Lys Leu Asp Ser Phe Pro Ala Gln Asp Pro Cys Thr
 290                 295                 300

Thr Ile Tyr Val Ala Ala Thr Glu Pro Val Pro Glu Ser Val Gln Glu
305                 310                 315                 320

Thr Asn Ser Ile Thr Val Tyr Ala Ser Val Thr Leu Pro Glu Ser
                 325                 330                 335

<210> SEQ ID NO 21
<211> LENGTH: 42
<212> TYPE: PRT
<213> ORGANISM: Artificial Sequence
<220> FEATURE:
<223> OTHER INFORMATION: Consensus Sequence

<400> SEQUENCE: 21

Leu Thr Cys Met Val Ser Phe His Pro Pro Asp Tyr Thr Ile Trp Trp
```

```
                1               5              10              15
Tyr Arg Asn Gly Gly Pro Ile Thr Leu Thr Ile Asn Ser Trp Gln Tyr
                        20                  25                  30

Glu Asp Ser Gly Thr Tyr Trp Cys Met Val
            35                  40

<210> SEQ ID NO 22
<211> LENGTH: 47
<212> TYPE: PRT
<213> ORGANISM: Artificial Sequence
<220> FEATURE:
<223> OTHER INFORMATION: Consensus Sequence

<400> SEQUENCE: 22

Gly Gln Ser Val Thr Leu Thr Cys Met Val Ser Phe His Pro Pro Asp
 1               5                  10                  15

Tyr Thr Ile Trp Trp Tyr Arg Asn Gly Gly Pro Ile Thr Leu Thr Ile
                20                  25                  30

Asn Ser Trp Gly Val Glu Asp Ser Gly Thr Tyr Trp Cys Met Val
            35                  40                  45

<210> SEQ ID NO 23
<211> LENGTH: 47
<212> TYPE: PRT
<213> ORGANISM: Artificial Sequence
<220> FEATURE:
<223> OTHER INFORMATION: Consensus Sequence

<400> SEQUENCE: 23

Gly Glu Ser Val Thr Leu Thr Cys Met Val Ser Phe His Pro Pro Asp
 1               5                  10                  15

Tyr Thr Ile Trp Trp Tyr Arg Asn Gly Gly Pro Ile Thr Leu Thr Ile
                20                  25                  30

Asn Ser Trp Gly Val Glu Asp Ser Gly Thr Tyr Trp Cys Met Val
            35                  40                  45

<210> SEQ ID NO 24
<211> LENGTH: 1603
<212> TYPE: DNA
<213> ORGANISM: Mus musculus
<220> FEATURE:
<221> NAME/KEY: CDS
<222> LOCATION: (43)...(876)

<400> SEQUENCE: 24
cccacgcgtc cgcccacgcg tccgcaaggg aggacaacgg cc atg tgg tcc ctc      54
                                              Met Trp Ser Leu
                                               1 tgg agt ctt ctt ctc ttt gaa gct ctc ctt ccc gtt gtg gtt gtc agt    102
Trp Ser Leu Leu Leu Phe Glu Ala Leu Leu Pro Val Val Val Val Ser
  5                  10                  15                  20 gtc caa gtg cta agc aag gta ggg gac tca gag ctg ctg gtg gcc gag    150
Val Gln Val Leu Ser Lys Val Gly Asp Ser Glu Leu Leu Val Ala Glu
                25                  30                  35 tgt cct ccg ggc ttc caa gtg cgt gag gct atc tgg cga tct ctg tgg    198
Cys Pro Pro Gly Phe Gln Val Arg Glu Ala Ile Trp Arg Ser Leu Trp
        40                  45                  50 cca tcg gag gag ctc ctg gcc aca ttt ttc cga ggt tcc ttg gag act    246
Pro Ser Glu Glu Leu Leu Ala Thr Phe Phe Arg Gly Ser Leu Glu Thr
    55                  60                  65 ctg tac cac tct cgt ttc ctg ggc cga gtc cag cta tat gac aac ctc    294
Leu Tyr His Ser Arg Phe Leu Gly Arg Val Gln Leu Tyr Asp Asn Leu
```

```
agc ctg gag ctt gga ccc ctg aaa cct gga gac agc ggc aat ttc tct    342
Ser Leu Glu Leu Gly Pro Leu Lys Pro Gly Asp Ser Gly Asn Phe Ser
 85                  90                  95                 100 gtg ctg atg gtg gat aca agg ggt caa acc tgg acc cag acc ctg tat    390
Val Leu Met Val Asp Thr Arg Gly Gln Thr Trp Thr Gln Thr Leu Tyr
                105                 110                 115 ctc aag gtg tac gat gca gta ccc aag ccc gag gtt caa gtg ttc act    438
Leu Lys Val Tyr Asp Ala Val Pro Lys Pro Glu Val Gln Val Phe Thr
            120                 125                 130 gct gca gca gag gag acc caa ccc ctc aat acc tgt cag gtc ttc ttg    486
Ala Ala Ala Glu Glu Thr Gln Pro Leu Asn Thr Cys Gln Val Phe Leu
        135                 140                 145 tcc tgc tgg gcc ccc aac atc agt gac ata acc tac agc tgg cga cgg    534
Ser Cys Trp Ala Pro Asn Ile Ser Asp Ile Thr Tyr Ser Trp Arg Arg
    150                 155                 160 gag ggg aca gtg gac ttc aat ggt gaa gtg cac agc cat ttc tca aat    582
Glu Gly Thr Val Asp Phe Asn Gly Glu Val His Ser His Phe Ser Asn
165                 170                 175                 180 gga cag gtg tta agt gtc tca ctg gga ctg ggg gac aag gat gtg gcc    630
Gly Gln Val Leu Ser Val Ser Leu Gly Leu Gly Asp Lys Asp Val Ala
                185                 190                 195 ttt acc tgc att gcc tcc aat cct gtc agc tgg gat atg acc aca gtc    678
Phe Thr Cys Ile Ala Ser Asn Pro Val Ser Trp Asp Met Thr Thr Val
            200                 205                 210 acc ccc tgg gag agc tgc cat cac gag gca gcc tcc ggg aag gcc tcc    726
Thr Pro Trp Glu Ser Cys His His Glu Ala Ala Ser Gly Lys Ala Ser
        215                 220                 225 tac aag gac gtg cta ctg gta gta gtg cca att aca ctg ttc ctg atc    774
Tyr Lys Asp Val Leu Leu Val Val Val Pro Ile Thr Leu Phe Leu Ile
    230                 235                 240 ctg gct ggt ctc ttt ggg gca tgg cac cat ggc ctc tgc tca ggg aag    822
Leu Ala Gly Leu Phe Gly Ala Trp His His Gly Leu Cys Ser Gly Lys
245                 250                 255                 260 aag aag gat gct tgc act gac ggg gtg ctt cca gag aca gag aat gcc    870
Lys Lys Asp Ala Cys Thr Asp Gly Val Leu Pro Glu Thr Glu Asn Ala
                265                 270                 275 ctc gta tagaggatgt catgagggac aacataaact ggtgcttgga ccatgatgag    926
Leu Val atgccctgct cagccacgtg atgctccaca cctggacacc tccaggatcc tcataactgc    986
cacaagtcgg cctgcctcta gcggacagcc aagaaaacca ccatcctgga acgtcaccct   1046
ggcccaaact tcctccttcc tccatcctgt tcgcacatgc cggatcctct ctgggcaagg   1106
tgaactagta ggatgcttcc ttcagaacac aggactttct ctaggatcca cagagacatt   1166
gattatccaa ggcatccatt cttctatcac tgtacataag gtcttgccca acagccacca   1226
agggacggcc tccaggccag gaccttggct caaagagaga tgagatgttt gaactaacat   1286
ggaaattgag ctaaccattg ccaactccaa ctccagcccc tggggtctga gttccttgtg   1346
ttcaagatgt tattataaga aaaggcaaag aacaggaaat gatggagggt ggggcattct   1406
ctttctggtc tgaaggactt taagattatc tgagttcaag ggccatcaaa agtaaattga   1466
gattacagat gatgagggt tggtagctaa tgtgccatgt tgggatcaaa gccatttttc   1526
tggtagcact atattaatag acacctttgt tgccatttaa aaaaaaaaa aaaaaaaaa   1586 aaaaaaaaa aaaaaa                                                    1603
```

<210> SEQ ID NO 25

```
<211> LENGTH: 278
<212> TYPE: PRT
<213> ORGANISM: Mus musculus
<220> FEATURE:
<221> NAME/KEY: SIGNAL
<222> LOCATION: (1)...(20)

<400> SEQUENCE: 25

Met Trp Ser Leu Trp Ser Leu Leu Phe Glu Ala Leu Leu Pro Val
-20              -15             -10              -5

Val Val Val Ser Val Gln Val Leu Ser Lys Val Gly Asp Ser Glu Leu
                 1               5                10

Leu Val Ala Glu Cys Pro Pro Gly Phe Gln Val Arg Glu Ala Ile Trp
             15              20              25

Arg Ser Leu Trp Pro Ser Glu Glu Leu Leu Ala Thr Phe Phe Arg Gly
     30              35                      40

Ser Leu Glu Thr Leu Tyr His Ser Arg Phe Leu Gly Arg Val Gln Leu
45              50                      55                   60

Tyr Asp Asn Leu Ser Leu Glu Leu Gly Pro Leu Lys Pro Gly Asp Ser
                65                  70              75

Gly Asn Phe Ser Val Leu Met Val Asp Thr Arg Gly Gln Thr Trp Thr
             80                  85              90

Gln Thr Leu Tyr Leu Lys Val Tyr Asp Ala Val Pro Lys Pro Glu Val
         95                  100             105

Gln Val Phe Thr Ala Ala Glu Glu Thr Gln Pro Leu Asn Thr Cys
     110             115             120

Gln Val Phe Leu Ser Cys Trp Ala Pro Asn Ile Ser Asp Ile Thr Tyr
125             130                 135                     140

Ser Trp Arg Arg Glu Gly Thr Val Asp Phe Asn Gly Glu Val His Ser
                145             150                 155

His Phe Ser Asn Gly Gln Val Leu Ser Val Ser Leu Gly Leu Gly Asp
             160             165                 170

Lys Asp Val Ala Phe Thr Cys Ile Ala Ser Asn Pro Val Ser Trp Asp
    175             180                 185

Met Thr Thr Val Thr Pro Trp Glu Ser Cys His His Glu Ala Ala Ser
190                 195                 200

Gly Lys Ala Ser Tyr Lys Asp Val Leu Val Val Val Pro Ile Thr
205             210                 215                 220

Leu Phe Leu Ile Leu Ala Gly Leu Phe Gly Ala Trp His His Gly Leu
                225             230                 235

Cys Ser Gly Lys Lys Lys Asp Ala Cys Thr Asp Gly Val Leu Pro Glu
            240                 245                 250

Thr Glu Asn Ala Leu Val
        255

<210> SEQ ID NO 26
<211> LENGTH: 834
<212> TYPE: DNA
<213> ORGANISM: Mus musculus
<220> FEATURE:
<221> NAME/KEY: CDS
<222> LOCATION: (1)...(834)

<400> SEQUENCE: 26 atg tgg tcc ctc tgg agt ctt ctt ctc ttt gaa gct ctc ctt ccc gtt      48
Met Trp Ser Leu Trp Ser Leu Leu Leu Phe Glu Ala Leu Leu Pro Val
 1               5                  10                  15 gtg gtt gtc agt gtc caa gtg cta agc aag gta ggg gac tca gag ctg      96
```

| | | | | | | | | | | | | |
|---|---|---|---|---|---|---|---|---|---|---|---|---|
| Val | Val | Val | Ser | Val | Gln | Val | Leu | Ser | Lys | Val | Gly | Asp | Ser | Glu | Leu |
| | | | 20 | | | | | 25 | | | | 30 | | | |

```
ctg gtg gcc gag tgt cct ccg ggc ttc caa gtg cgt gag gct atc tgg      144
Leu Val Ala Glu Cys Pro Pro Gly Phe Gln Val Arg Glu Ala Ile Trp
         35              40                  45 cga tct ctg tgg cca tcg gag gag ctc ctg gcc aca ttt ttc cga ggt      192
Arg Ser Leu Trp Pro Ser Glu Glu Leu Leu Ala Thr Phe Phe Arg Gly
 50              55                  60 tcc ttg gag act ctg tac cac tct cgt ttc ctg ggc cga gtc cag cta      240
Ser Leu Glu Thr Leu Tyr His Ser Arg Phe Leu Gly Arg Val Gln Leu
 65              70                  75                  80 tat gac aac ctc agc ctg gag ctt gga ccc ctg aaa cct gga gac agc      288
Tyr Asp Asn Leu Ser Leu Glu Leu Gly Pro Leu Lys Pro Gly Asp Ser
                 85                  90                  95 ggc aat ttc tct gtg ctg atg gtg gat aca agg ggt caa acc tgg acc      336
Gly Asn Phe Ser Val Leu Met Val Asp Thr Arg Gly Gln Thr Trp Thr
            100                 105                 110 cag acc ctg tat ctc aag gtg tac gat gca gta ccc aag ccc gag gtt      384
Gln Thr Leu Tyr Leu Lys Val Tyr Asp Ala Val Pro Lys Pro Glu Val
        115                 120                 125 caa gtg ttc act gct gca gca gag gag acc caa ccc ctc aat acc tgt      432
Gln Val Phe Thr Ala Ala Ala Glu Glu Thr Gln Pro Leu Asn Thr Cys
    130                 135                 140 cag gtc ttc ttg tcc tgc tgg gcc ccc aac atc agt gac ata acc tac      480
Gln Val Phe Leu Ser Cys Trp Ala Pro Asn Ile Ser Asp Ile Thr Tyr
145                 150                 155                 160 agc tgg cga cgg gag ggg aca gtg gac ttc aat ggt gaa gtg cac agc      528
Ser Trp Arg Arg Glu Gly Thr Val Asp Phe Asn Gly Glu Val His Ser
                165                 170                 175 cat ttc tca aat gga cag gtg tta agt gtc tca ctg gga ctg ggg gac      576
His Phe Ser Asn Gly Gln Val Leu Ser Val Ser Leu Gly Leu Gly Asp
            180                 185                 190 aag gat gtg gcc ttt acc tgc att gcc tcc aat cct gtc agc tgg gat      624
Lys Asp Val Ala Phe Thr Cys Ile Ala Ser Asn Pro Val Ser Trp Asp
        195                 200                 205 atg acc aca gtc acc ccc tgg gag agc tgc cat cac gag gca gcc tcc      672
Met Thr Thr Val Thr Pro Trp Glu Ser Cys His His Glu Ala Ala Ser
    210                 215                 220 ggg aag gcc tcc tac aag gac gtg cta ctg gta gta gtg cca att aca      720
Gly Lys Ala Ser Tyr Lys Asp Val Leu Leu Val Val Val Pro Ile Thr
225                 230                 235                 240 ctg ttc ctg atc ctg gct ggt ctc ttt ggg gca tgg cac cat ggc ctc      768
Leu Phe Leu Ile Leu Ala Gly Leu Phe Gly Ala Trp His His Gly Leu
                245                 250                 255 tgc tca ggg aag aag aag gat gct tgc act gac ggg gtg ctt cca gag      816
Cys Ser Gly Lys Lys Lys Asp Ala Cys Thr Asp Gly Val Leu Pro Glu
            260                 265                 270 aca gag aat gcc ctc gta                                              834
Thr Glu Asn Ala Leu Val
        275
```

<210> SEQ ID NO 27
<211> LENGTH: 20
<212> TYPE: PRT
<213> ORGANISM: Mus musculus
<220> FEATURE:
<221> NAME/KEY: SIGNAL
<222> LOCATION: (1)...(20)

<400> SEQUENCE: 27

Met Trp Ser Leu Trp Ser Leu Leu Leu Phe Glu Ala Leu Leu Pro Val

```
-20              -15              -10              -5

Val Val Val Ser

<210> SEQ ID NO 28
<211> LENGTH: 258
<212> TYPE: PRT
<213> ORGANISM: Mus musculus

<400> SEQUENCE: 28

Val Gln Val Leu Ser Lys Val Gly Asp Ser Glu Leu Leu Val Ala Glu
  1               5                  10                  15

Cys Pro Pro Gly Phe Gln Val Arg Glu Ala Ile Trp Arg Ser Leu Trp
                 20                  25                  30

Pro Ser Glu Glu Leu Leu Ala Thr Phe Phe Arg Gly Ser Leu Glu Thr
             35                  40                  45

Leu Tyr His Ser Arg Phe Leu Gly Arg Val Gln Leu Tyr Asp Asn Leu
         50                  55                  60

Ser Leu Glu Leu Gly Pro Leu Lys Pro Gly Asp Ser Gly Asn Phe Ser
 65                  70                  75                  80

Val Leu Met Val Asp Thr Arg Gly Gln Thr Trp Thr Gln Thr Leu Tyr
                 85                  90                  95

Leu Lys Val Tyr Asp Ala Val Pro Lys Pro Glu Val Gln Val Phe Thr
                100                 105                 110

Ala Ala Ala Glu Glu Thr Gln Pro Leu Asn Thr Cys Gln Val Phe Leu
            115                 120                 125

Ser Cys Trp Ala Pro Asn Ile Ser Asp Ile Thr Tyr Ser Trp Arg Arg
        130                 135                 140

Glu Gly Thr Val Asp Phe Asn Gly Glu Val His Ser His Phe Ser Asn
145                 150                 155                 160

Gly Gln Val Leu Ser Val Ser Leu Gly Leu Gly Asp Lys Asp Val Ala
                165                 170                 175

Phe Thr Cys Ile Ala Ser Asn Pro Val Ser Trp Asp Met Thr Thr Val
            180                 185                 190

Thr Pro Trp Glu Ser Cys His His Glu Ala Ala Ser Gly Lys Ala Ser
        195                 200                 205

Tyr Lys Asp Val Leu Leu Val Val Pro Ile Thr Leu Phe Leu Ile
210                 215                 220

Leu Ala Gly Leu Phe Gly Ala Trp His His Gly Leu Cys Ser Gly Lys
225                 230                 235                 240

Lys Lys Asp Ala Cys Thr Asp Gly Val Leu Pro Glu Thr Glu Asn Ala
                245                 250                 255

Leu Val

<210> SEQ ID NO 29
<211> LENGTH: 211
<212> TYPE: PRT
<213> ORGANISM: Mus musculus

<400> SEQUENCE: 29

Val Gln Val Leu Ser Lys Val Gly Asp Ser Glu Leu Leu Val Ala Glu
  1               5                  10                  15

Cys Pro Pro Gly Phe Gln Val Arg Glu Ala Ile Trp Arg Ser Leu Trp
                 20                  25                  30

Pro Ser Glu Glu Leu Leu Ala Thr Phe Phe Arg Gly Ser Leu Glu Thr
             35                  40                  45
```

```
Leu Tyr His Ser Arg Phe Leu Gly Arg Val Gln Leu Tyr Asp Asn Leu
    50                  55                  60

Ser Leu Glu Leu Gly Pro Leu Lys Pro Gly Asp Ser Gly Asn Phe Ser
 65                  70                  75                  80

Val Leu Met Val Asp Thr Arg Gly Gln Thr Trp Thr Gln Thr Leu Tyr
                 85                  90                  95

Leu Lys Val Tyr Asp Ala Val Pro Lys Pro Glu Val Gln Val Phe Thr
                100                 105                 110

Ala Ala Ala Glu Glu Thr Gln Pro Leu Asn Thr Cys Gln Val Phe Leu
                115                 120                 125

Ser Cys Trp Ala Pro Asn Ile Ser Asp Ile Thr Tyr Ser Trp Arg Arg
    130                 135                 140

Glu Gly Thr Val Asp Phe Asn Gly Glu Val His Ser His Phe Ser Asn
145                 150                 155                 160

Gly Gln Val Leu Ser Val Ser Leu Gly Leu Gly Asp Lys Asp Val Ala
                165                 170                 175

Phe Thr Cys Ile Ala Ser Asn Pro Val Ser Trp Asp Met Thr Thr Val
                180                 185                 190

Thr Pro Trp Glu Ser Cys His His Glu Ala Ala Ser Gly Lys Ala Ser
                195                 200                 205

Tyr Lys Asp
    210

<210> SEQ ID NO 30
<211> LENGTH: 21
<212> TYPE: PRT
<213> ORGANISM: Mus musculus

<400> SEQUENCE: 30

Val Leu Leu Val Val Val Pro Ile Thr Leu Phe Leu Ile Leu Ala Gly
 1               5                  10                  15

Leu Phe Gly Ala Trp
                20

<210> SEQ ID NO 31
<211> LENGTH: 26
<212> TYPE: PRT
<213> ORGANISM: Mus musculus

<400> SEQUENCE: 31

His His Gly Leu Cys Ser Gly Lys Lys Asp Ala Cys Thr Asp Gly
 1               5                  10                  15

Val Leu Pro Glu Thr Glu Asn Ala Leu Val
                20                  25

<210> SEQ ID NO 32
<211> LENGTH: 101
<212> TYPE: PRT
<213> ORGANISM: Mus musculus

<400> SEQUENCE: 32

Ser Val Gln Val Leu Ser Lys Val Gly Asp Ser Glu Leu Leu Val Ala
 1               5                  10                  15

Glu Cys Pro Pro Gly Phe Gln Val Arg Glu Ala Ile Trp Arg Ser Leu
                20                  25                  30

Trp Pro Ser Glu Glu Leu Leu Ala Thr Phe Phe Arg Gly Ser Leu Glu
                35                  40                  45

Thr Leu Tyr His Ser Arg Phe Leu Gly Arg Val Gln Leu Tyr Asp Asn
```

```
            50                  55                  60
Leu Ser Leu Glu Leu Gly Pro Leu Lys Pro Gly Asp Ser Gly Asn Phe
 65                  70                  75                  80

Ser Val Leu Met Val Asp Thr Arg Gly Gln Thr Trp Thr Gln Thr Leu
                 85                  90                  95

Tyr Leu Lys Val Tyr
                100

<210> SEQ ID NO 33
<211> LENGTH: 59
<212> TYPE: PRT
<213> ORGANISM: Mus musculus

<400> SEQUENCE: 33

Thr Cys Gln Val Phe Leu Ser Cys Trp Ala Pro Asn Ile Ser Asp Ile
  1               5                  10                  15

Thr Tyr Ser Trp Arg Arg Glu Gly Thr Val Asp Phe Asn Gly Glu Val
                 20                  25                  30

His Ser His Phe Ser Asn Gly Gln Val Leu Ser Val Ser Leu Gly Leu
                 35                  40                  45

Gly Asp Lys Asp Val Ala Phe Thr Cys Ile Ala
             50                  55

<210> SEQ ID NO 34
<211> LENGTH: 121
<212> TYPE: PRT
<213> ORGANISM: Homo sapiens

<400> SEQUENCE: 34

Leu Cys Leu Gly Trp Ile Phe Leu Trp Leu Val Ala Gly Glu Arg Ile
  1               5                  10                  15

Lys Gly Phe Asn Ile Ser Gly Cys Ser Thr Lys Lys Leu Leu Trp Thr
                 20                  25                  30

Tyr Ser Thr Arg Ser Glu Glu Glu Phe Val Leu Phe Cys Asp Leu Pro
                 35                  40                  45

Glu Pro Gln Lys Ser His Phe Cys His Arg Asn Arg Leu Ser Pro Lys
 50                  55                  60

Gln Val Pro Glu His Leu Pro Phe Met Gly Ser Asn Asp Leu Ser Asp
 65                  70                  75                  80

Val Gln Trp Tyr Gln Gln Pro Ser Asn Gly Asp Pro Leu Glu Asp Ile
                 85                  90                  95

Arg Lys Ser Tyr Pro His Ile Ile Gln Asp Lys Cys Thr Leu His Phe
                100                 105                 110

Leu Thr Pro Gly Val Asn Asn Ser Gly
            115                 120

<210> SEQ ID NO 35
<211> LENGTH: 59
<212> TYPE: PRT
<213> ORGANISM: Homo sapiens

<400> SEQUENCE: 35

Thr Cys Gln Val Phe Leu Ser Cys Trp Ala Pro Asn Ile Ser Glu Ile
  1               5                  10                  15

Thr Tyr Ser Trp Arg Arg Glu Thr Thr Met Asp Phe Gly Met Glu Pro
                 20                  25                  30

His Ser Leu Phe Thr Asp Gly Gln Val Leu Ser Ile Ser Leu Gly Pro
                 35                  40                  45
```

```
Gly Asp Arg Asp Val Ala Tyr Ser Cys Ile Val
    50              55
```

```
<210> SEQ ID NO 36
<211> LENGTH: 1118
<212> TYPE: DNA
<213> ORGANISM: Homo sapiens
<220> FEATURE:
<221> NAME/KEY: CDS
<222> LOCATION: (159)...(1118)

<400> SEQUENCE: 36
```

```
gatgttttca cttttgggac atcctgttct gagtcaagat tcctccttct gaacatggga      60
ctttccagaa ggaccacagc tcctcccgtg catccactcg gcctgggagg ttctggattt     120
tggctgtcga gggagtttgc ctgcctctcc agagaaag atg gtc atg agg ccc ctg     176
                                         Met Val Met Arg Pro Leu
                                           1               5 tgg agt ctg ctt ctc tgg gaa gcc cta ctt ccc att aca gtt act ggt       224
Trp Ser Leu Leu Leu Trp Glu Ala Leu Leu Pro Ile Thr Val Thr Gly
             10                  15                  20 gcc caa gtg ctg agc aaa gtc ggg ggc tcg gtg ctg ctg gtg gca gcg       272
Ala Gln Val Leu Ser Lys Val Gly Gly Ser Val Leu Leu Val Ala Ala
         25                  30                  35 cgt ccc cct ggc ttc caa gtc cgt gag gct atc tgg cga tct ctc tgg       320
Arg Pro Pro Gly Phe Gln Val Arg Glu Ala Ile Trp Arg Ser Leu Trp
     40                  45                  50 cct tca gaa gag ctc ctg gcc acg ttt ttc cga ggc tcc ctg gag act       368
Pro Ser Glu Glu Leu Leu Ala Thr Phe Phe Arg Gly Ser Leu Glu Thr
 55                  60                  65                  70 ctg tac cat tcc cgc ttc ctg ggc cga gcc cag cta cac agc aac ctc       416
Leu Tyr His Ser Arg Phe Leu Gly Arg Ala Gln Leu His Ser Asn Leu
                 75                  80                  85 agc ctg gag ctc ggg ccg ctg gag tct gga gac agc ggc aac ttc tcc       464
Ser Leu Glu Leu Gly Pro Leu Glu Ser Gly Asp Ser Gly Asn Phe Ser
             90                  95                 100 gtg ttg atg gtg gac aca agg ggc cag ccc tgg acc cag acc ctc cag       512
Val Leu Met Val Asp Thr Arg Gly Gln Pro Trp Thr Gln Thr Leu Gln
        105                 110                 115 ctc aag gtg tac gat gca gtg ccc agg ccc gtg gta caa gtg ttc att       560
Leu Lys Val Tyr Asp Ala Val Pro Arg Pro Val Val Gln Val Phe Ile
    120                 125                 130 gct gta gaa agg gat gct cag ccc tcc aag acc tgc agg gtt ttc ttg       608
Ala Val Glu Arg Asp Ala Gln Pro Ser Lys Thr Cys Arg Val Phe Leu
135                 140                 145                 150 tcc tgt tgg gcc ccc aac atc agc gaa ata acc tat agc tgg cga cgg       656
Ser Cys Trp Ala Pro Asn Ile Ser Glu Ile Thr Tyr Ser Trp Arg Arg
                155                 160                 165 gag aca acc atg gac ttt ggt atg gaa cca cac agc ctc ttc aca gac       704
Glu Thr Thr Met Asp Phe Gly Met Glu Pro His Ser Leu Phe Thr Asp
            170                 175                 180 gga cag gtg ctg agc att tcc ctg gga cca gga gac aga gat gtg gcc       752
Gly Gln Val Leu Ser Ile Ser Leu Gly Pro Gly Asp Arg Asp Val Ala
        185                 190                 195 tat tcc tgc att gtc tcc aac cct gtc agc tgg gac ttg gcc aca gtc       800
Tyr Ser Cys Ile Val Ser Asn Pro Val Ser Trp Asp Leu Ala Thr Val
    200                 205                 210 acg ccc tgg gat agc tgt cat cat gag gca gca cca ggg aag gcc tcc       848
Thr Pro Trp Asp Ser Cys His His Glu Ala Ala Pro Gly Lys Ala Ser
215                 220                 225                 230
```

```
tac aaa gat gtg ctg ctg gtg gtg gtg cct gtc tcg ctg ctc ctg atg      896
Tyr Lys Asp Val Leu Leu Val Val Val Pro Val Ser Leu Leu Leu Met
            235                 240                 245 ctg gtt act ctc ttc tct gcc tgg cac tgg tgc ccc tgc tca ggg ccc      944
Leu Val Thr Leu Phe Ser Ala Trp His Trp Cys Pro Cys Ser Gly Pro
            250                 255                 260 cac ctc aga tca aag cag ctc tgg atg aga tgg gac ctg cag ctc tcc      992
His Leu Arg Ser Lys Gln Leu Trp Met Arg Trp Asp Leu Gln Leu Ser
            265                 270                 275 ctc cac aag gtg act ctt agc aac ctc att tcg aca gtg gtt tgt agc     1040
Leu His Lys Val Thr Leu Ser Asn Leu Ile Ser Thr Val Val Cys Ser
            280                 285                 290 gtg gtg cac cag ggc ctt gtt gaa cag atc cac act gct cta ata aag     1088
Val Val His Gln Gly Leu Val Glu Gln Ile His Thr Ala Leu Ile Lys
295             300                 305                 310 ttc cca tcc tta atg aaa aaa aaa aaa aaa                             1118
Phe Pro Ser Leu Met Lys Lys Lys Lys Lys
            315                 320
```

<210> SEQ ID NO 37
<211> LENGTH: 320
<212> TYPE: PRT
<213> ORGANISM: Homo sapiens
<220> FEATURE:
<221> NAME/KEY: SIGNAL
<222> LOCATION: (1)...(22)

<400> SEQUENCE: 37

```
Met Val Met Arg Pro Leu Trp Ser Leu Leu Trp Glu Ala Leu Leu
        -20                 -15                 -10

Pro Ile Thr Val Thr Gly Ala Gln Val Leu Ser Lys Val Gly Gly Ser
    -5                  1                   5                  10

Val Leu Leu Val Ala Ala Arg Pro Pro Gly Phe Gln Val Arg Glu Ala
                15                  20                  25

Ile Trp Arg Ser Leu Trp Pro Ser Glu Leu Leu Ala Thr Phe Phe
            30                  35                  40

Arg Gly Ser Leu Glu Thr Leu Tyr His Ser Arg Phe Leu Gly Arg Ala
            45                  50                  55

Gln Leu His Ser Asn Leu Ser Leu Glu Leu Gly Pro Leu Glu Ser Gly
        60                  65                  70

Asp Ser Gly Asn Phe Ser Val Leu Met Val Asp Thr Arg Gly Gln Pro
75                  80                  85                  90

Trp Thr Gln Thr Leu Gln Leu Lys Val Tyr Asp Ala Val Pro Arg Pro
                95                  100                 105

Val Val Gln Val Phe Ile Ala Val Glu Arg Asp Ala Gln Pro Ser Lys
            110                 115                 120

Thr Cys Gln Val Phe Leu Ser Cys Trp Ala Pro Asn Ile Ser Glu Ile
            125                 130                 135

Thr Tyr Ser Trp Arg Arg Glu Thr Thr Met Asp Phe Gly Met Glu Pro
            140                 145                 150

His Ser Leu Phe Thr Asp Gly Gln Val Leu Ser Ile Ser Leu Gly Pro
155                 160                 165                 170

Gly Asp Arg Asp Val Ala Tyr Ser Cys Ile Val Ser Asn Pro Val Ser
                175                 180                 185

Trp Asp Leu Ala Thr Val Thr Pro Trp Asp Ser Cys His His Glu Ala
            190                 195                 200

Ala Pro Gly Lys Ala Ser Tyr Lys Asp Val Leu Leu Val Val Val Pro
            205                 210                 215
```

```
Val Ser Leu Leu Leu Met Leu Val Thr Leu Phe Ser Ala Trp His Trp
    220                 225                 230

Cys Pro Cys Ser Gly Pro His Leu Arg Ser Lys Gln Leu Trp Met Arg
235                 240                 245                 250

Trp Asp Leu Gln Leu Ser Leu His Lys Val Thr Leu Ser Asn Leu Ile
                    255                 260                 265

Ser Thr Val Val Cys Ser Val Val His Gln Gly Leu Val Glu Gln Ile
                270                 275                 280

His Thr Ala Leu Ile Lys Phe Pro Ser Leu Met Lys Lys Lys Lys
            285                 290                 295

<210> SEQ ID NO 38
<211> LENGTH: 960
<212> TYPE: DNA
<213> ORGANISM: Homo sapiens
<220> FEATURE:
<221> NAME/KEY: CDS
<222> LOCATION: (1)...(960)

<400> SEQUENCE: 38 atg gtc atg agg ccc ctg tgg agt ctg ctt ctc tgg gaa gcc cta ctt      48
Met Val Met Arg Pro Leu Trp Ser Leu Leu Leu Trp Glu Ala Leu Leu
1               5                   10                  15 ccc att aca gtt act ggt gcc caa gtg ctg agc aaa gtc ggg ggc tcg      96
Pro Ile Thr Val Thr Gly Ala Gln Val Leu Ser Lys Val Gly Gly Ser
            20                  25                  30 gtg ctg ctg gtg gca gcg cgt ccc cct ggc ttc caa gtc cgt gag gct     144
Val Leu Leu Val Ala Ala Arg Pro Pro Gly Phe Gln Val Arg Glu Ala
        35                  40                  45 atc tgg cga tct ctc tgg cct tca gaa gag ctc ctg gcc acg ttt ttc     192
Ile Trp Arg Ser Leu Trp Pro Ser Glu Glu Leu Leu Ala Thr Phe Phe
    50                  55                  60 cga ggc tcc ctg gag act ctg tac cat tcc cgc ttc ctg ggc cga gcc     240
Arg Gly Ser Leu Glu Thr Leu Tyr His Ser Arg Phe Leu Gly Arg Ala
65                  70                  75                  80 cag cta cac agc aac ctc agc ctg gag ctc ggg ccg ctg gag tct gga     288
Gln Leu His Ser Asn Leu Ser Leu Glu Leu Gly Pro Leu Glu Ser Gly
                85                  90                  95 gac agc ggc aac ttc tcc gtg ttg atg gtg gac aca agg ggc cag ccc     336
Asp Ser Gly Asn Phe Ser Val Leu Met Val Asp Thr Arg Gly Gln Pro
            100                 105                 110 tgg acc cag acc ctc cag ctc aag gtg tac gat gca gtg ccc agg ccc     384
Trp Thr Gln Thr Leu Gln Leu Lys Val Tyr Asp Ala Val Pro Arg Pro
        115                 120                 125 gtg gta caa gtg ttc att gct gta gaa agg gat gct cag ccc tcc aag     432
Val Val Gln Val Phe Ile Ala Val Glu Arg Asp Ala Gln Pro Ser Lys
    130                 135                 140 acc tgc cag gtt ttc ttg tcc tgt tgg gcc ccc aac atc agc gaa ata     480
Thr Cys Gln Val Phe Leu Ser Cys Trp Ala Pro Asn Ile Ser Glu Ile
145                 150                 155                 160 acc tat agc tgg cga cgg gag aca acc atg gac ttt ggt atg gaa cca     528
Thr Tyr Ser Trp Arg Arg Glu Thr Thr Met Asp Phe Gly Met Glu Pro
                165                 170                 175 cac agc ctc ttc aca gac gga cag gtg ctg agc att tcc ctg gga cca     576
His Ser Leu Phe Thr Asp Gly Gln Val Leu Ser Ile Ser Leu Gly Pro
            180                 185                 190 gga gac aga gat gtg gcc tat tcc tgc att gtc tcc aac cct gtc agc     624
Gly Asp Arg Asp Val Ala Tyr Ser Cys Ile Val Ser Asn Pro Val Ser
        195                 200                 205
```

-continued

```
tgg gac ttg gcc aca gtc acg ccc tgg gat agc tgt cat cat gag gca    672
Trp Asp Leu Ala Thr Val Thr Pro Trp Asp Ser Cys His His Glu Ala
210             215                 220 gca cca ggg aag gcc tcc tac aaa gat gtg ctg ctg gtg gtg gtg cct    720
Ala Pro Gly Lys Ala Ser Tyr Lys Asp Val Leu Leu Val Val Val Pro
225             230                 235                 240 gtc tcg ctg ctc ctg atg ctg gtt act ctc ttc tct gcc tgg cac tgg    768
Val Ser Leu Leu Leu Met Leu Val Thr Leu Phe Ser Ala Trp His Trp
                245                 250                 255 tgc ccc tgc tca ggg ccc cac ctc aga tca aag cag ctc tgg atg aga    816
Cys Pro Cys Ser Gly Pro His Leu Arg Ser Lys Gln Leu Trp Met Arg
                260                 265                 270 tgg gac ctg cag ctc tcc ctc cac aag gtg act ctt agc aac ctc att    864
Trp Asp Leu Gln Leu Ser Leu His Lys Val Thr Leu Ser Asn Leu Ile
            275                 280                 285 tcg aca gtg gtt tgt agc gtg gtg cac cag ggc ctt gtt gaa cag atc    912
Ser Thr Val Val Cys Ser Val Val His Gln Gly Leu Val Glu Gln Ile
            290                 295                 300 cac act gct cta ata aag ttc cca tcc tta atg aaa aaa aaa aaa aaa    960
His Thr Ala Leu Ile Lys Phe Pro Ser Leu Met Lys Lys Lys Lys Lys
305             310                 315                 320
```

<210> SEQ ID NO 39
<211> LENGTH: 22
<212> TYPE: PRT
<213> ORGANISM: Homo sapiens
<220> FEATURE:
<221> NAME/KEY: SIGNAL
<222> LOCATION: (1)...(22)

<400> SEQUENCE: 39

```
Met Val Met Arg Pro Leu Trp Ser Leu Leu Trp Glu Ala Leu Leu
        -20             -15                 -10

Pro Ile Thr Val Thr Gly
    -5
```

<210> SEQ ID NO 40
<211> LENGTH: 298
<212> TYPE: PRT
<213> ORGANISM: Homo sapiens

<400> SEQUENCE: 40

```
Ala Gln Val Leu Ser Lys Val Gly Gly Ser Val Leu Val Ala Ala
1               5                   10                  15

Arg Pro Pro Gly Phe Gln Val Arg Glu Ala Ile Trp Arg Ser Leu Trp
                20                  25                  30

Pro Ser Glu Glu Leu Leu Ala Thr Phe Phe Arg Gly Ser Leu Glu Thr
            35                  40                  45

Leu Tyr His Ser Arg Phe Leu Gly Arg Ala Gln Leu His Ser Asn Leu
    50                  55                  60

Ser Leu Glu Leu Gly Pro Leu Glu Ser Gly Asp Ser Gly Asn Phe Ser
65                  70                  75                  80

Val Leu Met Val Asp Thr Arg Gly Gln Pro Trp Thr Gln Thr Leu Gln
                85                  90                  95

Leu Lys Val Tyr Asp Ala Val Pro Arg Pro Val Val Gln Val Phe Ile
                100                 105                 110

Ala Val Glu Arg Asp Ala Gln Pro Ser Lys Thr Cys Gln Val Phe Leu
            115                 120                 125

Ser Cys Trp Ala Pro Asn Ile Ser Glu Ile Thr Tyr Ser Trp Arg Arg
    130                 135                 140
```

```
Glu Thr Thr Met Asp Phe Gly Met Glu Pro His Ser Leu Phe Thr Asp
145                 150                 155                 160

Gly Gln Val Leu Ser Ile Ser Leu Gly Pro Gly Asp Arg Asp Val Ala
                165                 170                 175

Tyr Ser Cys Ile Val Ser Asn Pro Val Ser Trp Asp Leu Ala Thr Val
            180                 185                 190

Thr Pro Trp Asp Ser Cys His His Glu Ala Ala Pro Gly Lys Ala Ser
        195                 200                 205

Tyr Lys Asp Val Leu Val Val Pro Val Ser Leu Leu Met
210                 215                 220

Leu Val Thr Leu Phe Ser Ala Trp His Trp Cys Pro Cys Ser Gly Pro
225                 230                 235                 240

His Leu Arg Ser Lys Gln Leu Trp Met Arg Trp Asp Leu Gln Leu Ser
                245                 250                 255

Leu His Lys Val Thr Leu Ser Asn Leu Ile Ser Thr Val Val Cys Ser
                260                 265                 270

Val Val His Gln Gly Leu Val Glu Gln Ile His Thr Ala Leu Ile Lys
                275                 280                 285

Phe Pro Ser Leu Met Lys Lys Lys Lys
290                 295
```

<210> SEQ ID NO 41
<211> LENGTH: 211
<212> TYPE: PRT
<213> ORGANISM: Homo sapiens

<400> SEQUENCE: 41

```
Ala Gln Val Leu Ser Lys Val Gly Gly Ser Val Leu Leu Val Ala Ala
1               5                   10                  15

Arg Pro Pro Gly Phe Gln Val Arg Glu Ala Ile Trp Arg Ser Leu Trp
                20                  25                  30

Pro Ser Glu Glu Leu Leu Ala Thr Phe Phe Arg Gly Ser Leu Glu Thr
            35                  40                  45

Leu Tyr His Ser Arg Phe Leu Gly Arg Ala Gln Leu His Ser Asn Leu
    50                  55                  60

Ser Leu Glu Leu Gly Pro Leu Glu Ser Gly Asp Ser Gly Asn Phe Ser
65                  70                  75                  80

Val Leu Met Val Asp Thr Arg Gly Gln Pro Trp Thr Gln Thr Leu Gln
                85                  90                  95

Leu Lys Val Tyr Asp Ala Val Pro Arg Pro Val Val Gln Val Phe Ile
                100                 105                 110

Ala Val Glu Arg Asp Ala Gln Pro Ser Lys Thr Cys Gln Val Phe Leu
            115                 120                 125

Ser Cys Trp Ala Pro Asn Ile Ser Glu Ile Thr Tyr Ser Trp Arg Arg
130                 135                 140

Glu Thr Thr Met Asp Phe Gly Met Glu Pro His Ser Leu Phe Thr Asp
145                 150                 155                 160

Gly Gln Val Leu Ser Ile Ser Leu Gly Pro Gly Asp Arg Asp Val Ala
                165                 170                 175

Tyr Ser Cys Ile Val Ser Asn Pro Val Ser Trp Asp Leu Ala Thr Val
            180                 185                 190

Thr Pro Trp Asp Ser Cys His His Glu Ala Ala Pro Gly Lys Ala Ser
        195                 200                 205

Tyr Lys Asp
```

```
<210> SEQ ID NO 42
<211> LENGTH: 21
<212> TYPE: PRT
<213> ORGANISM: Homo sapiens

<400> SEQUENCE: 42

Val Leu Leu Val Val Pro Val Ser Leu Leu Met Leu Val Thr
 1               5                  10                  15

Leu Phe Ser Ala Trp
             20

<210> SEQ ID NO 43
<211> LENGTH: 66
<212> TYPE: PRT
<213> ORGANISM: Homo sapiens

<400> SEQUENCE: 43

His Trp Cys Pro Cys Ser Gly Pro His Leu Arg Ser Lys Gln Leu Trp
 1               5                  10                  15

Met Arg Trp Asp Leu Gln Leu Ser Leu His Lys Val Thr Leu Ser Asn
             20                  25                  30

Leu Ile Ser Thr Val Val Cys Ser Val Val His Gln Gly Leu Val Glu
         35                  40                  45

Gln Ile His Thr Ala Leu Ile Lys Phe Pro Ser Leu Met Lys Lys Lys
     50                  55                  60

Lys Lys
 65

<210> SEQ ID NO 44
<211> LENGTH: 2894
<212> TYPE: DNA
<213> ORGANISM: Homo sapiens
<220> FEATURE:
<221> NAME/KEY: CDS
<222> LOCATION: (25)...(879)

<400> SEQUENCE: 44
cccacgcgtc cgctccagag aaag atg gtc atg agg ccc ctg tgg agt ctg         51
                          Met Val Met Arg Pro Leu Trp Ser Leu
                           1               5 ctt ctc tgg gaa gcc cta ctt ccc att aca gtt act ggt gcc caa gtg        99
Leu Leu Trp Glu Ala Leu Leu Pro Ile Thr Val Thr Gly Ala Gln Val
 10              15                  20                  25 ctg agc aaa gtc ggg ggc tcg gtg ctg ctg gtg gca gcg cgt ccc cct       147
Leu Ser Lys Val Gly Gly Ser Val Leu Leu Val Ala Ala Arg Pro Pro
                 30                  35                  40 ggc ttc caa gtc cgt gag gct atc tgg cga tct ctc tgg cct tca gaa       195
Gly Phe Gln Val Arg Glu Ala Ile Trp Arg Ser Leu Trp Pro Ser Glu
             45                  50                  55 gag ctc ctg gcc acg ttt ttc cga ggc tcc ctg gag act ctg tac cat       243
Glu Leu Leu Ala Thr Phe Phe Arg Gly Ser Leu Glu Thr Leu Tyr His
         60                  65                  70 tcc cgc ttc ctg ggc cga gcc cag cta cac agc aac ctc agc ctg gag       291
Ser Arg Phe Leu Gly Arg Ala Gln Leu His Ser Asn Leu Ser Leu Glu
     75                  80                  85 ctc ggg ccg ctg gag tct gga gac agc agc aac ttc tcc gtg ttg atg       339
Leu Gly Pro Leu Glu Ser Gly Asp Ser Ser Asn Phe Ser Val Leu Met
 90                  95                  100                 105 gtg gac aca agg ggc cag ccc tgg acc cag acc ctc cag ctc aag gtg       387
```

```
                Val Asp Thr Arg Gly Gln Pro Trp Thr Gln Thr Leu Gln Leu Lys Val
                                110                 115                 120 tac gat gca gtg ccc agg ccc gtg gta caa gtg ttc att gct gta gaa             435
Tyr Asp Ala Val Pro Arg Pro Val Val Gln Val Phe Ile Ala Val Glu
            125                 130                 135 agg gat gct cag ccc tcc aag acc tgc cag gtt ttc ttg tcc tgt tgg             483
Arg Asp Ala Gln Pro Ser Lys Thr Cys Gln Val Phe Leu Ser Cys Trp
            140                 145                 150 gcc ccc aac atc agc gaa ata acc tat agc tgg cga cgg gag aca acc             531
Ala Pro Asn Ile Ser Glu Ile Thr Tyr Ser Trp Arg Arg Glu Thr Thr
            155                 160                 165 atg gac ttt ggt atg gaa cca cac agc ctc ttc aca gac gga cag gtg             579
Met Asp Phe Gly Met Glu Pro His Ser Leu Phe Thr Asp Gly Gln Val
170                 175                 180                 185 ctg agc att tcc ctg gga cca gga gac aga gat gtg gcc tat tcc tgc             627
Leu Ser Ile Ser Leu Gly Pro Gly Asp Arg Asp Val Ala Tyr Ser Cys
                190                 195                 200 att gtc tcc aac cct gtc agc tgg gac ttg gcc aca gtc acg ccc tgg             675
Ile Val Ser Asn Pro Val Ser Trp Asp Leu Ala Thr Val Thr Pro Trp
                205                 210                 215 gat agc tgt cat cat gag gca gca cca ggg aag gcc tcc tac aaa gat             723
Asp Ser Cys His His Glu Ala Ala Pro Gly Lys Ala Ser Tyr Lys Asp
                220                 225                 230 gtg ctg ctg gtg gtg gtg cct gtc tcg ctg ctc ctg atg ctg gtt act             771
Val Leu Leu Val Val Val Pro Val Ser Leu Leu Leu Met Leu Val Thr
            235                 240                 245 ctc ttc tct gcc tgg cac tgg tgc ccc tgc tca ggg aaa aag aaa aag             819
Leu Phe Ser Ala Trp His Trp Cys Pro Cys Ser Gly Lys Lys Lys Lys
250                 255                 260                 265 gat gtc cat gct gac aga gtg ggt cca gag aca gag aac ccc ctt gtg             867
Asp Val His Ala Asp Arg Val Gly Pro Glu Thr Glu Asn Pro Leu Val
                270                 275                 280 cag gat ctg cca taaaggacaa tatgaactga tgcctggact atcagtaacc                 919
Gln Asp Leu Pro
            285 ccactgcaca ggcacacgat gctctgggac ataactggtg cctggaaatc accatggtcc          979 tcatatctcc catgggaatc ctgtcctgcc tcgaaggagc agcctgggca gccatcacac          1039 cacgaggaca ggaagcacca gcacgtttca cacctccccc ttccctctcc catcttctca          1099 tatcctggct cttctctggg caagatgagc caagcagaac attccatcca ggacactgga          1159 agttctccag gatccagatc catggggaca ttaatagtcc aaggcattcc ctcccccacc          1219 actattcata agtattaac  caactggcac caaggaattg cctccagcct gagtcctagg          1279 ctctaaaaga tattacatat ttgaactaat agaggaactc tgagtcaccc atgccagcat          1339 cagcttcagc cccagaccct gcagtttgag atctgatgct tcctgagggc caaggcattg          1399 ctgtaagaaa aggtctagaa ataggtgaaa gtgagaggtg ggggacaggg gtttctcttt          1459 ctggcctaag gactttcagg taatcagagt tcatgggccc tcaaaggtaa attgcagttg          1519 tagacaccga ggatggttga caacccatgg ttgagatggg caccgttttg caggaaacac          1579 catattaata gacatcctca ccatctccat ccgctctcac gcctcctgca ggatctggga          1639 gtgagggtgg agagtctttc ctcacgctcc agcacagtgg ccaggaaaag aaatactgaa          1699 tttgccccag ccaacaggac gttcttgcac aacttcaaga aaagcagctc agctcaggat          1759 gagtcttcct gcctgaaact gagagagtga agaaccataa aacgctatgc agaaggaaca          1819 ttatggagag aaagggtact gaggcactct agaatctgcc acattcattt tcaaatgcaa          1879
```

-continued

```
atgcagaaga cttaccttag ttcaagggga ggggacaaag accccacagc ccaacagcag   1939
gactgtagag gtcactctga ctccatcaaa cttttttattg tggccatctt aggaaaatac   1999
attctgcccc tgaatgattc tgtctagaaa agctctggag tattgatcac tactggaaaa   2059
acacttaagg agctaaactt accttcgggg attattagct gataaggttc acagtttctc   2119
tcacccaggt gtaactggat tttttctggg gcctcaatcc agtcttgata acagcgagga   2179
aagaggtatt gaagaaacag gggtgggttt gaagtactat tttcccaggg tggcttcaat   2239 ctcccccacct aggatgtcag ccctgtccaa ggaccttccc tcttctcccc agttcctggg   2299
caatcacttc accttggaca aaggatcagc acagctggcc tccagatcca catcaccact   2359
cttccactcg attgttccca gatcctccct gcctggcctg ctcagaggtt ccctgttggt   2419
aacctggctt tatcaaattc tcatcccttt cccacaccca cttctctcct atcaccttcc   2479
cccaagatta cctgaacagg gtccatggcc actcaacctg tcagcttgca ccatccccac   2539
ctgccaccta cagtcaggcc acatgcctgg tcactgaatc atgcaaaact ggcctcagtc   2599
cctaaaaatg atgtggaaag gaaagcccag gatctgacaa tgagccctgg tggatttgtg   2659
gggaaaaaat acacagcact ccccaccttt ctttcgttca tctccagggc ccacctcag    2719 atcaaagcag ctctggatga gatgggacct gcagctctcc ctccacaagg tgactcttag   2779
caacctcatt tcgacagtgg tttgtagcgt ggtgcaccag ggccttgttg aacagatcca   2839
cactgctcta ataaagttcc catccttaat gaaaaaaaaa aaaaaaaaaa aaaaa        2894
```

<210> SEQ ID NO 45
<211> LENGTH: 285
<212> TYPE: PRT
<213> ORGANISM: Homo sapiens
<220> FEATURE:
<221> NAME/KEY: SIGNAL
<222> LOCATION: (1)...(22)

<400> SEQUENCE: 45

```
Met Val Met Arg Pro Leu Trp Ser Leu Leu Trp Glu Ala Leu Leu
        -20             -15             -10

Pro Ile Thr Val Thr Gly Ala Gln Val Leu Ser Lys Val Gly Gly Ser
     -5              1               5                      10

Val Leu Val Ala Ala Arg Pro Pro Gly Phe Gln Val Arg Glu Ala
            15              20              25

Ile Trp Arg Ser Leu Trp Pro Ser Glu Glu Leu Leu Ala Thr Phe Phe
                30              35              40

Arg Gly Ser Leu Glu Thr Leu Tyr His Ser Arg Phe Leu Gly Arg Ala
            45              50              55

Gln Leu His Ser Asn Leu Ser Leu Glu Leu Gly Pro Leu Glu Ser Gly
        60              65              70

Asp Ser Ser Asn Phe Ser Val Leu Met Val Asp Thr Arg Gly Gln Pro
75              80              85              90

Trp Thr Gln Thr Leu Gln Leu Lys Val Tyr Asp Ala Val Pro Arg Pro
                95              100             105

Val Val Gln Val Phe Ile Ala Val Glu Arg Asp Ala Gln Pro Ser Lys
            110             115             120

Thr Cys Gln Val Phe Leu Ser Cys Trp Ala Pro Asn Ile Ser Glu Ile
        125             130             135

Thr Tyr Ser Trp Arg Arg Glu Thr Thr Met Asp Phe Gly Met Glu Pro
    140             145             150

His Ser Leu Phe Thr Asp Gly Gln Val Leu Ser Ile Ser Leu Gly Pro
```

```
                155                 160                 165                 170
    Gly Asp Arg Asp Val Ala Tyr Ser Cys Ile Val Ser Asn Pro Val Ser
                    175                 180                 185

Trp Asp Leu Ala Thr Val Thr Pro Trp Asp Ser Cys His His Glu Ala
                    190                 195                 200

Ala Pro Gly Lys Ala Ser Tyr Lys Asp Val Leu Leu Val Val Pro
                    205                 210                 215

Val Ser Leu Leu Leu Met Leu Val Thr Leu Phe Ser Ala Trp His Trp
        220                 225                 230

Cys Pro Cys Ser Gly Lys Lys Lys Asp Val His Ala Asp Arg Val
    235                 240                 245                 250

Gly Pro Glu Thr Glu Asn Pro Leu Val Gln Asp Leu Pro
                    255                 260

<210> SEQ ID NO 46
<211> LENGTH: 855
<212> TYPE: DNA
<213> ORGANISM: Homo sapiens
<220> FEATURE:
<221> NAME/KEY: CDS
<222> LOCATION: (1)...(855)

<400> SEQUENCE: 46 atg gtc atg agg ccc ctg tgg agt ctg ctt ctc tgg gaa gcc cta ctt           48
Met Val Met Arg Pro Leu Trp Ser Leu Leu Leu Trp Glu Ala Leu Leu
  1               5                  10                  15 ccc att aca gtt act ggt gcc caa gtg ctg agc aaa gtc ggg ggc tcg          96
Pro Ile Thr Val Thr Gly Ala Gln Val Leu Ser Lys Val Gly Gly Ser
                 20                  25                  30 gtg ctg ctg gtg gca gcg cgt ccc cct ggc ttc caa gtc cgt gag gct         144
Val Leu Leu Val Ala Ala Arg Pro Pro Gly Phe Gln Val Arg Glu Ala
             35                  40                  45 atc tgg cga tct ctc tgg cct tca gaa gag ctc ctg gcc acg ttt ttc         192
Ile Trp Arg Ser Leu Trp Pro Ser Glu Glu Leu Leu Ala Thr Phe Phe
         50                  55                  60 cga ggc tcc ctg gag act ctg tac cat tcc cgc ttc ctg ggc cga gcc         240
Arg Gly Ser Leu Glu Thr Leu Tyr His Ser Arg Phe Leu Gly Arg Ala
 65                  70                  75                  80 cag cta cac agc aac ctc agc ctg gag ctc ggg ccg ctg gag tct gga         288
Gln Leu His Ser Asn Leu Ser Leu Glu Leu Gly Pro Leu Glu Ser Gly
                 85                  90                  95 gac agc agc aac ttc tcc gtg ttg atg gtg gac aca agg ggc cag ccc         336
Asp Ser Ser Asn Phe Ser Val Leu Met Val Asp Thr Arg Gly Gln Pro
            100                 105                 110 tgg acc cag acc ctc cag ctc aag gta tac gat gca gtg ccc agg ccc         384
Trp Thr Gln Thr Leu Gln Leu Lys Val Tyr Asp Ala Val Pro Arg Pro
        115                 120                 125 gtg gta caa gtg ttc att gct gta gaa agg gat gct cag ccc tcc aag         432
Val Val Gln Val Phe Ile Ala Val Glu Arg Asp Ala Gln Pro Ser Lys
    130                 135                 140 acc tgc cag gtt ttc ttg tcc tgt tgg gcc ccc aac atc agc gaa ata         480
Thr Cys Gln Val Phe Leu Ser Cys Trp Ala Pro Asn Ile Ser Glu Ile
145                 150                 155                 160 acc tat agc tgg cga cgg gag aca acc atg gac ttt ggt atg gaa cca         528
Thr Tyr Ser Trp Arg Arg Glu Thr Thr Met Asp Phe Gly Met Glu Pro
                165                 170                 175 cac agc ctc ttc aca gac gga cag gtg ctg agc att tcc ctg gga cca         576
His Ser Leu Phe Thr Asp Gly Gln Val Leu Ser Ile Ser Leu Gly Pro
            180                 185                 190
```

-continued

| | | | | | | | | | | | | |
|---|---|---|---|---|---|---|---|---|---|---|---|---|
| gga | gac | aga | gat | gtg | gcc | tat | tcc | tgc | att | gtc | tcc | aac | cct | gtc | agc | 624 |
| Gly | Asp | Arg | Asp | Val | Ala | Tyr | Ser | Cys | Ile | Val | Ser | Asn | Pro | Val | Ser | |
| | | 195 | | | | | 200 | | | | | 205 | | | | |

| tgg | gac | ttg | gcc | aca | gtc | acg | ccc | tgg | gat | agc | tgt | cat | cat | gag | gca | 672 |
| Trp | Asp | Leu | Ala | Thr | Val | Thr | Pro | Trp | Asp | Ser | Cys | His | His | Glu | Ala | |
| 210 | | | | | 215 | | | | | 220 | | | | | | |

| gca | cca | ggg | aag | gcc | tcc | tac | aaa | gat | gtg | ctg | ctg | gtg | gtg | gtg | cct | 720 |
| Ala | Pro | Gly | Lys | Ala | Ser | Tyr | Lys | Asp | Val | Leu | Leu | Val | Val | Val | Pro | |
| 225 | | | | | 230 | | | | | 235 | | | | | 240 | |

| gtc | tcg | ctg | ctc | ctg | atg | ctg | gtt | act | ctc | ttc | tct | gcc | tgg | cac | tgg | 768 |
| Val | Ser | Leu | Leu | Leu | Met | Leu | Val | Thr | Leu | Phe | Ser | Ala | Trp | His | Trp | |
| | | | | 245 | | | | | 250 | | | | | 255 | | |

| tgc | ccc | tgc | tca | ggg | aaa | aag | aaa | aag | gat | gtc | cat | gct | gac | aga | gtg | 816 |
| Cys | Pro | Cys | Ser | Gly | Lys | Lys | Lys | Lys | Asp | Val | His | Ala | Asp | Arg | Val | |
| | | | 260 | | | | | 265 | | | | | 270 | | | |

| ggt | cca | gag | aca | gag | aac | ccc | ctt | gtg | cag | gat | ctg | cca | | | | 855 |
| Gly | Pro | Glu | Thr | Glu | Asn | Pro | Leu | Val | Gln | Asp | Leu | Pro | | | | |
| 275 | | | | | 280 | | | | | 285 | | | | | | |

<210> SEQ ID NO 47
<211> LENGTH: 22
<212> TYPE: PRT
<213> ORGANISM: Homo sapiens
<220> FEATURE:
<221> NAME/KEY: SIGNAL
<222> LOCATION: (1)...(22)

<400> SEQUENCE: 47

Met Val Met Arg Pro Leu Trp Ser Leu Leu Trp Glu Ala Leu Leu
          -20                -15                -10

Pro Ile Thr Val Thr Gly
         -5

<210> SEQ ID NO 48
<211> LENGTH: 263
<212> TYPE: PRT
<213> ORGANISM: Homo sapiens

<400> SEQUENCE: 48

Ala Gln Val Leu Ser Lys Val Gly Gly Ser Val Leu Val Ala Ala
 1               5                  10                  15

Arg Pro Pro Gly Phe Gln Val Arg Glu Ala Ile Trp Arg Ser Leu Trp
                 20                  25                  30

Pro Ser Glu Glu Leu Leu Ala Thr Phe Phe Arg Gly Ser Leu Glu Thr
             35                  40                  45

Leu Tyr His Ser Arg Phe Leu Gly Arg Ala Gln Leu His Ser Asn Leu
         50                  55                  60

Ser Leu Glu Leu Gly Pro Leu Glu Ser Gly Asp Ser Ser Asn Phe Ser
 65                  70                  75                  80

Val Leu Met Val Asp Thr Arg Gly Gln Pro Trp Thr Gln Thr Leu Gln
                 85                  90                  95

Leu Lys Val Tyr Asp Ala Val Pro Arg Pro Val Val Gln Val Phe Ile
            100                 105                 110

Ala Val Glu Arg Asp Ala Gln Pro Ser Lys Thr Cys Gln Val Phe Leu
            115                 120                 125

Ser Cys Trp Ala Pro Asn Ile Ser Glu Ile Thr Tyr Ser Trp Arg Arg
        130                 135                 140

Glu Thr Thr Met Asp Phe Gly Met Glu Pro His Ser Leu Phe Thr Asp
145                 150                 155                 160

```
Gly Gln Val Leu Ser Ile Ser Leu Gly Pro Gly Asp Arg Asp Val Ala
            165                 170                 175

Tyr Ser Cys Ile Val Ser Asn Pro Val Ser Trp Asp Leu Ala Thr Val
            180                 185                 190

Thr Pro Trp Asp Ser Cys His His Glu Ala Ala Pro Gly Lys Ala Ser
            195                 200                 205

Tyr Lys Asp Val Leu Leu Val Val Pro Val Ser Leu Leu Leu Met
210                 215                 220

Leu Val Thr Leu Phe Ser Ala Trp His Trp Cys Pro Cys Ser Gly Lys
225                 230                 235                 240

Lys Lys Lys Asp Val His Ala Asp Arg Val Gly Pro Glu Thr Glu Asn
            245                 250                 255

Pro Leu Val Gln Asp Leu Pro
            260
```

<210> SEQ ID NO 49
<211> LENGTH: 211
<212> TYPE: PRT
<213> ORGANISM: Homo sapiens

<400> SEQUENCE: 49

```
Ala Gln Val Leu Ser Lys Val Gly Gly Ser Val Leu Leu Val Ala Ala
  1               5                  10                  15

Arg Pro Pro Gly Phe Gln Val Arg Glu Ala Ile Trp Arg Ser Leu Trp
             20                  25                  30

Pro Ser Glu Glu Leu Leu Ala Thr Phe Phe Arg Gly Ser Leu Glu Thr
             35                  40                  45

Leu Tyr His Ser Arg Phe Leu Gly Arg Ala Gln Leu His Ser Asn Leu
     50                  55                  60

Ser Leu Glu Leu Gly Pro Leu Glu Ser Gly Asp Ser Gly Asn Phe Ser
 65                  70                  75                  80

Val Leu Met Val Asp Thr Arg Gly Gln Pro Trp Thr Gln Thr Leu Gln
                 85                  90                  95

Leu Lys Val Tyr Asp Ala Val Pro Arg Pro Val Val Gln Val Phe Ile
            100                 105                 110

Ala Val Glu Arg Asp Ala Gln Pro Ser Lys Thr Cys Gln Val Phe Leu
            115                 120                 125

Ser Cys Trp Ala Pro Asn Ile Ser Glu Ile Thr Tyr Ser Trp Arg Arg
130                 135                 140

Glu Thr Thr Met Asp Phe Gly Met Glu Pro His Ser Leu Phe Thr Asp
145                 150                 155                 160

Gly Gln Val Leu Ser Ile Ser Leu Gly Pro Gly Asp Arg Asp Val Ala
            165                 170                 175

Tyr Ser Cys Ile Val Ser Asn Pro Val Ser Trp Asp Leu Ala Thr Val
            180                 185                 190

Thr Pro Trp Asp Ser Cys His His Glu Ala Ala Pro Gly Lys Ala Ser
            195                 200                 205

Tyr Lys Asp
210
```

<210> SEQ ID NO 50
<211> LENGTH: 21
<212> TYPE: PRT
<213> ORGANISM: Homo sapiens

<400> SEQUENCE: 50

```
Val Leu Leu Val Val Pro Val Ser Leu Leu Met Leu Val Thr
 1               5                  10                  15

Leu Phe Ser Ala Trp
             20
```

<210> SEQ ID NO 51
<211> LENGTH: 31
<212> TYPE: PRT
<213> ORGANISM: Homo sapiens

<400> SEQUENCE: 51

```
His Trp Cys Pro Cys Ser Gly Lys Lys Lys Asp Val His Ala Asp
 1               5                  10                  15

Arg Val Gly Pro Glu Thr Glu Asn Pro Leu Val Gln Asp Leu Pro
             20                  25                  30
```

<210> SEQ ID NO 52
<211> LENGTH: 9
<212> TYPE: PRT
<213> ORGANISM: Mus musculus

<400> SEQUENCE: 52

```
Lys Val Gly Asp Ser Glu Leu Leu Val
 1               5
```

<210> SEQ ID NO 53
<211> LENGTH: 16
<212> TYPE: PRT
<213> ORGANISM: Mus musculus

<400> SEQUENCE: 53

```
Leu Met Val Asp Thr Arg Gly Gln Thr Trp Thr Gln Thr Leu Tyr Leu
 1               5                  10                  15
```

<210> SEQ ID NO 54
<211> LENGTH: 16
<212> TYPE: PRT
<213> ORGANISM: Mus musculus

<400> SEQUENCE: 54

```
Ser Trp Arg Arg Glu Gly Thr Val Asp Phe Asn Gly Glu Val His Ser
 1               5                  10                  15
```

<210> SEQ ID NO 55
<211> LENGTH: 10
<212> TYPE: PRT
<213> ORGANISM: Artificial Sequence
<220> FEATURE:
<223> OTHER INFORMATION: Fusion protein

<400> SEQUENCE: 55

```
Ala Ala Pro Gly Gly Ala Ser Tyr Lys Asp
 1               5                  10
```

<210> SEQ ID NO 56
<211> LENGTH: 10
<212> TYPE: PRT
<213> ORGANISM: Artificial Sequence
<220> FEATURE:
<223> OTHER INFORMATION: Fusion protein

<400> SEQUENCE: 56

```
Ala Ala Ser Gly Lys Ala Ser Tyr Lys Asp
 1               5                  10
```

-continued

```
<210> SEQ ID NO 57
<211> LENGTH: 21
<212> TYPE: DNA
<213> ORGANISM: Artificial Sequence
<220> FEATURE:
<223> OTHER INFORMATION: primer for PCR

<400> SEQUENCE: 57 caccccact gaaaaagatg a                                              21

<210> SEQ ID NO 58
<211> LENGTH: 23
<212> TYPE: DNA
<213> ORGANISM: Artificial Sequence
<220> FEATURE:
<223> OTHER INFORMATION: primer for PCR

<400> SEQUENCE: 58
atgcctgccg tgtgaaccac gtg                                           23

<210> SEQ ID NO 59
<211> LENGTH: 26
<212> TYPE: DNA
<213> ORGANISM: Artificial Sequence
<220> FEATURE:
<223> OTHER INFORMATION: primer for PCR

<400> SEQUENCE: 59
cttaactatc ttgggctgtg acaaag                                        26

<210> SEQ ID NO 60
<211> LENGTH: 27
<212> TYPE: DNA
<213> ORGANISM: Artificial Sequence
<220> FEATURE:
<223> OTHER INFORMATION: primer for PCR

<400> SEQUENCE: 60
gcctaaggac tttcaggtaa tcagagt                                       27

<210> SEQ ID NO 61
<211> LENGTH: 27
<212> TYPE: DNA
<213> ORGANISM: Artificial Sequence
<220> FEATURE:
<223> OTHER INFORMATION: primer for PCR

<400> SEQUENCE: 61
catgggccct caaaggtaaa ttgcagt                                       27

<210> SEQ ID NO 62
<211> LENGTH: 22
<212> TYPE: DNA
<213> ORGANISM: Artificial Sequence
<220> FEATURE:
<223> OTHER INFORMATION: primer for PCR

<400> SEQUENCE: 62
tgtcaaccat cctcggtgtc ta                                            22
```

NUCLEIC ACIDS ENCODING HUMAN TANGO 195

RELATED APPLICATION INFORMATION

This application is a continuation of U.S. application Ser. No. 09/731,449, filed Dec. 7, 2000, now abandoned, which is a continuation-in-part of U.S. application Ser. No. 09/410,359, filed Sep. 30, 1999, now abandoned, which is a continuation-in-part of U.S. application Ser. No. 09/163,523, filed Sep. 30, 1998, now abandoned, the contents of each of these applications is hereby incorporated by reference.

BACKGROUND OF THE INVENTION

Many secreted proteins, for example, cytokines and cytokine receptors, play a vital role in the regulation of cell growth, cell differentiation, and a variety of specific cellular responses. A number of medically useful proteins, including erythropoietin, granulocyte-macrophage colony stimulating factor, human growth hormone, and various interleukins, are secreted proteins. Thus, an important goal in the design and development of new therapies is the identification and characterization of secreted proteins and the genes which encode them.

Many secreted proteins are receptors which bind a ligand and transduce an intracellular signal, leading to a variety of cellular responses. The identification and characterization of such a receptor enables one to identify both the ligands which bind to the receptor and the intracellular molecules and signal transduction pathways associated with the receptor, permitting one to identify or design modulators of receptor activity, e.g., receptor agonists or antagonists and modulators of signal transduction.

SUMMARY OF THE INVENTION

The present invention is based, at least in part, on the discovery of cDNA molecules encoding TANGO 191 and TANGO 195, both of which are transmembrane proteins. These proteins, fragments, derivatives, and variants thereof are collectively referred to as "polypeptides of the invention" or "proteins of the invention." Nucleic acid molecules encoding polypeptides of the invention are collectively referred to as "nucleic acids of the invention."

The nucleic acids and polypeptides of the present invention are useful as modulating agents in regulating a variety of cellular processes. Accordingly, in one aspect, this invention provides isolated nucleic acid molecules encoding a polypeptide of the invention or a biologically active portion thereof. The present invention also provides nucleic acid molecules which are suitable as primers or hybridization probes for the detection of nucleic acids encoding a polypeptide of the invention.

The invention features nucleic acid molecules which are at least about 45% (or 55%, 65%, 75%, 85%, 95%, or 98%) identical to the nucleotide sequence shown in SEQ ID NO:1, 3, 4, 6, 24, 26, 36, 38, 44, or 46, or the nucleotide sequence of the cDNA insert of either the clone deposited with the American Type Culture Collection, Manassas, Va. (ATCC) as Accession Number 98881 or the clone deposited with the ATCC as Accession Number 98882 (the "cDNA of ATCC 98881" or the "cDNA of ATCC 98882"), or a complement thereof.

The invention features nucleic acid molecules which include a fragment of at least 300 (325, 350, 375, 400, 425, 450, 500, 550, 600, 650, 700, 800, 900, 1000, or 1200) nucleotides of the nucleotide sequence of SEQ ID NO:1, 3, 4, 6, 24, 26, 36, 38, 44, or 46, or the nucleotide sequence of the cDNA of ATCC 98881 or the cDNA of ATCC 98882, or a complement thereof.

The invention also features nucleic acid molecules which include a nucleotide sequence encoding a protein having an amino acid sequence that is at least about 45% (or 55%, 65%, 75%, 85%, 95%, or 98%) identical to the amino acid sequence of SEQ ID NO:2, 5, 25, 37, or 45, or the amino acid sequence encoded by the cDNA of ATCC 98881 or the cDNA of ATCC 98882, or a complement thereof.

In preferred embodiments, the nucleic acid molecules have the nucleotide sequence of SEQ ID NO:1, 3, 4, 6, 24, 26, 36, 38, 44, or 46, or the nucleotide sequence of the cDNA of ATCC 98881, or the cDNA of ATCC 98882.

Also within the invention are nucleic acid molecules which encode a fragment of a polypeptide having the amino acid sequence of SEQ ID NO:2, 5, 25, 37, or 45, the fragment including at least 15 (25, 30, 50, 100, 150, 300, or 400) contiguous amino acids of SEQ ID NO:2, 5, 25, 37, or 45, the polypeptide encoded by the cDNA of ATCC 98881, or the polypeptide encoded by the cDNA of ATCC 98882.

The invention includes nucleic acid molecules which encode a naturally occurring allelic variant of a polypeptide comprising the amino acid sequence of SEQ ID NO:2, 5, 25, 37, or 45, the amino acid sequence encoded by the cDNA of ATCC 98881, or the amino acid sequence encoded by the cDNA of ATCC 98882, wherein the nucleic acid molecule hybridizes to a nucleic acid molecule having a nucleic acid sequence encoding SEQ ID NO:2, 5, 25, 37, or 45, or a complement thereof under stringent conditions.

Also within the invention are isolated polypeptides or proteins having an amino acid sequence that is at least about 65%, preferably 75%, 85%, 95%, or 98% identical to the amino acid sequence of SEQ ID NO:2, 5, 25, 37, or 45.

Also within the invention are isolated polypeptides or proteins which are encoded by a nucleic acid molecule having a nucleotide sequence that is at least about 65%, preferably 75%, 85%, or 95% identical to a nucleic acid sequence encoding SEQ ID NO:2, 5, 25, 37, or 45; and isolated polypeptides or proteins which are encoded by a nucleic acid molecule having a nucleotide sequence which hybridizes under stringent hybridization conditions to a nucleic acid molecule having the nucleotide sequence of SEQ ID NO:1, 3, 4, 6, 24, 26, 36, 38, 44, or 46, a complement thereof or the non-coding strand of the cDNA of ATCC 98881 or the cDNA of ATCC 98882.

Also within the invention are polypeptides which are a naturally occurring allelic variants of a polypeptide that includes the amino acid sequence of SEQ ID NO:2, 5, 25, 37, or 45, an amino acid sequence encoded by the cDNA of ATCC 98881, or an amino acid sequence encoded by the cDNA of ATCC 98882, wherein the polypeptide is encoded by a nucleic acid molecule which hybridizes to a nucleic acid molecule having the sequence of SEQ ID NO:1, 3, 4, 6, 24, 26 36, 38, 44, or 46, or a complement thereof under stringent conditions.

The invention also features nucleic acid molecules that hybridize under stringent conditions to a nucleic acid molecule having the nucleotide sequence of SEQ ID NO:1, 3, 4, 6, 24, 26, 36, 38, 44, or 46, the cDNA of ATCC 98881 or the cDNA of ATCC 98882, or a complement thereof. In other embodiments, the nucleic acid molecules are at least 300 (325, 350, 375, 400, 425, 450, 500, 550, 600, 650, 700, 800, 900, 1000, or 1290) nucleotides in length and hybridizes under stringent conditions to a nucleic acid molecule having the nucleotide sequence of SEQ ID NO:1, 3, 4, 6, 24, 26, 36, 38, 44, or 46, the cDNA ATCC 98881, or the cDNA of ATCC 98882, or a complement thereof.

In preferred embodiments, the isolated nucleic acid molecules encode a cytoplasmic (SEQ ID NO:11, 16, 31, 43, or 51), transmembrane (SEQ ID NO:10, 15, 30, 42, or 50), or extracellular (SEQ ID NO:9, 14, 29, 41, or 49) domain of a polypeptide of the invention or a complement thereof. In another embodiment, the invention provides an isolated nucleic acid molecule which is antisense to the coding strand of a nucleic acid of the invention.

Another aspect of the invention provides vectors, e.g., recombinant expression vectors, comprising a nucleic acid molecule of the invention. In another embodiment, the invention provides host cells containing such a vector. The invention also provides methods for producing a polypeptide of the invention by culturing, in a suitable medium, a host cell of the invention containing a recombinant expression vector such that a the polypeptide is produced.

Another aspect of this invention features isolated or recombinant proteins and polypeptides of the invention. Preferred proteins and polypeptides possess at least one biological activity possessed by the corresponding naturally-occurring human polypeptide. An activity, a biological activity, and a functional activity of a polypeptide of the invention refers to an activity exerted by a protein, polypeptide or nucleic acid molecule of the invention on, for example, a responsive cell as determined in vivo, or in vitro, according to standard techniques. Such activities can include direct activities, such as an association with or an enzymatic activity on a second protein or indirect activities, such as a cellular signaling activity mediated by interaction of the protein with a second protein.

For TANGO 191, biological activities include, e.g., (1) the ability to form protein:protein interactions with proteins in the signaling pathway of the naturally-occurring polypeptide; (2) the ability to bind a ligand of the naturally-occurring polypeptide; and (3) the ability to interact with a TANGO 191 receptor. Other activities include the ability to modulate function, survival, morphology, proliferation, and/or differentiation of cells of tissues in which it is expressed.

For TANGO 195, biological activities include, e.g., (1) the ability to form protein:protein interactions with proteins in the signaling pathway of the naturally-occurring polypeptide; (2) the ability to bind a ligand of the naturally-occurring polypeptide; (3) the ability to modulate function, survival, maturation, morphology, proliferation, and/or differentiation of B cells, e.g., B1b "sister" cells; (4) the ability to modulate signals through the B cell receptor complex; (5) the ability to bind to a receptor on B cells; (6) the ability to act as a costimulatory molecule for immune cells, e.g., B cells or T cells; (7) the ability to act as an adhesion molecule; (8) the ability to modulate the expression of interleukins, e.g., IL9; (9) the ability to bind to a ligand, the expression of which is modulated by an interleukin, e.g., IL9; (10) the ability to bind to TANGO 195 receptors, e.g., receptors that map to the same chromosomal position as TANGO 195, e.g., receptors CD84 and/or Ly9. Other activities include the ability to modulate function, survival, morphology, proliferation, and/or differentiation of cells of tissues in which it is expressed (e.g., lymphoid organs, including spleen, lymph nodes, thymus, and bone marrow).

In one embodiment, a polypeptide of the invention has an amino acid sequence sufficiently identical to at least one domain of a polypeptide of the invention. As used herein, the term "sufficiently identical" refers to a first amino acid or nucleotide sequence which contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences which contain a common structural domain having about 65% identity, preferably 75% identity, more preferably 85%, 95%, or 98% identity are defined herein as sufficiently identical.

In one embodiment, a TANGO 191 polypeptide of the invention includes one or more of the following domains: (1) a signal sequence; (2) an extracellular domain; (3) a transmembrane domain; and (4) a cytoplasmic domain.

In another embodiment, a nucleic acid molecule of the invention encodes a TANGO 191 polypeptide with one or more of the following domains: (1) a signal sequence; (2) an extracellular domain; (3) a transmembrane domain; and (4) a cytoplasmic domain.

In another embodiment, a TANGO 191 polypeptide lacks both a transmembrane and a cytoplasmic domain.

In another embodiment a nucleic acid molecule of the invention encodes a TANGO 191 polypeptide which lacks both a transmembrane and a cytoplasmic domain.

In another embodiment, a TANGO 191 polypeptide lacks both a transmembrane domain and a cytoplasmic domain and is soluble under physiological conditions.

In another embodiment, a nucleic acid molecule of the invention encodes a TANGO 191 polypeptide which lacks both a transmembrane domain and a cytoplasmic domain and is soluble under physiological conditions.

In another embodiment, a TANGO 195 polypeptide of the invention includes one or more of the following domains: (1) a signal sequence; (2) an extracellular domain; (3) a transmembrane domain; (4) a cytoplasmic domain; and (5) one or more immunoglobulin domains.

In another embodiment, a nucleic acid molecule of the invention encodes a TANGO 195 polypeptide with one or more of the following domains: (1) a signal sequence; (2) an extracellular domain; (3) a transmembrane domain; (4) a cytoplasmic domain; and (5) one or more immunoglobulin domains.

In another embodiment, a TANGO 195 polypeptide lacks both a transmembrane and a cytoplasmic domain.

In another embodiment, a nucleic acid molecule of the invention encodes a TANGO 195 polypeptide which lacks both a transmembrane and a cytoplasmic domain.

In another embodiment, a TANGO 195 polypeptide lacks both a transmembrane domain and a cytoplasmic domain and is soluble under physiological conditions.

In another embodiment, a nucleic acid molecule of the invention encodes a TANGO 195 polypeptide which lacks both a transmembrane domain and a cytoplasmic domain and is soluble under physiological conditions.

The polypeptides of the present invention, or biologically active portions thereof, can be operably linked to a heterologous amino acid sequence to form a fusion protein. The invention further features antibodies that specifically bind a polypeptide of the invention such as monoclonal or polyclonal antibodies. In addition, the polypeptides of the invention or biologically active portions thereof can be incorporated into pharmaceutical compositions, which optionally include pharmaceutically acceptable carriers.

In another aspect, the present invention provides methods for detecting the presence of the activity or expression of a polypeptide of the invention in a biological sample by contacting the biological sample with an agent capable of detecting an indicator of activity such that the presence of activity is detected in the biological sample.

In another aspect, the invention provides methods for modulating activity of a polypeptide of the invention comprising contacting a cell with an agent that modulates (inhibits or stimulates) the activity or expression of a polypeptide of the invention such that activity or expression in the cell is modulated. In one embodiment, the agent is an antibody that specifically binds to a polypeptide of the invention. In another embodiment, the agent is a fragment of a polypeptide of the invention or a nucleic acid molecule encoding such a polypeptide fragment.

In another embodiment, the agent modulates expression of a polypeptide of the invention by modulating transcription, splicing, or translation of an mRNA encoding a polypeptide of the invention. In yet another embodiment, the agent is a nucleic acid molecule having a nucleotide sequence that is antisense to the coding strand of an mRNA encoding a polypeptide of the invention.

The present invention also provides methods for treating a subject having a disorder characterized by aberrant activity of a polypeptide of the invention or aberrant expression of a nucleic acid or polypeptide of the invention by administering an agent which is a modulator of the activity of a polypeptide of the invention or a modulator of the expression of a nucleic acid or polypeptide of the invention to the subject. In one embodiment, the modulator is a protein of the invention. In another embodiment, the modulator is an antibody that binds to a polypeptide of the invention. In still another embodiment, the modulator is a nucleic acid of the invention. In other embodiments, the modulator is a peptide, peptidomimetic, or other small molecule.

The present invention also provides diagnostic assays for identifying the presence or absence of a genetic lesion or mutation characterized by at least one of: (i) aberrant modification or mutation of a gene encoding a polypeptide of the invention, (ii) mis-regulation of a gene encoding a polypeptide of the invention, and (iii) aberrant post-translational modification of a protein of the invention wherein a wild-type form of the gene encodes a protein having the activity of the protein of the invention.

In another aspect, the invention provides a method for identifying a compound that binds to or modulates the activity of a polypeptide of the invention. In general, such methods entail measuring a biological activity of the polypeptide in the presence and absence of a test compound and identifying those compounds which alter the activity of the polypeptide.

The invention also features methods for identifying a compound which modulates the expression of a polypeptide or nucleic acid of the invention by measuring the expression of the polypeptide or nucleic acid in the presence and absence of the compound.

Other features and advantages of the invention will be apparent from the following detailed description and claims.

BRIEF DESCRIPTION OF THE DRAWINGS

FIGS. 1A–1B depict the cDNA sequence (SEQ ID NO:1) and predicted amino acid sequence (SEQ ID NO:2) of human TANGO 191. The open reading frame of SEQ ID NO:1 extends from nucleotide 557 to 2353, inclusive (SEQ ID NO:3).

FIG. 3 depicts the cDNA sequence (SEQ ID NO:4) and predicted amino acid sequence (SEQ ID NO:5) of a partial human TANGO 195 clone (form 1). The open reading frame of SEQ ID NO:4 extends from nucleotide 166 to 1101, inclusive (SEQ ID NO:6).

FIG. 5 depicts an alignment of the amino acid sequences of human TANGO 195 (form 1)(SEQ ID NO:5) and human signaling lymphocyte activation molecule ("SLAM")(also known as CD150)(Accession Number U33017)(SEQ ID NO:20). In this alignment the sequences are 22.8% identical overall.

FIG. 6 depicts an alignment of portions of TANGO 191 with PF00047, an IG superfamily domain HMM (SEQ ID NOs:21, 22, and 23).

FIGS. 7A–7B depict the cDNA sequence (SEQ ID NO:24) and predicted amino acid sequence (SEQ ID NO:25) of murine TANGO 195 (Atmue9f11). The open reading frame of SEQ ID NO:24 extends from nucleotide 43 to 876, inclusive (SEQ ID NO:26).

FIG. 8 depicts the cDNA sequence (SEQ ID NO:36) and predicted amino acid sequence (SEQ ID NO:37) of a partial human TANGO 195 clone (Athpb93f1)(form 2). The open reading frame of SEQ ID NO:36 extends from nucleotide 159 to 1118, inclusive (SEQ ID NO:38).

FIGS. 9A–9B depict the cDNA sequence (SEQ ID NO:44) and predicted amino acid sequence (SEQ ID NO:45) of a full length TANGO 195 clone (AthLa170f10). The open reading frame of SEQ ID NO:44 extends from nucleotide 25 to nucleotide 879, inclusive (SEQ ID NO:46).

FIG. 10 depicts a multiple protein sequence alignment between full length TANGO 195 (top sequence, residues 1–285 (SEQ ID NO:45)), TANGO 195 form 2 (middle sequence, residues 1–320 (SEQ ID NO:37)), and TANGO 195 form 1 (bottom sequence, residues 1–312 (SEQ ID NO:5)).

DETAILED DESCRIPTION OF THE INVENTION

Figure 2:
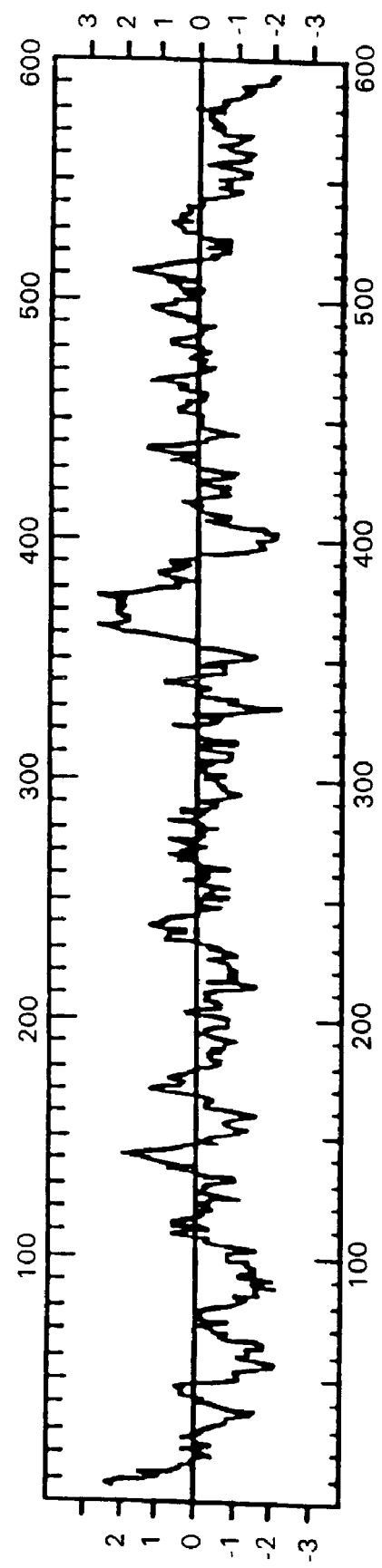
FIG. 2 is a hydropathy plot of TANGO 191. Relative hydrophobicity is shown above the line marked "0", and relative hydrophilicity is shown below the line marked "0". The numbers on the X axis of the figure correspond to residues of the TANGO 191 protein.

The present invention is based on the discovery of cDNA molecules encoding TANGO 191 and TANGO 195, both of which are transmembrane proteins. The subsections and tables summarize certain features of TANGO 191 and TANGO 195.

TANGO 191

The human TANGO 191 cDNA of SEQ ID NO:1 has a 1797 nucleotide open reading frame (SEQ ID NO:3) encoding a 599 amino acid protein (SEQ ID NO:2). The cDNA and protein sequences of human TANGO 191 are shown in FIG. 1. This cDNA was isolated from a human mixed lymphocyte reaction library based on its sequence similarity to genes encoding certain members of the interleukin-1 (IL-1) receptor superfamily.

Human TANGO 191 is a transmembrane protein having a 19 amino acid signal sequence (amino acids 1–19 of SEQ ID NO:2; SEQ ID NO:7) followed by a 580 amino acid mature protein (amino acids 20–599 of SEQ ID NO:2; SEQ ID NO:8). Mature TANGO 191 is predicted to have a transmembrane domain that extends from amino acid 358 to amino acid 382 of SEQ ID NO:2 (SEQ ID NO:10), an extracellular domain that extends from amino acid 20 to amino acid 357 of SEQ ID NO:2 (SEQ ID NO:9), and a cytoplasmic domain extending from amino acid 383 to amino acid 599 of SEQ ID NO:2 (SEQ ID NO:11).

TANGO 191 has a molecular weight of 68.3 kDa prior to cleavage of its signal peptide and a molecular weight of 66.1 kDa after cleavage of its signal peptide.

TANGO 191 has four potential N-glycosylation sites (amino acids 21–24, 119–122, 152–155, and 345–248 of SEQ ID NO:2); 15 potential protein kinase C phosphorylation sites (amino acids 26–28, 35–37, 63–65, 160–162, 203–205, 233–235, 272–275, 307–309, 311–313, 327–329, 474–476, 506–508, 538–540, 575–577, and 590–592 of SEQ ID NO:2); 12 potential casein kinase II phosphorylation sites (amino acids 36–39, 89–92, 133–136, 224–227, 294–297, 301–304, 311–314, 327–330, 401–404, 427–430, 490–493, and 585–588 of SEQ ID NO:2); one potential tyrosine kinase phosphorylation site (amino acids 205–212 of SEQ ID NO:2); and six potential N-myristoylation sites (amino acids 117–122, 168–173, 217–222, 366–371, 460–465, and 583–588 of SEQ ID NO:2).

FIG. 2 is a hydropathy plot of TANGO 191. Relative hydrophobicity is shown above the line marked "0", and relative hydrophilicity is shown below the line marked "0". The numbers on the X axis of the figure correspond to residues of the TANGO 191 protein.

Northern analysis of human TANGO 191 mRNA expression revealed that it is expressed in spleen, lymph node, peripheral blood lymphocytes, and bone marrow.

A clone (EPftX 191 a) containing a cDNA encoding TANGO 191 inserted into pZL-1 (GIBCO/BRL; Bethesda, MD) between the NotI and SalI sites was deposited with the American Type Culture Collection, Manassas, Va. on Sep. 9, 1998, and assigned Accession Number 98881.

Human TANGO 191 appears to be a member of the IL-I receptor superfamily. TANGO 191 includes three regions (amino acids 71–128 of SEQ ID NO:2; SEQ ID NO:17); amino acids 168–223 of SEQ ID NO:2; SEQ ID NO:18); amino acids 266–339 of SEQ ID NO:2; SEQ ID NO: 19) which have homology to the IG superfamily domain (PF00047) that is characteristic of members of the IL-1 superfamily (FIG. 6).

IL-1 receptor (IL-1R) plays a critical role the regulation of immune and inflammatory responses. Signaling by IL-1R requires that IL-1R form a complex with IL-1AcP, a protein which may be required for internalization of IL-1R. It is thought that both IL-1R and IL-1AcP interact with IRAK-2. It has been proposed that this multiprotein complex interacts with TRAF6, which engages a protein complex that acts to activate NF-$_\kappa$B. Members of the NF-$_\kappa$B family regulate many of immune and inflammatory genes that are induced by IL-1.

Uses of TANGO 191 Nucleic acids, Polypeptides, and Modulators Thereof

Since TANGO 191 has some similarity to IL-1 receptor, TANGO 191 nucleic acids and polypeptides as well as modulators of TANGO 191 expression or activity are useful in the treatment of a variety of immune and inflammatory disorders, e.g., asthma, graft vs-host disease, rheumatoid arthritis, psoriasis, inflammatory bowel disease (e.g., ulcerative colitis, Crohn's disease), septic shock, chronic myelogenous leukemia, cancer, liver disease, Hodgkin's disease, osteoarthritis, Lyme disease, cachexia, and autoimmune diseases, e.g., myasthenia gravis, autoimmune diabetes, and lupus.

Human TANGO 195

The present invention includes three versions of TANGO 195: two partial cDNA and proteins ("form 1" and "form 2"), and a full length version ("full length TANGO 195"). Although forms 1 and 2 are longer than full length TANGO 195, forms 1 and 2 are referred to as partial sequences because their cDNAs do not contain an open reading frame that ends with a traditional stop codon, followed by 3' untranslated sequence.

As seen in FIG. 10, the protein sequences of all three TANGO 195 forms are identical from residues 1–261. At this point, full length TANGO 195 ends (full length TANGO 195 cDNA encodes a stop codon), and TANGO 195 forms 1 and 2 continue (i.e., there is more protein sequence C-terminal to residue 261). TANGO 195 forms 1 and 2 are identical from residues 1–306, after which they diverge. TANGO 195 form 1 is different from TANGO 195 form 2 from residues 307–312 (form I ends at residue 312), and TANGO 195 form 2 is different from TANGO 195 form 2 from residues 307–320 (form 2 ends at residue 320).

The human TANGO 195 (form 1) partial cDNA of SEQ ID NO:4 has a 936 nucleotide open reading frame (SEQ ID NO:6) encoding a 312 amino acid protein (SEQ ID NO:5). The cDNA and protein sequences of human TANGO 195 (form 1) clone are shown in FIG. 3. This partial TANGO 195 cDNA clone was isolated from a human mixed lymphocyte reaction library based on its homology to signaling lymphocyte activation marker (SLAM)(Cocks et al. (1995) *Nature* 376:260–63). Apparent full-length clones (3.0 kb and 1.3 kb) were isolated from the same library and a human pancreas library.

The portion of human TANGO 195 (form 1) encoded by the cDNA of SEQ ID NO:4 is a transmembrane protein having a 22 amino acid signal sequence (amino acids 1–22 of SEQ ID NO:5; SEQ ID NO:12) followed by a 290 amino acid mature protein (amino acids 23–312 of SEQ ID NO:5; SEQ ID NO:13). The portion of mature TANGO 195 (form 1) encoded by the cDNA of SEQ ID NO:4 is predicted to have a transmembrane domain that extends from amino acid 234 to amino acid 254 of SEQ ID NO:5 (SEQ ID NO:15), an extracellular domain that extends from amino acid 23 to amino acid 233 of SEQ ID NO:5 (SEQ ID NO:14), and a cytoplasmic domain extending from amino acid 255 to amino acid 312 of SEQ ID NO:5 (SEQ ID NO:16).

Partial TANGO 195 (form 1) has a molecular weight of 34.8 kDa prior to cleavage of its signal peptide and a molecular weight of 32.3 kDa after cleavage of its signal peptide.

The TANGO 195 of SEQ ID NO:5 (form 1) has three potential N-glycosylation sites (amino acids 85–88, 100–103, and 156–159 of SEQ ID NO:5); three potential protein kinase C phosphorylation sites (amino acids 163–165, 230–232, and 308–310 of SEQ ID NO:5); three potential casein kinase II phosphorylation sites (amino acids 168–171, 215–218, and 230–233 of SEQ ID NO:5); one potential tyrosine kinase phosphorylation site (amino acids 65–72 of SEQ ID NO:5); one potential cGMP-dependent protein kinase phosphorylation site (amino acids 165–168 of SEQ ID NO:5); and three potential N-myristoylation sites (amino acids 66–71, 110–115, and 183–188 of SEQ ID NO:5).

The human TANGO 195 (form 2) partial cDNA of SEQ ID NO:36 has a 960 nucleotide open reading frame (SEQ ID NO:38) encoding a 320 amino acid protein (SEQ ID NO:37). The cDNA and protein sequences of human TANGO 195 (form 2) clone are shown in FIG. 8. This partial TANGO 195 cDNA clone (jthpb93f1) was isolated from a human pancreas library.

The portion of human TANGO 195 (form 2) encoded by the cDNA of SEQ ID NO:36 is a transmembrane protein having a 22 amino acid signal sequence (amino acids 1–22 of SEQ ID NO:37; SEQ ID NO:39) followed by a 298 amino acid mature protein (amino acids 23–320 of SEQ ID NO:37; SEQ ID NO:40). The portion of mature TANGO 195 (form 2) encoded by the cDNA of SEQ ID NO:36 is predicted to have a transmembrane domain that extends from amino acid 234 to amino acid 254 of SEQ ID NO:37 (SEQ ID NO:42), an extracellular domain that extends from amino acid 23 to amino acid 233 of SEQ ID NO:37 (SEQ ID NO:41), and a cytoplasmic domain extending from amino acid 255 to amino acid 320 of SEQ ID NO:37 (SEQ ID NO:43).

Partial TANGO 195 (form 2) has a molecular weight of 35.8 kDa prior to cleavage of its signal peptide and a molecular weight of 33.3 kDa after cleavage of its signal peptide.

The TANGO 195 of SEQ ID NO:37 (form 2) has three potential N-glycosylation sites (amino acids 85–88, 100–103, and 156–159 of SEQ ID NO:37); two potential protein kinase C phosphorylation sites (amino acids 163–165 and 230–232 of SEQ ID NO:37); three potential casein kinase II phosphorylation sites (amino acids 168–171, 215–218, and 230–233 of SEQ ID NO:37); one potential tyrosine kinase phosphorylation site (amino acids 65–72 of SEQ ID NO:37); one potential cGMP-dependent protein kinase phosphorylation site (amino acids 165–168 of SEQ ID NO:37); and three potential N-myristoylation sites (amino acids 66–71, 110–115, and 183–188 of SEQ ID NO:37).

The human TANGO 195 full length cDNA of SEQ ID NO:44 has a 855 nucleotide open reading frame (SEQ ID NO:46) encoding a 285 amino acid protein (SEQ ID NO:45). The cDNA and protein sequences of full length human TANGO 195 clone are shown in FIG. 9. This full length TANGO 195 cDNA clone (jthLa170f10) was isolated from a human mixed lymphocyte reaction library.

The full-length TANGO 195 protein of FIG. 9 is predicted to be a transmembrane protein having a 22 amino acid signal sequence (amino acids 1–22 of SEQ ID NO:45; SEQ ID NO:47) followed by a 263 amino acid mature protein (amino acids 23–285 of SEQ ID NO:45; SEQ ID NO:48). This form of TANGO 195 is predicted to have a transmembrane domain extending from amino acid 234 to amino acid 254 of SEQ ID NO:45 (SEQ ID NO:50), an extracellular domain extending from amino acid 23 to amino acid 233 of SEQ ID NO:45 (SEQ ID NO:49) and a cytoplasmic domain that extends from amino acid 255 to amino acid 285 of SEQ ID NO:45 (SEQ ID NO:51).

Full length TANGO 195 has a molecular weight of 31.7 kDa prior to cleavage of its signal peptide and a molecular weight of 29.2 kDa after cleavage of its signal peptide.

The full length TANGO 195 of SEQ ID NO:45 has three potential N-glycosylation sites (amino acid 85–88, 100–103, and 156–159 of SEQ ID NO:45); three potential protein kinase C phosphorylation sites (amino acids 163–165, 230–232, and 260–262 of SEQ ID NO:45); three potential casein kinase II phosphorylation sites (amino acids 168–171, 215–218, and 230–233 of SEQ ID NO:45); one potential tyrosine kinase phosphorylation site (amino acids 65–72 of SEQ ID NO:45); one potential cGMP-dependent protein kinase phosphorylation site (amino acids 165–168 of SEQ ID NO:45); and three potential N-myristoylation sites (amino acids 66–71, 110–115, and 183–188 of SEQ ID NO:45).

TANGO 195 is a type I transmembrane protein belonging to the CD2 subgroup of the immunoglobulin superfamily. The CD2 family is a subset of the immunoglobulin supergene superfamily (IgSF), and its members function as co-receptors for lymphocyte activation and/or adhesion. (Tangye, S. G. et al. (2000) *Seminars In Immunology* 12(2): 149–57).

Clustal analysis of the human CD2 family shows TANGO 195 to be most closely related to CD48. Comparison of the extracellular domain of the mature full length TANGO 195 protein (without the signal peptide or the extracellular and intracellular domains) shows TANGO 195 to be most closely related to CD58.

Human TANGO 195 includes immunoglobulin domains in its extracellular domain that are characteristic of members of the CD2 family. Full length TANGO 195 has an immunoglobulin IG_3c (C2) domain (from amino acids 22–122 of SEQ ID NO:5, 37, and 45 (SEQ ID NO:34)) and an IG domain (from amino acids 145–203 of SEQ ID NO:5, 37, and 45 (SEQ ID NO:35)).

TANGO 195 has regions that are significantly similar to human signaling lymphocyte activation molecule ("SLA-M")(also known as CD150)(Accession Number U33017). For example, the region of TANGO 195 from amino acid 173 to amino acid 250 has 32% identity (25/78 amino acids) and 50% identity (39/59 amino acids) to the corresponding region of SLAM; the region of TANGO 195 from amino acid 134 to amino acid 164 has 32% identity (10/31 amino acids) and 41% identity (13/31 amino acids) to the corresponding region of SLAM; and the region of TANGO 195 from amino acid 117 to amino acid 132 has 43% identity (7/16 amino acids) and 75% identity (12/16 amino acids) to the corresponding region of SLAM (FIG. 5).

SLAM is thought to enhance the expansion and differentiation of activated B cells (Punnonen et al. (1997) *J. Exp. Med.* 185:993–1004) and in the regulation of type 1 and type 2 cytokine production (Ferrante et al. (1998) *J. Immunology* 160:1514–21). TANGO 195 likely has a function similar to that of SLAM. Thus, modulators of TANGO 195 expression or activity may be useful in the treatment of disorders associated with aberrant B cell expansion or differentiation or aberrant cytokine production, e.g., allergic and autoimmune disorders.

Figure 4:
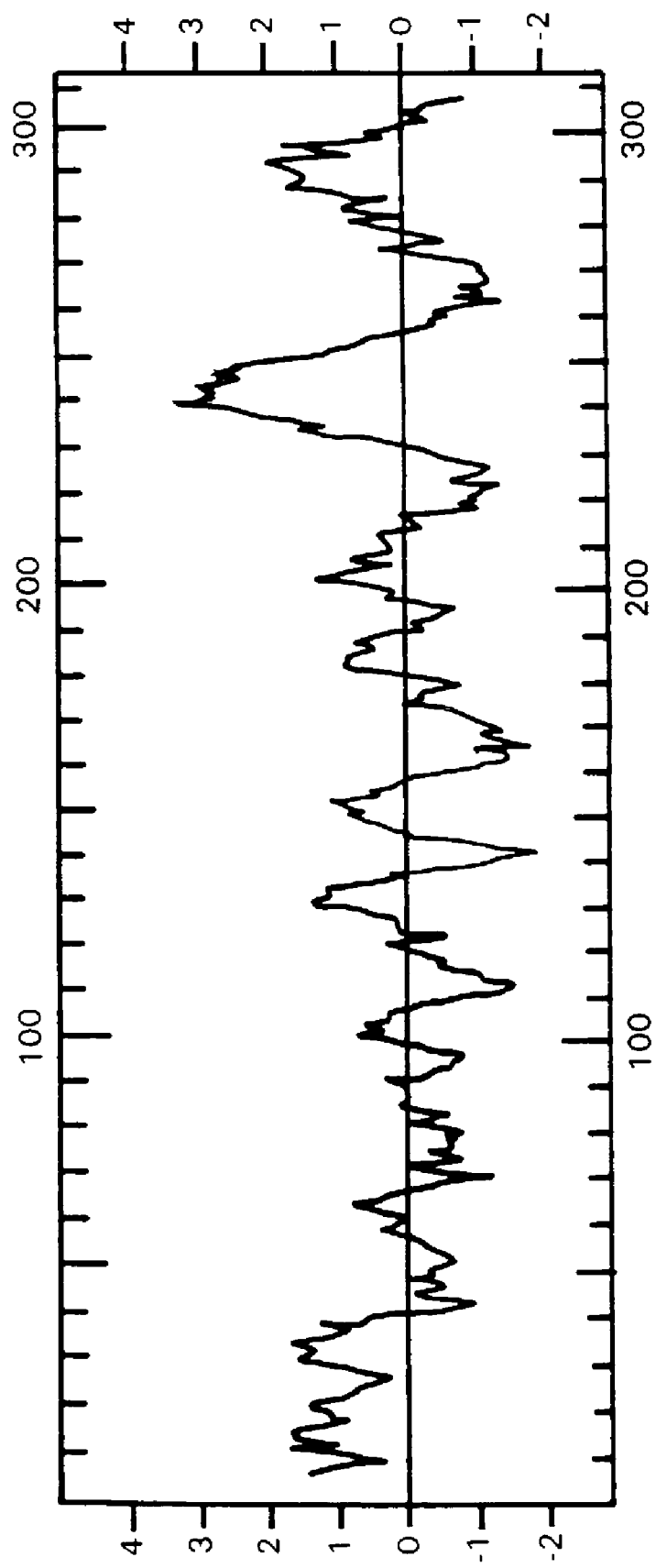
FIG. 4 is a hydropathy plot of TANGO 195 (form 1). Relative hydrophobicity is shown above the line marked "0", and relative hydrophilicity is shown below the line marked "0". The numbers on the X axis of the figure correspond to residues of the TANGO 195 protein.

FIG. 4 is a hydropathy plot of the TANGO 195 of SEQ ID NO:5 (form 1). Relative hydrophobicity is shown above the line marked "0", and relative hydrophilicity is shown below the line marked "0". The numbers of the X axis of the figure correspond to residues of the TANGO 195 protein.

FIG. 8 depicts the cDNA sequence (SEQ ID NO:36) and predicted amino acid sequence (SEQ ID NO:37) of a partial human TANGO 195 clone (form 2). The open reading frame extends from nucleotide 159 to 1118, inclusive (SEQ ID NO:38).

FIG. 9 depicts the cDNA sequence (SEQ ID NO:44) and predicted amino acid sequence (SEQ ID NO:45) of a full length TANGO 195 clone (T195AthLa170f10). The open reading frame extends from nucleotide 25 to nucleotide 879, inclusive (SEQ ID NO:46).

A clone (EpjthPb0930f01) containing a 1.3 kb cDNA encoding TANGO 195 (form 2) in pMET7 between NotI and SalI was deposited with the American Type Culture Collection, Manassas, Va. on Sep. 9, 1998, and assigned Accession Number 98882.

Northern analysis of TANGO 195 expression revealed the presence of a 1.8 kb transcript and a 3.4 kb transcript in spleen, lymph node and thymus, and a 1.8 kb transcript in bone marrow with expression being highest in lymph node. Additional Northern analysis revealed expression in the following tissues (in decreasing order of expression): lymph node, stomach, small intestine, appendix, lung, spleen, and bone marrow.

Additional Northern analysis revealed that TANGO 195 is expressed in activated human monocytes/macrophages and, at lower level, in activated human lymphocytes. This analysis also revealed that cytokine induced differentiation of T cells appears to regulate TANGO 195 expression. Taqman analysis reveals significant expression in unpurified PBMCs, monocytes and certain dendritic cells. T195 therefore is expressed on at least 2 populations of professional antigen presenting cells: activated monocytes and dendritic cells.

TANGO 195 maps to human chromosome locus hu1q21. The flanking markers are AFMA323ZE5 and D1S2635. The among identified loci in close proximity to TANGO 195 are HYPLP1 (hyperlipidemial) and LPD1 (lipodystrophy). Nearby known human genes include: SPTA1 (spectrin, alpha), THBS3 (thrombospondin 3), MTX (metaxin), CTSS (cathepsin K,S), FLG (filaggrin), PKLR (pyruvate kinase), HYPLIP 1 (hyperlipidemia).

Also mapping to the hu1 q21–23 region are the orphan receptors CD84 and Ly9. As it has been shown that ligand/receptor pairs within the CD2 family are genetically linked, TANGO 195 can be the ligand for either of these receptors (Sewell, W. A., et al. (1988) *Immunogenetics* 28(4):278–82)(Kingsmore, S. F., et al. (1989) *Immunogenetics* 30(2): 123–5).

The mouse chromosome corresponding to human chromosomal locus hu1q2l is chromosome 3. Nearby mouse loci include: soc (soft coat), hyplipI (hyperlipidemia), ft (flaky tail) and ma (matted). Nearby mapped mouse genes include: Imna (lamin A), fig (filaggrin), bcan (brevican), gba (acid beta glucosidase).

Rabbit polyclonal antibodies were raised against three peptides from murine TANGO 195. These peptides include amino acids 26–34 of SEQ ID NO:25 (KVGDSELLV, SEQ ID NO:52), 102–117 of SEQ ID NO:25 (LMVDTRGQTWTQTLYL, SEQ ID NO:53) and 161–176 of SEQ ID NO:25 (SWRREGTVDFNGEVHS, SEQ ID NO:54). Peptide purified sera from rabbits immunized with amino acids 102–117 (SEQ ID NO:53) specifically recognizes mouse TANGO 195-hFc protein by standard Western Blot. Additionally unpurified sera from rabbits immunized with amino acids 102–117 (SEQ ID NO:53) recognize mouse T195-hFc by ELISA. ELISA plates were coated with 5 Tg/ml mouse T195-hFc or human Ig control in PBS overnight at 4° C. Plates were washed and blocked with PBS 1% PSA. Serial dilutions of serum were added and incubated for approximately 2 hours at room temperature. Plates were washed and rabbit immunoglobulin detected with anti-rabbit Ig-HRP. Serum from rabbits immunized with the peptide corresponding to amino acids 102–117 showed greater than 20 fold higher titers against mouse TANGO 195-hFc compared to human Ig, and showed greater than 20 fold higher titers against mouse TANGO 195-hFc compared to control serum.

Several TANGO 195/immunoglobulin constant region fusion proteins were created. Using human TANGO 195 a fusion protein consisting of TANGO 195 (amino acids 1–233)-AAPGGASYKD-human IgG1fc was created (SEQ ID NO:55). A second human TANGO 195 fusion substituted murine IgG1fc for human IgG1fc. Using murine TANGO 195 a fusion protein consisting of TANGO 195 (amino acids 1 to 23 1)-AASGKASYKD-human IgG1fc (SEQ ID NO:56) was created. A second murine TANGO 195 fusion protein substituted murine IgG1fc for human IgG1fc.

Murine TANGO 195

The murine TANGO 195 cDNA of SEQ ID NO:24 has a 834 nucleotide open reading frame (SEQ ID NO:26) encoding a 278 amino acid protein (SEQ ID NO:25). The cDNA and protein sequences of murine TANGO 195 clone are shown in FIG. 7. The murine TANGO 195 cDNA clone (jtmnue9f11) was isolated from a murine lung library.

The portion of murine TANGO 195 encoded by the cDNA of SEQ ID NO:24 is a transmembrane protein having a 20 amino acid signal sequence (amino acids 1–20 of SEQ ID NO:25; SEQ ID NO:27) followed by a 258 amino acid mature protein (amino acids 21–278 of SEQ ID NO:25; SEQ ID NO:28). The portion of mature murine TANGO 195 encoded by the cDNA of SEQ ID NO:24 is predicted to have a transmembrane domain that extends from amino acid 232 to amino acid 252 of SEQ ID NO:25 (SEQ ID NO:30), an extracellular domain that extends from amino acid 21 to amino acid 231 of SEQ ID NO:25 (SEQ ID NO:29), and a cytoplasmic domain extending from amino acid 253 to amino acid 278 of SEQ ID NO:25 (SEQ ID NO:31).

Full length murine TANGO 195 has a molecular weight of 30.7 kDa prior to cleavage of its signal peptide and a molecular weight of 28.4 kDa after cleavage of its signal peptide.

The full length murine TANGO 195 of SEQ ID NO:25 has three potential N-glycosylation sites (amino acids 83–86, 98–101, and 154–157 of SEQ ID NO:25); four potential protein kinase C phosphorylation sites (amino acids 161–163, 224–226, 228–230, and 258–260 of SEQ ID NO:25); two potential casein kinase II phosphoiylation sites (amino acids 213–216 and 228–231 of SEQ ID NO:25); one potential tyrosine kinase phosphorylation site (amino acids 63–70 of SEQ ID NO:25); one potential amidation site (amino acids 258–261 of SEQ ID NO:25); and five potential N-myristoylation sites (amino acids 64–69, 108–113, 181–186, 247–252, and 255–260 of SEQ ID NO:25).

Murine TANGO 195 includes immunoglobulin domains in its extracellular domain that are characteristic of members of the CD2 family. Murine TANGO 195 has an immunoglobulin IG_3c (C2) domain (from amino acids 20–120 of SEQ ID NO:25 (SEQ ID NO:32)) and an IG domain (from amino acids 143–201 of SEQ ID NO:25 (SEQ ID NO:33)).

FIG. 7 depicts the cDNA sequence (SEQ ID NO:24) and predicted amino acid sequence (SEQ ID NO:25) of murine TANGO 195. The open reading frame of SEQ ID NO:24 extends from nucleotide 43 to 876, inclusive (SEQ ID NO:26). Murine TANGO 195 shows 75% identity at the amino acid level with full length TANGO 195.

In situ expression analysis of TANGO 195 in adult mice revealed expression in the spleen (mutlifocal expression with expression highest in follicles), thymus (multifocal expression), and lymph node (multifocal expression). No expression was detected in lung and stomach. In situ expression analysis was also used to examine expression in the spleens of adult mice 1, 3, 5, and 14 post-immunization with EFA/PBS. In each case multifocal expression was observed with expression being highest in the follicles. The expression at 14 days post-immunization was somewhat lower than in at other time points.

Uses of TANGO 195 Nucleic acids, Polypeptides, and Modulators Thereof

As TANGO 195 clone form 2 was derived from a pancreas library, TANGO 195 polypeptides, nucleic acids, and modulators thereof can be used to modulate the proliferation, differentiation, and/or function of cells that form the pancreas, e.g., from the islets of Langerhans, e.g., acinar cells and centroacinar cells. Thus TANGO 195 polypeptides, nucleic acids, and modulators thereof can be used to treat pancreatic disorders, such as pancreatitis (e.g., acute hemorrhagic pancreatitis and chronic pancreatitis), pancreatic cysts (e.g., congenital cysts, pseudocysts, and benign or malignant neoplastic cysts), pancreatic tumors (e.g., pancreatic carcinoma and adenoma), diabetes mellitus (e.g., insulin- and non-insulin-dependent types, impaired glucose tolerance, and gestational diabetes), or islet cell tumors (e.g., insulinomas, adenomas, Zollinger-Ellison syndrome (gastrinoma), glucagonomas, and somatostatinoma).

As murine TANGO 195 was derived from a murine lung library, and as TANGO 195 has exhibited expression in lung, TANGO 195 polypeptides, nucleic acids, and modulators thereof can be used to modulate the proliferation, differentiation, and/or function of cells that form the lungs, e.g., form the alveoli (e.g., squamous alveolar cells and/or great alveolar cells) or the pulmonary circulatory system (e.g., pulmonary endothelial cells). Thus TANGO 195 polypeptides, nucleic acids, and modulators thereof can be used to treat pulmonary (lung) disorders, such as atelectasis, cystic fibrosis, rheumatoid lung disease, pulmonary congestion or edema, chronic obstructive airway disease (e.g., emphysema, chronic bronchitis, bronchial asthma, and bronchiectasis), diffuse interstitial diseases (e.g., sarcoidosis, pneumoconiosis, hypersensitivity pneumonitis, bronchiolitis, Goodpasture s syndrome, idiopathic pulmonary fibrosis, idiopathic pulmonary hemosiderosis, pulmonary alveolar proteinosis, desquamative interstitial pneumonitis, chronic interstitial pneumonia, fibrosing alveolitis, hamman-rich syndrome, pulmonary eosinophilia, diffuse interstitial fibrosis, Wegener's granulomatosis, lymphomatoid granulomatosis, and lipid pneumonia), or tumors (e.g., bronchogenic carcinoma, bronchioloviveolar carcinoma, bronchial carcinoid, hamartoma, and mesenchymal tumors).

As expression data showed TANGO 195 expression in spleen, TANGO 195 polypeptides, nucleic acids, and modulators thereof can be used to modulate the proliferation, differentiation, and/or function of cells that form the spleen, e.g., cells of the splenic connective tissue, e.g., splenic smooth muscle cells and/or endothelial cells of the splenic blood vessels. TANGO 195 polypeptides, nucleic acids, and modulators thereof can also be used to modulate the proliferation, differentiation, and/or function of cells that are processed, e.g., regenerated or phagocytized within the spleen, e.g., erythrocytes and/or B and T lymphocytes and macrophages. Thus TANGO 195 polypeptides, nucleic acids, and modulators thereof can be used to treat spleen associated diseases and disorders. Examples of splenic diseases and disorders include e.g., splenic lymphoma and/or splenomegaly, and/or phagocytotic disorders, e.g., those inhibiting macrophage engulfment of bacteria and viruses in the bloodstream.

As expression data showed TANGO 195 expression in small intestine, TANGO 195 polypeptides, nucleic acids, and modulators thereof can be used to modulate the proliferation, differentiation, and/or function of cells that form the small intestine, e.g., absorptive epithelial cells, Goblet cells, and/or Penth's cells. Thus TANGO 195 polypeptides, nucleic acids, and modulators thereof can be used to treat intestinal disorders, such as ischemic bowel disease, duodenal ulcers, infective enterocolitis, Crohn's disease, benign tumors, malignant tumors (e.g., argentaffinomas, lymphomas, adenocarcinomas, and sarcomas), malabsorption syndromes (e.g., celiac disease, tropical sprue, Whipple's disease, and abetalipoproteinemia), obstructive lesions, hernias, intestinal adhesions, intussusception, or volvulus.

As expression data showed TANGO 195 expression in the stomach (as well as in the small intestine), TANGO 195 polypeptides, nucleic acids, and modulators thereof can be used to modulate the proliferation, differentiation, and/or function of cells that form the stomach, e.g., chief (zymogenic) cells, enteroendocrine cells, and oxyntic (parietal) cells. Thus TANGO 195 polypeptides, nucleic acids, and modulators thereof can be used to treat gastrointestinal disorders. Gastrointestinal disorders include gastrointestinal tumors (e.g., gastric adenocarcinoma, primary gastric lymphoma, gastric sarcoma), peptic and gastric ulcers, gastritis (inflammation of the gastric mucosa (e.g., type A gastritis (autoimmune chronic atrophic gastritis) and type B gastritis (environmental gastritis)), Ménétrier's disease, gastrinemia, absorption disorders (e.g., diarrhea, irritable bowel syndrome, diabetes mellitus), inflammatory bowel disease, ischemic bowel disease, infective enterocolitis, Crohn's disease, and ulcerative colitis.

As expression data showed TANGO 195 expression in bone marrow, TANGO 195 polypeptides, nucleic acids, and modulators thereof can be used to modulate the proliferation, differentiation, and/or function of cells that appear in the bone marrow, e.g., stem cells (e.g., hematopoietic stem cells), and blood cells, e.g., erythrocytes, platelets, and leukocytes. Thus TANGO 195 polypeptides, nucleic acids, and modulators thereof can be used to treat bone marrow, blood, and hematopoietic associated diseases and disorders, e.g., acute myeloid leukemia, hemophilia, leukemia, anemia (e.g., sickle cell anemia), and thalassemia.

Other hematological disorders include, but are not limited to, disorders associated with abnormal differentiation or hematopoiesis, morphology, migration, proliferation, or function of blood cells derived, for example, from myeloid multipotential cells in bone marrow, such as megakaryocytes (and ultimately platelets), monocytes, erythroids, and granulocytes (e.g., neutrophils, eosinophils, and basophils), and from lymphoid multipotential cells, such as T and B lymphocytes.

Furthermore, as expression data showed TANGO 195 expression in monocytes and macrophages, TANGO 195 polypeptides, nucleic acids, and modulators thereof can be used to modulate the proliferation, differentiation, and/or function of said cells. Therefore, TANGO 195 polypeptides, nucleic acids, and modulators thereof can be used play a role in monocyte and/or macrophage associated disorders.

Monocyte associated disorders include disorders associated with abnormal monocyte and/or macrophage function, such as impaired phagocytosis, chemotaxis, or secretion of cytokines, growth factors and acute-phase reactants, resulting from certain diseases, e.g., lysosomal storage diseases (e.g., Gaucher's disease); impaired monocyte cytokine production, for example, found in some patients with disseminated nontuberculous mycobacterial infection who are not infected with HIV; leukocyte adhesion deficiency (LAD), hyperimmunoglobulin E-recurrent infection (HIE) or Job's syndrome, Chédiak-Higashi syndrome (CHS), and chronic granulomatous diseases (CGD), certain autoimmune diseases, such as systemic lupus erythematosus and other autoimmune diseases characterized by tissue deposition of immune complexes, as seen in Sjögren's syndrome, mixed cryoglobulinemia, dermatitis herpetiformis, and chronic progressive multiple sclerosis. Also included are disorders or infections that impair mononuclear phagocyte function, for example, influenza virus infection and AIDS.

Monocyte associated disorders also include monocytoses such as, for example, monocytoses associated with certain infections such as tuberculosis, brucellosis, subacute bacterial endocarditis, Rocky Mountain spotted fever, malaria, and visceral leishmaniasis (kala azar), in malignancies, leukemias (e.g., acute myeloid leukemia), myeloproliferative syndromes, hemolytic anemias, chronic idiopathic neutropenias, and granulomatous diseases such as sarcoidosis, regional enteritis, and some collagen vascular diseases.

Other monocyte associated disorders include monocytopenias such as, for example, monocytopenias that can occur with acute infections, with stress, following administration of glucocorticoids, aplastic anemia, hairy cell leukemia, and acute myelogenous leukemia and as a direct result of administration of myelotoxic and immunosuppressive drugs.

As TANGO 195 clones (form 1 and full length TANGO 195) were derived from a mixed lymphocyte reaction library; as TANGO 195 has exhibited expression in lymph nodes, thymus, lymphocytes, and dendritic cells; and as CD2 family members function as co-receptors for lymphocyte activation and/or adhesion, TANGO 195 polypeptides, nucleic acids, and modulators thereof can be used to modulate the proliferation, differentiation, and/or function of lymphocytes, e.g., B cells and T cells. Thus TANGO 195 polypeptides, nucleic acids, and modulators thereof play a role in lymphocyte disorders.

Lymphocyte disorders include, e.g., lymphoid leukemias and non-Hodgkin's lymphomas (e.g., granular lymphocytic leukemia, hairy cell leukemia, Burkitt's lymphoma), Hodgkin's disease, and lymphoid neoplasms. B cell specific disorders include lymphoproliferative disorders, e.g., lymphoid leukemias and non-Hodgkin's lymphomas (e.g., B cell chronic lymphocytic leukemia, diffuse large B cell lymphoma, AIDS-related lymphomas).

T cell specific disorders include T cell autoimmune disorders (e.g., AIDS), T cell inflammatory disorders (e.g., dermatitis), T cell lymphoma (e.g., human T cell leukemia virus (HTLV)), T cell leukemia, and T cell lymphoproliferative disorders (e.g., fibroses (e.g., cystic fibrosis), and lymphoid leukemias and non-Hodgkin's lymphomas (e.g., T cell prolymphocytic leukemia, peripheral T cell leukemia, and T cell chronic lymphocytic leukemia)).

Thus TANGO 195 polypeptides, nucleic acids, and modulators thereof also play a role in immune related disorders, e.g., immunodeficiency disorders (e.g., HIV), viral disorders (e.g., infection by HSV), cell growth disorders, e.g., cancers (e.g., carcinoma, lymphoma, e.g., follicular lymphoma). autoimmune disorders (e.g., arthritis, graft rejection (e.g., allograft rejection), and inflammatory disorders (e.g., bacterial or viral infection, psoriasis, septicemia, cerebral malaria, inflammatory bowel disease, arthritis (e.g., rheumatoid arthritis, osteoarthritis), allergic inflammatory disorders (e.g., asthma, psoriasis)).

TABLE 1

Summary of TANGO 191 and TANGO 195 Sequence Information

| Gene | cDNA | ORF | Protein | FIG. | Accession No. |
|---|---|---|---|---|---|
| Human TANGO 191 | SEQ ID NO: 1 | SEQ ID NO: 3 | SEQ ID NO: 2 | FIG. 1 | 98881 |
| Human TANGO 195 (form 1) | SEQ ID NO: 4 | SEQ ID NO: 6 | SEQ ID NO: 5 | FIG. 2 | 98882 |
| Human TANGO 195 (form 2) | SEQ ID NO: 36 | SEQ ID NO: 38 | SEQ ID NO: 37 | FIG. 8 | — |
| Human TANGO 195 full-length | SEQ ID NO: 44 | SEQ ID NO: 46 | SEQ ID NO: 45 | FIG. 9 | — |
| Murine TANGO 195 | SEQ ID NO: 24 | SEQ ID NO: 26 | SEQ ID NO. 25 | FIG. 7 | — |

TABLE 2

Summary of Domains of TANGO 191 and TANGO 195

| Protein | Signal Sequence | Mature Protein | Extracellular Domain | Transmembrane Domain | Cytoplasmic Domain |
|---|---|---|---|---|---|
| TANGO 191 SEQ ID NO: 2 | aa 1–19 SEQ ID NO: 7 | aa 20–599 SEQ ID NO: 8 | aa 20–357 SEQ ID NO: 9 | aa 358–382 SEQ ID NO: 10 | aa 383–599 SEQ ID NO: 11 |
| Human TANGO 195 (form 1) SEQ ID NO: 5 | aa 1–22 SEQ ID NO: 12 | aa 23–312 SEQ ID NO: 13 | aa 23–233 SEQ ID NO: 14 | aa 234–254 SEQ ID NO: 15 | aa 255–312 SEQ ID NO: 16 |
| Human TANGO 195 (form 2) SEQ ID NO: 37 | aa 1–22 SEQ ID NO: 39 | aa 23–320 SEQ ID NO: 40 | aa 23–233 SEQ ID NO: 41 | aa 234–254 SEQ ID NO: 42 | aa 255–320 SEQ ID NO: 43 |
| Human TANGO 195 full-length SEQ ID NO: 45 | aa 1–22 SEQ ID NO: 47 | aa 23–285 SEQ ID NO: 48 | aa 23–233 SEQ ID NO: 49 | aa 234–254 SEQ ID NO: 50 | aa 255–285 SEQ ID NO: 51 |
| Murine TANGO 195 SEQ ID NO: 25 | aa 1–20 SEQ ID NO: 27 | aa 21–278 SEQ ID NO: 28 | aa 21–231 SEQ ID NO: 29 | aa 232–252 SEQ ID NO: 30 | aa 253–278 SEQ ID NO: 31 |

Various aspects of the invention are described in further detail in the following subsections I. Isolated Nucleic Acid Molecules One aspect of the invention pertains to isolated nucleic acid molecules that encode a polypeptide of the invention or a biologically active portion thereof, as well as nucleic acid molecules sufficient for use as hybridization probes to identify nucleic acid molecules encoding a polypeptide of the invention and fragments of such nucleic acid molecules suitable for use as PCR primers for the amplification or mutation of nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 4, 6, 24, 26, 36, 38, 44, or 46, the cDNA of ATCC 98881, or the cDNA of ATCC 98882, or a complement thereof, can be isolated using standard molecular biology techniques and the sequence information provided herein. Using all or a portion of the nucleic acid sequences of SEQ ID NO:1, 3, 4, 6, 24, 26, 36, 38, 44, or 46, the cDNA of ATCC 98881, or the cDNA of ATCC 98882 as a hybridization probe, nucleic acid molecules of the invention can be isolated using standard hybridization and cloning techniques (e.g., as described in Sambrook et al., eds., *Molecular Cloning: A Laboratory Manual, 2nd ed., Cold Spring Harbor Laboratory,* Cold Spring Harbor Laboratory Press, Cold Spring Harbor, N.Y., 1989).

A nucleic acid molecule of the invention can be amplified using cDNA, mRNA or genomic DNA as a template and appropriate oligonucleotide primers according to standard PCR amplification techniques. The nucleic acid so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

In another preferred embodiment, an isolated nucleic acid molecule of the invention comprises a nucleic acid molecule which is a complement of the nucleotide sequence of SEQ ID NO:1, 3, 4, 6, 24, 26, 36, 38, 44, or 46, the cDNA of ATCC 98881, or the cDNA of ATCC 98882, or a portion thereof. A nucleic acid molecule which is complementary to a given nucleotide sequence is one which is sufficiently complementary to the given nucleotide sequence that it can hybridize to the given nucleotide sequence thereby forming a stable duplex.

Moreover, a nucleic acid molecule of the invention can comprise only a portion of a nucleic acid sequence encoding a full length polypeptide of the invention for example, a fragment which can be used as a probe or primer or a fragment encoding a biologically active portion of a polypeptide of the invention. The nucleotide sequence determined from the cloning one gene allows for the generation of probes and primers designed for use in identifying and/or cloning homologues in other cell types, e.g., from other tissues, as well as homologues from other mammals. The probe/primer typically comprises substantially purified oligonucleotide. The oligonucleotide typically comprises a region of nucleotide sequence that hybridizes under stringent conditions to at least about 12, preferably about 25, more preferably about 50, 75, 100, 125, 150, 175, 200, 250, 300, 350 or 400 consecutive nucleotides of the sense or anti-sense strand of SEQ ID NO:1, 3, 4, 6, 24, 26, 36, 38, 44, or 46, the cDNA ATCC 98881, or the cDNA of ATCC 98882 or of a naturally occurring mutant of SEQ ID NO:1, 3, 4, 6, 24, 26, 36, 38, 44, or 46, the cDNA of ATCC 98881, or the cDNA of ATCC 98882.

Probes based on the sequence of a nucleic acid molecule of the invention can be used to detect transcripts or genomic sequences encoding the same protein molecule encoded by a selected nucleic acid molecule. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

A nucleic acid fragment encoding a "biologically active portion" of a polypeptide of the invention can be prepared by isolating a portion of any of SEQ ID NO: 3, 6, 26, 38, or 46, the nucleotide sequence of the cDNA of ATCC 98881, or the nucleotide sequence of the cDNA of ATCC 98882 which encodes a polypeptide having a biological activity, expressing the encoded portion of the polypeptide protein (e.g., by recombinant expression in vitro) and assessing the activity of the encoded portion of the polypeptide.

The invention further encompasses nucleic acid molecules that differ from the nucleotide sequence of SEQ ID NO:1, 3, 4, 6, 24, 26, 36, 38, 44, or 46, the cDNA of ATCC 98881, or the cDNA of ATCC 98882 due to degeneracy of the genetic code and thus encode the same protein as that encoded by the nucleotide sequence of SEQ ID NO:1, 3, 4, 6,24, 26, 36, 3 8, 44, or 46, the cDNA of ATCC 9888 1, or the cDNA of ATCC 98882.

In addition to the nucleotide sequences shown in SEQ ID NO:3 and 6 and present in the cDNA of ATCC 98881 and the cDNA of ATCC 98882, it will be appreciated by those skilled in the art that DNA sequence polymorphisms that lead to changes in the amino acid sequence may exist within a population (e.g., the human population). Such genetic polymorphisms may exist among individuals within a population due to natural allelic variation. An allele is one of a group of genes which occur alternatively at a given genetic locus. As used herein, the phrase "allelic variant" refers to a nucleotide sequence which occurs at a given locus or to a polypeptide encoded by the nucleotide sequence. As used herein, the terms "gene" and "recombinant gene" refer to nucleic acid molecules comprising an open reading frame encoding a polypeptide of the invention. Such natural allelic variations can typically result in 1–5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins of the invention from other species (homologues), which have a nucleotide sequence which differs from that of the protein described herein are intended to be within the scope of the invention. Nucleic acid molecules corresponding to natural allelic variants and homologues of a cDNA of the invention can be isolated based on their identity to the nucleic acid molecule disclosed herein using a cDNA, or a portion thereof, as a hybridization probe according to standard hybridization techniques under stringent hybridization conditions. For example, a cDNA encoding a soluble form of a membrane-bound protein of the invention isolated based on its hybridization to a nucleic acid molecule encoding all or part of the membrane-bound form. Likewise, a cDNA encoding a membrane-bound form can be isolated based on its hybridization to a nucleic acid molecule encoding all or part of the soluble form.

Accordingly, in another embodiment, an isolated nucleic acid molecule of the invention is at least 300 (325, 350, 375, 400, 425, 450, 500, 550, 600, 650, 700, 800, 900, 1000, or 1290) nucleotides in length and hybridizes under stringent conditions to the nucleic acid molecule comprising the nucleotide sequence, preferably the coding sequence, of SEQ ID NO:1, 3, 4, 6, 24, 26, 36, 38, 44, or 46, the cDNA of ATCC 98881, the cDNA of ATCC 98882, or a complement thereof.

As used herein, the term "hybridizes under stringent conditions" is intended to describe conditions for hybridization and washing under which nucleotide sequences at least 60% (65%, 70%, preferably 75%) identical to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50–65° C. Preferably, an isolated nucleic acid molecule of the invention that hybridizes under stringent conditions to the sequence of SEQ ID NO:1, 3, 4, 6, 24, 26, 36, 38, 44, or 46, the cDNA of ATCC 98881, or the cDNA of ATCC 98882, or the complement thereof, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of a nucleic acid molecule of the invention sequence that may exist in the population, the skilled artisan will further appreciate that changes can be introduced by mutation thereby leading to changes in the amino acid sequence of the encoded protein, without altering the biological activity of the protein. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologues of various species may be non-essential for activity and thus would be likely targets for alteration. Alternatively, amino acid residues that are conserved among the homologues of various species (e.g., murine and human) may be essential for activity and thus would not be likely targets for alteration.

Accordingly, another aspect of the invention pertains to nucleic acid molecules encoding a polypeptide of the invention that contain changes in amino acid residues that are not essential for activity. Such polypeptides differ in amino acid sequence from SEQ ID NO:2, 5, 8, and 13 yet retain biological activity. In one embodiment, the isolated nucleic acid molecule includes a nucleotide sequence encoding a protein that includes an amino acid sequence that is at least about 45% identical, 65%, 75%, 85%, 95%, or 98% identical to the amino acid sequence of any of SEQ ID NO:2, 5, 8, 13, 25, 28, 37, 40, 45, or 48.

An isolated nucleic acid molecule encoding a variant protein can be created by introducing one or more nucleotide substitutions, additions or deletions into the nucleotide sequence of SEQ ID NO:1, 3, 4, 6, 24, 26, 36, 38, 44, or 46, the cDNA of ATCC 98881, or the cDNA of ATCC 98882 such that one or more amino acid substitutions, additions or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, nethionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In a preferred embodiment, a mutant polypeptide that is a variant of a polypeptide of the invention can be assayed for: (1) the ability to form protein:protein interactions with proteins in a signaling pathway of the polypeptide of the invention; (2) the ability to bind a ligand of the polypeptide of the invention; or (3) the ability to bind to an intracellular target protein of the polypeptide of the invention. In yet another preferred embodiment, the mutant polypeptide can be assayed for the ability to modulate cellular proliferation or cellular differentiation.

The present invention encompasses antisense nucleic acid molecules, i.e., molecules which are complementary to a sense nucleic acid encoding a polypeptide of the invention, e.g., complementary to the coding strand of a double-stranded cDNA molecule or complementary to mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a noncoding region of the coding strand of a nucleotide sequence encoding a polypeptide of the invention. The noncoding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, bela-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a selected polypeptide of the invention to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pot II or pot III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave mRNA transcripts to thereby inhibit translation of the protein encoded by the mRNA. A ribozyme having specificity for a nucleic acid molecule encoding a polypeptide of the invention can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of the invention can be used to select a catalytic RNA having a specific ribonuclease activity from a pool of RNA molecules. See, e.g., Bartel and Szostak (1993) *Science* 261: 1411–1418.

The invention also encompasses nucleic acid molecules which form triple helical structures. For example, expression of a polypeptide of the invention can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569–84; Helene (1992) *Ann. N. Y Acad. Sci.* 660:27–36; and Maher (1992) *Bioassays* 14(12):807–15.

In preferred embodiments, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4(1): 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93: 14670–675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup (1996), supra; Perry-O'Keefe et al. (1996) *Proc. Natl. Acad. Sci. USA* 93: 14670–675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996), supra). The synthesis of PNA-DNA chimeras can be performed as described in Hyrup (1996), supra, and Finn et al. (1996) *Nucleic Acids Res.* 24(17):3357–63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al. (1989) *Nucleic Acids Res.* 17:5973–88). PNA monomers are then coupled in a stepwise manner to produce a chimeric molecule with a 5' PNA segment and a 3' DNA segment (Finn et al. (1996) *Nucleic Acids Res.* 24(17):3357–63). Alternatively, chimeric molecules can be synthesized with a 5' DNA segment and a 3' PNA segment (Peterser et al. (1975) *Bioorganic Med. Chem. Lett.* 5:1119–11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al. (1988) *Bio/Techniques* 6:958–976) or intercalating agents (see, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

II. Isolated Proteins and Antibodies

One aspect of the invention pertains to isolated proteins and polypeptides of the invention, and biologically active portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques. In another embodiment, polypeptides of the invention are produced by recombinant DNA techniques. Alternative to recombinant expression, a polypeptide of the invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a polypeptide of the invention include polypeptides comprising amino acid sequences sufficiently identical to or derived from the amino acid sequence of the protein (e.g., the amino acid sequence of SEQ ID NO:2, 5, 8, 13, 25, 28, 37, 40, 45, or 48), which include fewer amino acids than the full length protein, and exhibit at least one activity of the corresponding full-length protein. Typically, biologically active portions comprise a domain or motif with at least one activity of the corresponding protein. A biologically active portion of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the invention.

Preferred polypeptides have the amino acid sequence of SEQ ID NO:2, 5, 7–11, 12–16, 25, 28–35, 37, 40–43, 45, and 48–50. Other useful proteins are substantially identical (e.g., at least about 45%, preferably 55%, 65%, 75%, 85%, 95%, or 99%) to SEQ ID NO:2, 5, 7–11, 12–25, 28–35, 37, 40–43, 45, and 48–50 and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). Preferably, the two sequences are the same length.

The determination of percent homology between two sequences can be accomplished using a mathematical algorithm. A preferred, non-limiting example of a mathematical algorithm utilized for the comparison of two sequences is the algorithm of Karlin and Altschul (1990) *Proc. Natl.*

*Acad. Sci. USA* 87:2264–2268, modified as in Karlin and Altschul (1993) *Proc. Natl. Acad. Sci. USA* 90:5873–5877. Such an algorithm is incorporated into the NBLAST and XBLAST programs of Altschul, et al. (1990) *J. Mol. Biol.* 215:403–410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al. (1997) *Nucleic Acids Res.* 25:3389–3402. Alternatively, PSI-Blast can be used to perform an iterated search which detects distant relationships between molecules. Id. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *CABIOS* 4:11–17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, only exact matches are counted.

The invention also provides chimeric or fusion proteins. As used herein, a "chimeric protein" or "fusion protein" comprises all or part (preferably biologically active) of a polypeptide of the invention operably linked to a heterologous polypeptide (i.e., a polypeptide other than the same polypeptide of the invention). Within the fusion protein, the term "operably linked" is intended to indicate that the polypeptide of the invention and the heterologous polypeptide are fused in-frame to each other. The heterologous polypeptide can be fused to the N-terminus or C-terminus of the polypeptide of the invention.

One useful fusion protein is a GST fusion protein in which the polypeptide of the invention is fused to the C-terminus of GST sequences. Such fusion proteins can facilitate the purification of a recombinant polypeptide of the invention.

In another embodiment, the fusion protein contains a heterologous signal sequence at its N-terminus. For example, the native signal sequence of a polypeptide of the invention can be removed and replaced with a signal sequence from another protein. For example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

In yet another embodiment, the fusion protein is an immunoglobulin fusion protein in which all or part of a polypeptide of the invention is fused to sequences derived from a member of the immunoglobulin protein family. The immunoglobulin fusion proteins of the invention can be incorporated into pharmaceutical compositions and administered to a subject to inhibit an interaction between a ligand (soluble or membrane-bound) and a protein on the surface of a cell (receptor), to thereby suppress signal transduction in vivo. The immunoglobulin fusion protein can be used to affect the bioavailability of a cognate ligand of a polypeptide of the invention. Inhibition of ligand/receptor interaction may be useful therapeutically, both for treating proliferative and differentiative disorders and for modulating (e.g. promoting or inhibiting) cell survival. Moreover, the immunoglobulin fusion proteins of the invention can be used as immunogens to produce antibodies directed against a polypeptide of the invention in a subject, to purify ligands and in screening assays to identify molecules which inhibit the interaction of receptors with ligands.

Chimeric and fusion protein of the invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the invention can be cloned into such an expression vector such that the fusion moiety is linked in-frame to the polypeptide of the invention.

A signal sequence of a polypeptide of the invention (SEQ ID NO:7, 12, 27, 39, or 47) can be used to facilitate secretion and isolation of a secreted protein or other protein of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to the signal sequence itself and to the polypeptide in the absence of the signal sequence (i.e., the cleavage products). In one embodiment, a nucleic acid sequence encoding a signal sequence of the invention can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

In another embodiment, the signal sequences of the present invention can be used to identify regulatory sequences, e.g., promoters, enhancers, repressors. Since signal sequences are the most amino-terminal sequences of a peptide, it is expected that the nucleic acids which flank the signal sequence on its amino-terminal side will be regulatory sequences which affect transcription. Thus, a nucleotide sequence which encodes all or a portion of a signal sequence can be used as a probe to identify and isolate signal sequences and their flanking regions, and these flanking regions can be studied to identify regulatory elements therein.

The present invention also pertains to variants of the polypeptides of the invention. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the invention from a degenerate oligonucleotide sequence. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198: 1056; Ike et al. (1983) *Nucleic Acid Res.* 11:477).

In addition, libraries of fragments of the coding sequence of a polypeptide of the invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected.

Recursive ensemble mutagenesis (REM), a technique which enhances the frequency of functional mutants in the libraries, can be used in combination with the screening assays to identify variants of a protein of the invention (Arkin and Yourvan (1992) *Proc. Natl. Acad. Sci. USA* 89:7811–7815; Delgrave et al. (1993) *Protein Engineering* 6(3):327–331).

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:8, 13, 28, 40, or 48 and encompasses an epitope of the protein such that an antibody raised against the peptide forms a specific immune complex with the protein.

Preferred epitopes encompassed by the antigenic peptide are regions that are located on the surface of the protein, e.g., hydrophilic regions. FIGS. 2 and 4 are hydrophobicity plots of the proteins of the invention. These plots or similar analyses can be used to identify hydrophilic regions.

An immunogen typically is used to prepare antibodies by immunizing a suitable subject, (e.g., rabbit, goat, mouse or other mammal). An appropriate immunogenic preparation can contain, for example, recombinantly expressed chemically synthesized polypeptide. The preparation can further include an adjuvant, such as Freund's complete or incomplete adjuvant, or similar immunostimulatory agent.

Accordingly, another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope.

Polyclonal antibodies can be prepared as described above by immunizing a suitable subject with a polypeptide of the invention as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B cell hybridoma technique (Kozbor et al. (1983) *Immunol. Today*

4:72), the EBV-hybridoma technique (Cole et al. (1985), *Monoclonal Antibodies and Cancer Therapy*, Alan R. Liss, Inc., pp. 77–96) or trioma techniques. The technology for producing hybridomas is well known (see generally *Current Protocols in Immunology* (1994) Coligan et al. (eds.) John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Alternative to preparing monoclonal antibody-secreting hybridomas, a monoclonal antibody directed against a polypeptide of the invention can be identified and isolated by screening a recombinant combinatorial immunoglobulin library (e.g., an antibody phage display library) with the polypeptide of interest. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al. (1993) *EMBO J.* 12:725–734.

Additionally, recombinant antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol.* 139:3521–3526; Sun et al. (1987) *Proc. Natl. Acad. Sci. USA* 84:214–218; Nishimura et al. (1987) *Canc. Res.* 47:999–1005; Wood et al. (1985) *Nature* 314:446–449; and Shaw et al. (1988) *J. Natl. Cancer Inst.* 80:1553–1559); Morrison (1985) *Science* 229:1202–1207; Oi et al. (1986) *Bio/Techniques* 4:214; U.S. Pat. No. 5,225,539; Jones et al. (1986) *Nature* 321:552–525; Verhoeyan et al. (1988) *Science* 239:1534; and Beidler et al. (1988) *J. Immunol.* 141:4053–4060.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, *Int. Rev. Immunol.* 13:65–93). For a detailed discussion of this technology for producing human antibodies and human monoclonal antibodies and protocols for producing such antibodies, see, e.g., U.S. Pat. Nos. 5,625,126; 5,633, 425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a murine antibody, is used to guide the selection of a completely human antibody recognizing the same epitope (Jespers et al. (1994) *Bio/Technology* 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

III. Recombinant Expression Vectors and Host Cells

Another aspect of the invention pertains to vectors, preferably expression vectors, containing a nucleic acid encoding a polypeptide of the invention (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of a polypeptide of the invention in prokaryotic or eukaryotic cells, e.g., bacterial cells such as *E. coli,* insect cells (using baculovirus expression vectors), yeast cells or mammalian cells. Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., (1988) *Gene* 69:301–315) and pET ld (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gnl1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the expression vector is a yeast expression vector. Examples of vectors for expression in yeast *S. cerivisae* include pYepSecl (Baldari et al. (1987) *EMBO J.* 6:229–234), pMFa (Kurjan and Herskowitz, (1982) *Cell* 30:933–943), pJRY88 (Schultz et al. (1987) *Gene* 54:113–123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al.

(1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example the murine hox promoters (Kessel and Gruss (1990) *Science* 249:374–379) and the Cc-fetoprotein promoter (Campes and Tilghman (1989) *Genes Dev.* 3:537–546).

The invention further provides a recombinant expression vector comprising a DNA molecule of the invention cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. 1(1) 1986).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., an insect cell, yeast, or a mammalian cell).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce a polypeptide of the invention. Accordingly, the invention further provides methods for producing a polypeptide of the invention using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

The host cells of the invention can also be used to produce nonhuman transgenic animals. For example, in one embodiment, a host cell of the invention is a fertilized oocyte or an embryonic stem cell into which a sequences encoding a polypeptide of the invention have been introduced. Such host cells can then be used to create non-human transgenic animals in which exogenous sequences encoding a polypeptide of the invention have been introduced into their genome or homologous recombinant animals in which endogenous encoding a polypeptide of the invention sequences have been altered. Such animals are useful for studying the function and/or activity of the polypeptide and for identifying and/or evaluating modulators of polypeptide activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, an "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

A transgenic animal of the invention can be created by introducing nucleic acid encoding a polypeptide of the invention (or a homologue thereof) into the male pronuclei of a fertilized oocyte, e.g., by microinjection, retroviral infection, and allowing the oocyte to develop in a pseudopregnant female foster animal. Intronic sequences and polyadenylation signals can also be included in the transgene to increase the efficiency of expression of the transgene. A tissue-specific regulatory sequence(s) can be operably linked to the transgene to direct expression of the polypeptide of the invention to particular cells. Methods for generating transgenic animals via embryo manipulation and microinjection, particularly animals such as mice, have become conventional in the art and are described, for example, in U.S. Pat. Nos. 4,736,866 and 4,870,009, 4,873, 191 and in Hogan, *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of mRNA encoding the transgene in tissues or cells of the animals. A transgenic founder animal can then be used to breed additional animals carrying the transgene. Moreover, transgenic animals carrying the transgene can further be bred to other transgenic animals carrying other transgenes.

To create an homologous recombinant animal, a vector is prepared which contains at least a portion of a gene encoding a polypeptide of the invention into which a deletion, addition or substitution has been introduced to thereby alter, e.g., functionally disrupt, the gene. In a preferred embodiment, the vector is designed such that, upon homologous recombination, the endogenous gene is functionally disrupted (i.e., no longer encodes a functional protein; also referred to as a "knock out" vector). Alternatively, the vector can be designed such that, upon homologous recombination, the endogenous gene is mutated or otherwise altered but still encodes functional protein (e.g., the upstream regulatory region can be altered to thereby alter the expression of the endogenous protein). In the homologous recombination vector, the altered portion of the gene is flanked at its 5' and 3' ends by additional nucleic acid of the gene to allow for homologous recombination to occur between the exogenous gene carried by the vector and an endogenous gene in an embryonic stem cell. The additional flanking nucleic acid sequences are of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation) and cells in which the introduced gene has homologously recombined with the endogenous gene are selected (see, e.g., Li et al. (1992) *Cell* 69:915). The selected cells are then injected into a blastocyst of an animal (e.g., a mouse) to form aggregation chimeras (see, e.g., Bradley in *Teratocarcinomas and Embryonic Stem Cells: A Practical Approach,* Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication NOS. WO 90/11354, WO 91/01140, WO 92/0968, and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813 and PCT Publication NOS. WO 97/07668 and WO 97/07669.

IV. Pharmaceutical Compositions

The nucleic acid molecules, polypeptides, and antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The nucleic acid molecules of the invention can be inserted into vectors and used as gene therapy vectors. Gene therapy vectors can be delivered to a subject by, for example, intravenous injection, local administration (U.S. Pat. No. 5,328,470) or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) detection assays (e.g., chromosomal mapping, tissue typing, forensic biology); c) predictive medicine (e.g., diagnostic assays, prognostic assays, monitoring clinical trials, and pharmacogenomics); and d) methods of treatment (e.g., therapeutic and prophylactic). For example, polypeptides of the invention can to used to (i) modulate cellular proliferation; (ii) modulate cellular differentiation; and (iii) modulate cell survival. The isolated nucleic acid molecules of the invention can be used to express proteins (e.g., via a recombinant expression vector in a host cell in gene therapy applications), to detect mRNA (e.g., in a biological sample) or a genetic lesion, and to modulate activity of a polypeptide of the invention.

As used herein, the term "modulate" refers to the ability of a molecule, protein, protein homologue, or antibody of the invention to affect, exert an influence on, change in character, or keep in proper measure or proportion, any method, process, assay, gene, protein, or molecule it encounters or comes into contact (directly or indirectly) with. Examples of modulating activities include stimulation (e.g., increase) or inhibition (e.g., decrease), e.g., of cellular proliferation; exercising an agonistic or antagonistic effect, e.g., on a receptor's ability to bind its ligand; and upregulation or downregulation, e.g., of gene expression.

In addition, the polypeptides of the invention can be used to screen drugs or compounds which modulate activity or expression of a polypeptide of the invention as well as to treat disorders characterized by insufficient or excessive production of a protein of the invention or production of a form of a protein of the invention which has decreased or aberrant activity compared to the wild type protein. In addition, the antibodies of the invention can be used to detect and isolate a protein of the and modulate activity of a protein of the invention.

This invention further pertains to novel agents identified by the above-described screening assays and uses thereof for treatments as described herein.

A. Screening Assays

The invention provides a method (also referred to herein as a "screening assay") for identifying modulators, i.e., candidate or test compounds or agents (e.g., peptides, peptidomimetics, small molecules or other drugs) which bind to polypeptide of the invention or have a stimulatory or inhibitory effect on, for example, expression or activity of a polypeptide of the invention.

In one embodiment, the invention provides assays for screening candidate or test compounds which bind to or modulate the activity of the membrane-bound form of a polypeptide of the invention or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869) or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

In one embodiment, an assay is a cell-based assay in which a cell which expresses a membrane-bound form of a polypeptide of the invention, or a biologically active portion thereof, on the cell surface is contacted with a test compound and the ability of the test compound to bind to the polypeptide determined. The cell, for example, can be a yeast cell or a cell of mammalian origin. Determining the ability of the test compound to bind to the polypeptide can be accomplished, for example, by coupling the test compound with a radioisotope or enzymatic label such that binding of the test compound to the polypeptide or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses a membrane-bound form of a polypeptide of the invention, or a biologically active portion thereof, on the cell surface with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or a biologically active portion thereof as compared to the known compound.

In another embodiment, an assay is a cell-based assay comprising contacting a cell expressing a membrane-bound form of a polypeptide of the invention, or a biologically active portion thereof, on the cell surface with a test compound and determining the ability of the test compound to modulate (e.g., stimulate or inhibit) the activity of the polypeptide or biologically active portion thereof. Determining the ability of the test compound to modulate the activity of the polypeptide or a biologically active portion thereof can be accomplished, for example, by determining the ability of the polypeptide protein to bind to or interact with a target molecule.

Determining the ability of a polypeptide of the invention to bind to or interact with a target molecule can be accomplished by one of the methods described above for determining direct binding. As used herein, a "target molecule" is a molecule with which a selected polypeptide (e.g., a polypeptide of the invention binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. A target molecule can be a polypeptide of the invention or some other polypeptide or protein. For example, a target molecule can be a component of a signal transduction pathway which facilitates transduction of an extracellular signal (e.g., a signal generated by binding of a compound to a polypeptide of the invention) through the cell membrane and into the cell or a second intercellular protein which has catalytic activity or a protein which facilitates the association of downstream signaling molecules with a polypeptide of the invention. Determining the ability of a polypeptide of the invention to bind to or interact with a target molecule can be accomplished by determining the activity of the target molecule.

For example, the activity of the target molecule can be determined by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, e.g. luciferase), or detecting a cellular response, for example, cellular differentiation, or cell proliferation.

In yet another embodiment, an assay of the present invention is a cell-free assay comprising contacting a polypeptide of the invention or biologically active portion thereof with a test compound and determining the ability of the test compound to bind to the polypeptide or biologically active portion thereof. Binding of the test compound to the polypeptide can be determined either directly or indirectly as described above. In a preferred embodiment, the assay includes contacting the polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the test compound to preferentially bind to the polypeptide or biologically active portion thereof as compared to the known compound.

In another embodiment, an assay is a cell-free assay comprising contacting a polypeptide of the invention or biologically active portion thereof with a test compound and determining the ability of the test compound to modulate (e.g., stimulate or inhibit) the activity of the polypeptide or biologically active portion thereof. Determining the ability of the test compound to modulate the activity of the polypeptide can be accomplished, for example, by determining the ability of the polypeptide to bind to a target molecule by one of the methods described above for determining direct binding. In an alternative embodiment, determining the ability of the test compound to modulate the activity of the polypeptide can be accomplished by determining the ability of the polypeptide of the invention to further modulate the target molecule. For example, the catalytic/enzymatic activity of the target molecule on an appropriate substrate can be determined as previously described.

In yet another embodiment, the cell-free assay comprises contacting a polypeptide of the invention or biologically active portion thereof with a known compound which binds the polypeptide to form an assay mixture, contacting the assay mixture with a test compound, and determining the ability of the test compound to interact with the polypeptide, wherein determining the ability of the test compound to interact with the polypeptide comprises determining the ability of the polypeptide to preferentially bind to or modulate the activity of a target molecule.

The cell-free assays of the present invention are amenable to use of both a soluble form or the membrane-bound form of a polypeptide of the invention. In the case of cell-free assays comprising the membrane-bound form of the polypeptide, it may be desirable to utilize a solubilizing agent such that the membrane-bound form of the polypeptide is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton X-100, Triton X-114, Thesit, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either the polypeptide of the invention or its target molecule to facilitate separation of complexed from uncomplexed forms of one or both of the proteins, as well as to accommodate automation of the assay. Binding of a test compound to the polypeptide, or interaction of the polypeptide with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase fusion proteins or glutathione-S-transferase fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or A polypeptide of the invention, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of binding or activity of the polypeptide of the invention can be determined using standard techniques.

Other techniques for immobilizing proteins on matrices can also be used in the screening assays of the invention. For example, either the polypeptide of the invention or its target molecule can be immobilized utilizing conjugation of biotin and streptavidin. Biotinylated polypeptide of the invention or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the polypeptide of the invention or target molecules but which do not interfere with binding of the polypeptide of the invention to its target molecule can be derivatized to the wells of the plate, and unbound target or polypeptidede of the invention trapped in the wells by antibody conjugation. Methods for detecting such complexes, in addition to those described above for the GST-immobilized complexes, include immunodetection of complexes using antibodies reactive with the polypeptide of the invention or target molecule, as well as enzyme-linked assays which rely on detecting an enzymatic activity associated with the polypeptide of the invention or target molecule.

In another embodiment, modulators of expression of a polypeptide of the invention are identified in a method in which a cell is contacted with a candidate compound and the expression of the selected mRNA or protein (i.e., the mRNA or protein corresponding to a polypeptide or nucleic acid of the invention) in the cell is determined. The level of expression of the selected mRNA or protein in the presence of the candidate compound is compared to the level of expression of the selected mRNA or protein in the absence of the candidate compound. The candidate compound can then be identified as a modulator of expression of the polypeptide of the invention based on this comparison. For example, when expression of the selected mRNA or protein is greater (statistically significantly greater) in the presence of the candidate compound than in its absence, the candidate compound is identified as a stimulator of the selected mRNA or protein expression. Alternatively, when expression of the selected mRNA or protein is less (statistically significantly less) in the presence of the candidate compound than in its absence, the candidate compound is identified as an inhibitor of the selected mRNA or protein expression. The level of the selected mRNA or protein expression in the cells can be determined by methods described herein.

In yet another aspect of the invention, a polypeptide of the inventions can be used as "bait proteins" in a two-hybrid assay or three hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Bio/Techniques* 14:920–924; Iwabuchi et al. (1993) *Oncogene* 8:1693–1696; and PCT Publication No. WO 94/10300), to identify other proteins, which bind to or interact with the polypeptide of the invention and modulate activity of the polypeptide of the invention. Such binding proteins are also likely to be involved in the propagation of signals by the polypeptide of the inventions as, for example, upstream or downstream elements of a signaling pathway involving the polypeptide of the invention.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. Accordingly, nucleic acid molecules described herein or fragments thereof, can be used to map the location of the corresponding genes on a chromosome. The mapping of the sequences to chromosomes is an important first step in correlating these sequences with genes associated with disease.

Briefly, genes can be mapped to chromosomes by preparing PCR primers (preferably 15–25 bp in length) from the sequence of a gene of the invention. Computer analysis of the sequence of a gene of the invention can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the gene sequences will yield an amplified fragment. For a review of this technique, see D'Eustachio et al. ((1983) *Science* 220:919–924).

PCR mapping of somatic cell hybrids is a rapid procedure for assigning a particular sequence to a particular chromosome. Three or more sequences can be assigned per day using a single thermal cycler. Using the nucleic acid sequences of the invention to design oligonucleotide primers, sublocalization can be achieved with panels of fragments from specific chromosomes. Other mapping strategies which can similarly be used to map a gene to its chromosome include in situ hybridization (described in Fan et al. (1990) *Proc. Natl. Acad. Sci. USA* 87:6223–27), pre-screening with labeled flow-sorted chromosomes (CITE), and pre-selection by hybridization to chromosome specific cDNA libraries (CITE). Fluorescence in situ hybridization (FISH) of a DNA sequence to a metaphase chromosomal spread can further be used to provide a precise chromosomal location in one step. For a review of this technique, see Verma et al., (Human Chromosomes: A Manual of Basic Techniques (Pergamon Press, New York, 1988)).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) *Nature* 325:783–787.

Moreover, differences in the DNA sequences between individuals affected and unaffected with a disease associated with a gene of the invention can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The nucleic acid sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the nucleic acid sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The nucleic acid sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can comfortably provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from the nucleic acid sequences described herein is used to generate a unique identification database for an individual, those same reagents can later be used to identify tissue from that individual. Using the unique identification database, positive identification of the individual, living or dead, can be made from extremely small tissue samples.

3. Use of Partial Gene Sequences in Forensic Bioloby

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions are particularly appropriate for this use as greater numbers of polymorphisms occur in the noncoding regions, making it easier to differentiate individuals using this technique. Examples of polynucleotide reagents include the nucleic acid sequences of the invention or portions thereof, e.g., fragments derived from noncoding regions having a length of at least 20 or 30 bases.

The nucleic acid sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such probes can be used to identify tissue by species and/or by organ type.

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. Accordingly, one aspect of the present invention relates to diagnostic assays for determining expression of a polypeptide or nucleic acid of the invention and/or activity of a polypeptide of the invention, in the context of a biological sample (e.g., blood, serum, cells, tissue) to thereby determine whether an individual is afflicted with a disease or disorder, or is at risk of developing a disorder, associated with aberrant expression or activity of a polypeptide of the invention. The invention also provides for prognostic (or predictive) assays for determining whether an individual is at risk of developing a disorder associated with aberrant expression or activity of a polypeptide of the invention For example, mutations in a gene of the invention can be assayed in a biological sample. Such assays can be used for prognostic or predictive purpose to thereby prophylactically treat an individual prior to the onset of a disorder characterized by or associated with aberrant expression or activity of a polypeptide of the invention.

Another aspect of the invention provides methods for expression of a nucleic acid or polypeptide of the invention or activity of a polypeptide of the invention in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Yet another aspect of the invention pertains to monitoring the influence of agents (e.g., drugs or other compounds) on the expression or activity of a polypeptide of the invention in clinical trials.

These and other agents are described in further detail in the following sections:

1. Diagnostic Assays

An exemplary method for detecting the presence or absence of a polypeptide or nucleic acid of the invention in a biological sample involves obtaining a biological sample from a test subject and contacting the biological sample with a compound or an agent capable of detecting a polypeptide or nucleic acid (e.g., mRNA, genomic DNA) of the invention such that the presence of a polypeptide or nucleic acid of the invention is detected in the biological sample. A preferred agent for detecting mRNA or genomic DNA encoding a polypeptide of the invention is a labeled nucleic acid probe capable of hybridizing to mRNA or genomic DNA encoding a polypeptide of the invention. The nucleic acid probe can be, for example, a full-length cDNA, such as the nucleic acid of SEQ ID NO:1 or 4, or a portion thereof, such as an oligonucleotide of at least 15, 30, 50, 100, 250 or 500 nucleotides in length and sufficient to specifically hybridize under stringent conditions to a mRNA or genomic DNA encoding a polypeptide of the invention. Other suitable probes for use in the diagnostic assays of the invention are described herein.

A preferred agent for detecting A polypeptide of the invention is an antibody capable of binding to A polypeptide of the invention, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect mRNA, protein, or genomic DNA in a biological sample in vitro as well as in vivo. For example, in vitro techniques for detection of mRNA include Northern hybridizations and in situ hybridizations. In vitro techniques for detection of A polypeptide of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide of the invention include introducing into a subject a labeled antibody directed against the polypeptide. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting a polypeptide of the invention or mRNA or genomic DNA encoding a polypeptide of the invention, such that the presence of the polypeptide or mRNA or genomic DNA encoding the polypeptide is detected in the biological sample, and comparing the presence of the polypeptide or mRNA or genomic DNA encoding the polypeptide in the control sample with the presence of the polypeptide or mRNA or genomic DNA encoding the polypeptide in the test sample.

The invention also encompasses kits for detecting the presence of a polypeptide or nucleic acid of the invention in a biological sample (a test sample). Such kits can be used to determine if a subject is suffering from or is at increased risk of developing a disorder associated with aberrant expression of a polypeptide of the invention (e.g., an immunological disorder). For example, the kit can comprise a labeled compound or agent capable of detecting the polypeptide or mRNA encoding the polypeptide in a biological sample and means for determining the amount of the polypeptide or mRNA in the sample (e.g., an antibody which binds the polypeptide or an oligonucleotide probe which binds to DNA or mRNA encoding the polypeptide). Kits may also include instruction for observing that the tested subject is suffering from or is at risk of developing a disorder associated with aberrant expression of the polypeptide if the amount of the polypeptide or mRNA encoding the polypeptide is above or below a normal level.

For antibody-based kits, the kit may comprise, for example: (1) a first antibody (e.g., attached to a solid support) which binds to a polypeptide of the invention; and, optionally, (2) a second, different antibody which binds to either the polypeptide or the first antibody and is conjugated to a detectable agent.

For oligonucleotide-based kits, the kit may comprise, for example: (1) an oligonucleotide, e.g., a detectably labeled oligonucleotide, which hybridizes to a nucleic acid sequence encoding a polypeptide of the invention or (2) a pair of primers useful for amplifying a nucleic acid molecule encoding a polypeptide of the invention.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

2. Prognostic Assays

The methods described herein can furthermore be utilized as diagnostic or prognostic assays to identify subjects having or at risk of developing a disease or disorder associated with aberrant expression or activity of a polypeptide of the invention. For example, the assays described herein, such as the preceding diagnostic assays or the following assays, can be utilized to identify a subject having or at risk of developing a disorder associated with aberrant expression or activity of a polypeptide of the invention. Alternatively, the prognostic assays can be utilized to identify a subject having or at risk for developing such a disease or disorder. Thus, the present invention provides a method in which a test sample is obtained from a subject and a polypeptide or nucleic acid (e.g., mRNA, genomic DNA) of the invention is detected, wherein the presence of the polypeptide or nucleic acid is diagnostic for a subject having or at risk of developing a disease or disorder associated with aberrant expression or activity of the polypeptide. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant expression or activity of a polypeptide of the invention. For example, such methods can be used to determine whether a subject can be effectively treated with a specific agent or class of agents (e.g., agents of a type which decrease activity of the polypeptide). Thus, the present invention provides methods for determining whether a subject can be effectively treated with an agent for a disorder associated with aberrant expression or activity of a polypeptide of the invention in which a test sample is obtained and the polypeptide or nucleic acid encoding the polypeptide is detected (e.g., wherein the presence of the polypeptide or nucleic acid is diagnostic for a subject that can be administered the agent to treat a disorder associated with aberrant expression or activity of the polypeptide).

The methods of the invention can also be used to detect genetic lesions or mutations in a gene of the invention, thereby determining if a subject with the lesioned gene is at risk for a disorder characterized aberrant expression or activity of a polypeptide of the invention. In preferred embodiments, the methods include detecting, in a sample of cells from the subject, the presence or absence of a genetic lesion or mutation characterized by at least one of an alteration affecting the integrity of a gene encoding the polypeptide of the invention, or the mis-expression of the gene encoding the polypeptide of the invention. For example, such genetic lesions or mutations can be detected by ascertaining the existence of at least one of: 1) a deletion of one or more nucleotides from the gene; 2) an addition of one or more nucleotides to the gene; 3) a substitution of one or more nucleotides of the gene; 4) a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene. As described herein, there are a large number of assay techniques known in the art which can be used for detecting lesions in a gene.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in a gene (see, e.g., Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to the selected gene under conditions such that hybridization and amplification of the gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh, et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a selected gene from a sample cell can be identified by alterations in restriction enzyme cleavage patterns. For example, sample and ontrol DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). For example, genetic mutations can be identified in two-dimensional arrays containing light-generated DNA probes as described in Cronin et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the selected gene and detect mutations by comparing the sequence of the sample nucleic acids with the corresponding wild-type (control) sequence. Examples of sequencing reactions include those based on techniques developed by Maxim and Gilbert ((1977) *Proc. Natl. Acad. Sci. USA* 74:560) or Sanger ((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in a selected gene include methods in which protection from cleavage agents is used to detect mismatched bases in RNA/RNA or RNA/DNA heteroduplexes (Myers et al. (1985) *Science* 230:1242). In general, the technique of "mismatch cleavage" entails providing heteroduplexes formed by hybridizing (labeled) RNA or DNA containing the wild-type sequence with potentially mutant RNA or DNA obtained from a tissue sample. The double-stranded duplexes are treated with an agent which cleaves single-stranded regions of the duplex such as which will exist due to basepair mismatches between the control and sample strands. RNA/DNA duplexes can be treated with RNase to digest mismatched regions, and DNA/DNA hybrids can be treated with S 1 nuclease to digest mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton et al. (1988) *Proc. Natl. Acad. Sci. USA* 85:4397; Saleeba et al. (1992) *Methods Enzymol.* 217:286–295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a selected sequence, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify utations in genes. For example, single strand conformation polymorphism (SSCP) may be used o detect differences in electrophoretic mobility between mutant and wild type nucleic acids Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). Single-stranded DNA fragments of sample and control nucleic acids will be denatured and allowed to renature. The secondary structure of single-stranded nucleic acids varies according to sequence, and the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a 'GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a gene encoding a polypeptide of the invention.

Furthermore, any cell type or tissue, preferably peripheral blood leukocytes, in which the polypeptide of the invention is expressed may be utilized in the prognostic assays described herein.

3. Pharmacogenomics

Agents, or modulators which have a stimulatory or inhibitory effect on activity or expression of a polypeptide of the invention as identified by a screening assay described herein can be administered to individuals to treat (prophylactically or therapeutically) disorders associated with aberrant activity of the polypeptide. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of a polypeptide of the invention, expression of a nucleic acid of the invention, or mutation content of a gene of the invention in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug.

These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of a polypeptide of the invention, expression of a nucleic acid encoding the polypeptide, or mutation content of a gene encoding the polypeptide in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a modulator of activity or expression of the polypeptide, such as a modulator identified by one of the exemplary screening assays described herein.

4. Monitoring of Effects During Clinical Trials

Monitoring the influence of agents (e.g., drugs, compounds) on the expression or activity of a polypeptide of the invention (e.g., the ability to modulate aberrant cell proliferation and/or differentiation) can be applied not only in basic drug screening, but also in clinical trials. For example, the effectiveness of an agent, as determined by a screening assay as described herein, to increase gene expression, protein levels or protein activity, can be monitored in clinical trials of subjects exhibiting decreased gene expression, protein levels, or protein activity. Alternatively, the effectiveness of an agent, as determined by a screening assay, to decrease gene expression, protein levels or protein activity, can be monitored in clinical trials of subjects exhibiting increased gene expression, protein levels, or protein activity. In such clinical trials, expression or activity of a polypeptide of the invention and preferably, that of other polypeptide that have been implicated in for example, a cellular proliferation disorder, can be used as a marker of the immune responsiveness of a particular cell.

For example, and not by way of limitation, genes, including those of the invention, that are modulated in cells by treatment with an agent (e.g., compound, drug or small molecule) which modulates activity or expression of a polypeptide of the invention (e.g., as identified in a screening assay described herein) can be identified. Thus, to study the effect of agents on cellular proliferation disorders, for example, in a clinical trial, cells can be isolated and RNA prepared and analyzed for the levels of expression of a gene of the invention and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of a gene of the invention or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the agent; (ii) detecting the level of the polypeptide or nucleic acid of the invention in the preadministration sample; (iii) obtaining one or more post-administration samples from the subject; (iv) detecting the level the of the polypeptide or nucleic acid of the invention in the post-administration samples; (v) comparing the level of the polypeptide or nucleic acid of the invention in the pre-administration sample with the level of the polypeptide or nucleic acid of the invention in the post-administration sample or samples; and (vi) altering the administration of the agent to the subject accordingly. For example, increased administration of the agent may be desirable to increase the expression or activity of the polypeptide to higher levels than detected, i.e., to increase the effectiveness of the agent. Alternatively, decreased administration of the agent may be desirable to decrease expression or activity of the polypeptide to lower levels than detected, i.e., to decrease the effectiveness of the agent.

C. Methods of Treatment

The present invention provides for both prophylactic and therapeutic methods of treating a subject at risk of (or susceptible to) a disorder or having a disorder associated with aberrant expression or activity of a polypeptide of the invention.

1. Prophylactic Methods

In one aspect, the invention provides a method for preventing in a subject, a disease or condition associated with an aberrant expression or activity of a polypeptide of the invention, by administering to the subject an agent which modulates expression or at least one activity of the polypeptide. Subjects at risk for a disease which is caused or contributed to by aberrant expression or activity of a polypeptide of the invention can be identified by, for example, any or a combination of diagnostic or prognostic assays as described herein. Administration of a prophylactic agent can occur prior to the manifestation of symptoms characteristic of the aberrancy, such that a disease or disorder is prevented or, alternatively, delayed in its progression. Depending on the type of aberrancy, for example, an agonist or antagonist agent can be used for treating the subject. The appropriate agent can be determined based on screening assays described herein.

2. Therapeutic Methods

Another aspect of the invention pertains to methods of modulating expression or activity of a polypeptide of the invention for therapeutic purposes. The modulatory method of the invention involves contacting a cell with an agent that modulates one or more of the activities of the polypeptide. An agent that modulates activity can be an agent as described herein, such as a nucleic acid or a protein, a naturally-occurring cognate ligand of the polypeptide, a peptide, a peptidomimetic, or other small molecule. In one embodiment, the agent stimulates one or more of the biological activities of the polypeptide. Examples of such stimulatory agents include the active polypeptide of the invention and a nucleic acid molecule encoding the polypeptide of the invention that has been introduced into the cell. In another embodiment, the agent inhibits one or more of the biological activities of the polypeptide of the invention. Examples of such inhibitory agents include antisense nucleic acid molecules and antibodies. These modulatory methods can be performed in vitro (e.g., by culturing the cell with the agent) or, alternatively, in vivo (e.g, by administering the agent to a subject). As such, the present invention provides methods of treating an individual afflicted with a disease or disorder characterized by aberrant expression or activity a polypeptide of the invention. In one embodiment, the method involves administering an agent (e.g., an agent identified by a screening assay described herein), or combination of agents that modulates (e.g., upregulates or downregulates) expression or activity. In another embodiment, the method involves administering a polypeptide of the invention or a nucleic acid molecule of the invention as therapy to compensate for reduced or aberrant expression or activity of the polypeptide.

Stimulation of activity is desirable in situations in which activity or expression is abnormally low downregulated and/or in which increased activity is likely to have a beneficial effect. Conversely, inhibition of activity is desirable in situations in which activity or expression is abnormally high or upregulated and/or in which decreased activity is likely to have a beneficial effect.

This invention is further illustrated by the following examples which should not be construed as limiting. The contents of all references, patents and published patent applications cited throughout this application are hereby incorporated by reference.

EXAMPLES

Example 1

Isolation and Characterization of TANGO 195 cDNAs

PBMCs were isolated by ficol gradient from approx. 100 ml of peripheral blood from 24 healthy donors. Total lymphocytes were cultured at $1\times10^7$ cells/ml in RPMI 10% FCS. Equal numbers of starting cells were harvested at 4, 8 and 24 hours and RNA was purified using standard techniques.

Mixed lymphocyte reaction cDNA library was prepared as follows: 50 ml of peripheral blood was collected from 22 volunteer donors into heparinized tubes and mononuclear cells were isolated using Histopaque 1077 (Sigma) according to manufacturer's instructions. Cells were pooled and CD19+ B cells were removed by positive selection using MACS beads and VS+ separation column (Miltenyi Biotec, Germany) according to manufacturer's instructions. CD19– cells were resuspended at $10\times10^6$ cells per ml in RPMI 10% FBS supplemented with antibiotics and L-glutamine. Cells were incubated at 37° C. in a humidified incubator and harvested at 4, 14 and 24 hours.

Total RNA was isolated using guanidinium isothiocyanate/beta-mercaptoethanol lysis and cesium chloride gradient centrifugation. After DNase treatment, the poly A+ fraction of total RNA was further purified using Oligotex beads (Qiagen, Inc.). 4.4 micrograms of poly A+ RNA were used to synthesize a cDNA library using the Superscript cDNA Synthesis kit (Gibco BRL, Inc.; Gaithersburg, Md.). Complementary DNA was directionally cloned into the expression plasmid pMET7 using the SalI and NotI sites in the polylinker to construct a plasmid library. Transformants were randomly picked and grown up for single pass sequencing.

The mixed lymphocyte reaction library was studied by high throughput single pass sequencing and computer analysis. The cDNA clone encoding TANGO 195 was identified from the above-described cDNA library using the following method. First, each sequence was checked to determine if it was a bacterial, ribosomal, or mitochondrial contaminant. Such sequences were excluded from the subsequent analysis. Second, sequence artifacts, such as vector and repetitive elements, were masked and/or removed from each sequence. Third, the remaining sequences were searched against a copy of the GenBank nucleotide database using the BLASTN™ program (BLASTN 1.3MP: Altschul et al., *J. Mol. Bio.* 215:403, 1990). Fourth, the sequences were analyzed against a non-redundant protein database with the BLASTX™ program, which translates a nucleic acid sequence in all six frames and compares it against available protein databases (BLASTX 1.3MP:Altschul et al., suprac). This protein database is a combination of the Swiss-Prot, PIR, and NCBI GenPept protein databases.

T195 was originally identified by BLAST analysis as a homolog of SLAM and a full length clone was identified (T195 full length). The mouse ortholog was identified as a full length clone in a lung library from a mouse asthma model 3 hours after antigen challenge.

Example 2

Distribution of TANGO 195 mRNA In Human Tissues Northern Blot Analysis

A human poly $A^+$ Immune blot (Clonetech Palo Alto Calif.) was probed using a $^{32}P$ labeled probe corresponding to amino acids 1–233 of full length human T195 as per the manufacturer's instructions. RNA was prepared from all cell types using an RNeasy mini kit (Qiagen) and expression was analyzed by standard Northern analysis using approximately 10 ug total RNA.

Human PBMCs were isolated from normal healthy donors by ficol gradient centrifugation. Total PBMCs were stimulated for 4 hours in RPMI 10% FCS supplemented with IL2, IL6, IL9, IL12, γIFN (10 ng/ml) IL10, $TGF_\beta$, IL5 (20 ng/ml) IL4 (40 ng/ml) or TNFα (100 u/ml). Resting monocytes were isolated from PBMCs by Percol gradient centrifugation and were >90% $CD14^+$. $CD4^+$, $CD8^+$, $CD19^+$ cells were isolated from PBMCs by positive selection using MACs magnetic beads according to the manufacturer's protocols (Miltenyi Inc). Monocytes were stimulated for 4 hours in RPMI 10% FCS with or without LPS or γIFN. RNA was prepared using RNeasy Mini Kit (Qiagen) as per the manufacturer's instructions and Northern blots were probed using the labeled probe described above.

Human Immune Northern blot analysis revealed 2 transcripts of approximately 2 and 3.5 kb. In lymph node, spleen, thymus and bone marrow the smaller transcript was more abundant and highest T195 expression was seen in lymph node. Additional Northern analysis revealed expression in the following tissues (in decreasing order of expression): lymph node, stomach, small intestine, appendix, lung, spleen, and bone marrow.

Northern blot analysis showed no detectable expression in resting PBMCs. Using 4 hour stimulation of cells with a variety of cytokines, TANGO 195 was shown to be induced by $IFN_\gamma$. A single band of approximately 3–3.5 kb was seen in activated CD8+ cells and in T cells activated with no exogenous cytokines or the combination of IL10 and IL4, but not with $TNF_\alpha$ and $IFN_\gamma$ (after both 8 and 24 hours). The strongest expression was seen in monocytes activated with IFN$_\gamma$ (0.2 or 2 ug/ml) giving 2 bands of approximately 1.5–2 kb and 3–3.5 kb (with the upper band stronger). Purification of monocytes by adhesion to plastic provided sufficient stimulation to induce relatively high expression and all further experiments were carried out using resting monocytes purified by Percol gradient. T195 in purified monocytes was induced by IFN$_\gamma$ but not LPS. Addition of LPS did not increase expression in monocytes or PBMCs and may in fact lead to a slight decrease in expression in IFNγ stimulated monocytes.

TaqMan Analysis

To identify the specific cell types expressing human TANGO 195, expression was measured by TaqMan® quantitative PCR (Perkin Elmer Applied Biosystems). Taqman primers/probe were used within the 3' UTR of T195, and cDNA was prepared from normal human tissues or cell lines as follows:

Individual cell populations (CD3, CD4, CD8, CD14, CD19 and granulocytes) were isolated from whole blood or ficol-hypaque purified PBMCs by positive selection using MACs magnetic beads according to the manufacturer's instructions (Miltenyi Biotec, Auburn, Calif.). PBMCs and T cells were activated with phytohemagglutinin (PHA, 5 μg/ml) for 24 hours; CD14 cells were activated with lipopolysaccharide (LPS, 100 ng/ml) for 24 hours. Cells were cultured in RPMI-1640 medium with 10% FCS (Sigma, MO) supplemented with 2 mM L-glutamine, 0.1 mM non-essential amino acids and 1mM sodium pyruvate (Life Technologies, MD). Human microvascular endothelial cells from the lung (HMVEC) were obtained from Clonetics and stimulated with either IL-1$_\beta$ (100 ng/ml) or TNF-$_\alpha$ (100 ng/ml) for 24 hours. Dendritic cells were derived from peripheral blood derived monocytes or CD34$^+$ cells purified from bone marrow. CD14$^+$ cells were purified from PBMCs and cultured in medium containing GM-CSF (50 ng/ml; R&D Systems, MN) and IL-4 (50 ng/ml; PeproTech, NJ) for 12–14 days. Half of the medium was replaced with fresh medium every three days. Cells were stimulated with TNF-$_\alpha$ (100 ng/ml) for the last 4 days in culture to promote maturation. CD34+ cells were purified from bone marrow (AllCells Inc., CA) by positive selection using magnetic beads and cultured with GM-CSF (100 ng/ml), SCF (120 ng/ml) and TNF-$_\alpha$ (10 ng/ml) for 7 days. CD1a+ cells were sorted and grown for 5–7 more days in GM-CSF and TNF-$_\alpha$.

Total RNA was prepared from purified cells by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. After phenol extraction, cDNA was prepared from the sample using the SUPERSCRIPT™ Choice System following the manufacturer's instructions (GibcoBRL).

T195 expression was measured by TaqMan® quantitative PCR (Perkin Elmer Applied Biosystems). PCR Probes were designed by PrimerExpress software (PE Biosystems). The primers and probes for expression analysis T195 for β-2 microglobulin were as follows:

```
β-2 microglobulin Forward Primer:     (SEQ ID NO:57)
CACCCCCACTGAAAAAGATGA

β-2 microglobulin Probe:              (SEQ ID NO:58)
```

```
-continued
ATGCCTGCCGTGTGAACCACGTG

β-2 microglobulin Reverse Primer:     (SEQ ID NO:59)
CTTAACTATCTTGGGCTGTGACAAAG

T195 Reverse Primer:                  (SEQ ID NO:60)
GCCTAAGGACTTTCAGGTAATCAGAGT T195 probe:                           (SEQ ID NO:61)
CATGGGCCCTCAAAGGTAAATTGCAGT T195 Forward Primer:                  (SEQ ID NO:62)
TGTCAACCATCCTCGGTGTCTA
```

T195 probe was labeled using FAM (6-carboxyfluorescein), and the β-2-microglobulin probe was labeled with VIC. Each reaction contained 200 nM of forward and reverse primers plus 100 nM probe for β-2 microglobulin and 600 nM forward and reverse primers plus 200 nM probe for T195 and reactions were carried out in TaqMan® Universal PCR Master Mix (PE Applied Biosystems) using an ABI PRISM 7700 Sequence Detection System (PE Applied Biosystems). Conditions were as follows: hold for 2 min at 50° C. and 10 min at 95° C., followed by two-step PCR for 40 cycles of 95° C. for 15 see followed by 60° C. for 1 min. $_\Delta$Ct value (expression of T195 relative to β-2 microglobulin) was calculated using the following formula: $_\Delta Ct = Ct_{T195} - Ct_{\beta\text{-}2\ microglobulin}$. The $_{\Delta\Delta}$Ct value (expression of T195 in comparison to a control tissue) for each tissue sample was calculated according to the following formula: $_{\Delta\Delta}Ct = _\Delta Ct_{sample} - Ct_{calibrator}$. Relative expression is then calculated using the arithmetic formula given by $2^{-\Delta\Delta Ct}$.

Significant expression was seen in unpurified PBMCs, monocytes and certain dendritic cells. Relative to the level of expression exhibited in HMVEC cells stimulated with IL-1β, there was an approximately half fold level of TANGO 195 expression seen in CD3$^+$ cells activated with PHA and seen in CD14$^+$ cells stimulated with LPS; an approximately equal level of TANGO 195 expression seen in granulocytes and HMVEC stimulated with TNF-$_\alpha$; an approximately one and one half fold level of TANGO 195 expression seen in PBMCs activated with PHA; an approximately two fold level of TANGO 195 expression seen in PBMCs; an approximately four and a half fold level of TANGO 195 expression seen in CD14$^+$ cells; and an approximately nine and one half fold level of TANGO 195 expression seen in a dendritic cell population.

Example 3

Retroviral Over-expression of T195 in Bone Marrow Reconstituted Irradiated Mice

TANGO 195 function was investigated by reconstituting irradiated mice with bone marrow cells infected with retrovirus expressing full length murine TANGO195 ("T195fl") or the extracellular domain of murine TANGO 195 ("T195ex"). As a control, empty vector was used.

Construction and Production of Retroviruses

The full length (T195fl) and secreted (T195ex) forms of Tango 195 were PCR amplified to introduce unique a 5' XhoI and a 3' EcoRI restriction sites and a Kozak sequence (ACCGCC) in the original cDNAs (Advantage-HF kit, Clontech lab. Inc, Palo Alto. Calif.). The PCR products were ligated into the MSCVNeo EB retroviral vector and clones were sequenced and selected for base perfect match with the original cDNA. Viral supernatants were generated into the 293-EBNA cells (Invitrogen, Carlsbad, Calif.) by co-transfecting 3 constructs; the T195 retroviral construct or control (empty MSCV Neo EB virus), pN8epsilon vector containing the gag/pol genes from the murine moloney leukemia virus (MMLV) and a pN8epsilon vectors containing the Vesicular Stomatitis Virus envelope glycoprotein G (VSV-G) gene. Concentrated viral supernatants were prepared by centrifugation for 2 h at 50,000 g (SW28 rotor 25,000 rpm) at 4° C. Pellets were resuspended in 1.5 ml of DMEM 10% FCS (Stem cell technologies, Vancouver, Canada), shaken at 4° C. for 24 hours, filtered and frozen at −80° C.

Infection Procedure

Donor and recipient mice were C57BL/6 and congenic for CD45 (CD45.1 for donor, CD45.2 for recipient). Bone marrow cells were collected 4 days after 5-fluorouracil (5-FU) treatment, 150 mg/kg administrated intravenously (IV). Lin$^-$ cells were selected using a magnetic cell sorting depletion column (types BS, Miltenyi Biotech, Auburn, Calif.). Briefly, cells were labeled with a mixture of four fluorescein isothiocyanate (FITC)-conjugated antibodies against CD3$_e$, CD11b, CD45R and Ly-6G (Pharmingen, San Diego, Calif.). Cells were washed and incubated with anti-FITC microbeads (Miltenyi Biotech, Auburn, Calif.). Labeled cells were removed using depletion columns as per the manufacturer's instructions. After separation, Lin$^-$ cells were washed and resuspended in DMEM, 10% FCS.

Before infection, Lin$^-$ cells ($10^6$ cells/ml) were pre-stimulated with recombinant mouse interleukin-3 (rmIL3, 10 ng/ml, Endogen, Woburn, Ma.), recombinant mouse interleukin-6 (rmIL6, 10 ng/ml, Endogen, Woburn, Ma.), recombinant mouse stem cell factor (imSCF, 100 ng/ml, R&D System Inc. Mineapolis, Minn.), recombinant mouse fms-like tyrosine kinase-3 ligand (rmFlt-3L, 100 ng/ml, R&D System Inc., Minneapolis, Minn.) and 1% of a conditioned medium containing mouse thrombopoietin (mTPO, $10^4$ U/ml) for 2 days. Cells were centrifuged, resuspended in DMEM 10% FCS and viral supernatant (1/1 vol/vol) in the presence of rmIL3, rmIL6, rmSCF, rmFlt-3L and mTPO and incubated at 37° C., 10% $CO_2$. This infection procedure was repeated after 24 and 4 or 28 hours. The cells were collected and injected into lethally irradiated mice (>2×$10^5$ cells/mouse). Expression of T195 in reconstituted mice was confirmed by dot blot analysis of spleen RNA.

Analysis of Mice

Recipient mice were analyzed approximately 8 and 16 weeks after transplantation for blood chemistry, hematology and tissue histology. Major organs were harvested and tissue fixed in 10% buffered formalin stained with hematoxylin and eosin and subject to histologic analysis. Tissue examined included skin, kidneys, sternum, uterus, thymus, bladder, heart (weighed), ovaries, lungs, skeletal muscle, thyroid/parathyroid, femur, brain (weighed), brown & white fat, pituitary, head, eyes, diaphragm, aorta, spleen (weighed), stomach, intestines, liver (weighed), and adrenals.

Blood was collected from the tail vein or at necropsy by heart puncture. Red blood cells were lysed and FACS was carried out using FITC, PE and CyC directly conjugated antibodies from Pharmingen as per the manufacturer's instructions. Peritoneal lavage was carried out at necropsy by washing the peritoneum with 2×2 ml of PBS. All FACS was gated for viable leukocytes on the basis of forward and side scatter.

Peripheral blood, spleen, lymph node and thymus cells were analyzed by FACS analysis and TANGO 195 RNA levels were analyzed in spleen. The percentage of infected cells, based on the percentage of G418-resistant donor cells, was 54% (T195fl) and 69% (T195ex).

Results

The level of TANGO 195 RNA expression in the spleen of recipient mice, based upon dot blot analysis (GAPDH control), was 10 times that of control mice (328% of GAPDH for T195ex and 332% of GAPDH for T195fl compared to 33% of GAPDH in control mice).

Expression of T195fl had a variety of effects on lymphocytes. In T195fl expressing mice, FACs analysis of peripheral blood using a panel of antibodies (CD3/NK1.1, CD4/CD8, GR1/Mac1, and B220/IgD), in combination with a marker for donor cells (CD45.1), showed an increase in Mac1$^{lo}$ and B220$^+$/IgD$^+$(Mac1$^{lo}$ compared to Mac1$^{hi}$ levels on monocytes). Further analysis by 3 color staining revealed that these were in fact the same population of Mac1$^{lo}$B220$^+$ IgD$^+$ cells and that the increase was statistically significant (p value 0.006). Since peripheral B cells do not usually express Mac1 it seemed most likely that these were B1b cells which are usually found primarily in the peritoneum. FACs analysis of the peritoneal lavage showed that this population was greatly increased (average 21.5% of viable cells in control mice compared to average of 59.5% in T195 mice, std 7.6 and 5.0 respectively, p value 0.0001). Spleen showed a less dramatic but still statistically significant increase (average 9.2% of viable cells in control mice compared to average of 12.6% in T195 mice, std 2.3 and 1.0 respectively, p value 0.04) whereas thymus and bone marrow were similar to control. 3 color analysis showed the cells to be predominantly B220$^+$, Mac1$^+$, CD5$^-$, CD23$^{lo}$, IgD$^+$ cells. Both B220 and IgD expression levels are slightly lower than in B cells of control mice as one would expect for B1b "sister" cells. In addition the total percentage of the peritoneal lavage cells which are B cells, as defined by expression of surface Ig, was increased from 46% (std. 9.7) to 73% (std. 9.7). This phenotype was duplicated in 3 separate experiments with 5 mice per group in each experiment.

The retroviral overexpression in hematopoietic cells of bone marrow reconstituted mice showed an increase in B1 cells in the peripheral blood, spleen, lymph nodes, and peritoneal cavity (an increase from approximately 0–10% in wild type mice to 15–30% in bone marrow reconstituted mice). As these cells do not express CD5, and are CD23$^{lo}$ Mac1$^{lo}$, they appear to be of the B1b subset. These results suggest that increased expression of TANGO 195 on bone marrow derived cells may lead to a decrease in CD4$^+$ T cells in the periphery. TANGO 195 may therefore play a role in B cell maturation and/or modulation of signal through the B cell receptor.

There was also an increase in the percentage of B2 cells (B220$^+$, Cd5$^-$, CD23$^{hi}$) from approximately 15–20% in wild type mice to 40–50% in bone marrow reconstituted mice. Serum titers of bleeds from T195 and control retroviral mice at 7 and 11 weeks post reconstitution showed no differences in total IgM or IgG.

These results suggest that TANGO 195 nucleic acids, proteins, and modulators thereof play a role in B cell leukemia, immune response, and autoimmune disorders (e.g., arthritis).

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule selected from the group consisting of:

a) a nucleic acid molecule comprising a nucleotide sequence which is at least 95% identical to the nucleotide sequence of SEQ ID NO:4 or SEQ ID NO:6 over the whole length of SEQ ID NO: 4 or SEQ ID NO:6, respectively; and b) a nucleic acid molecule which encodes a polypeptide comprising an amino acid sequence which is at least 95% identical to the amino acid sequence of SEQ ID NO:5 over the whole length of SEQ ID NO:5,
wherein the isolated nucleic acid molecule encodes a polypeptide which increases the maturation and/or proliferation of B cells.

2. The isolated nucleic acid molecule of claim 1, which is selected from the group consisting of:
   a) a nucleic acid comprising the nucleotide sequence of SEQ ID NO:4 or SEQ ID NO:6; and
   b) a nucleic acid molecule which encodes a polypeptide comprising the amino acid sequence of SEQ ID NO:5.

3. The nucleic acid molecule of claim 1 further comprising a vector nucleic acid sequence.

4. The nucleic acid molecule of claim 1 further comprising a nucleic acid sequence encoding a heterologous polypeptide.

5. An isolated host cell which contains the nucleic acid molecule of claim 1.

6. The isolated host cell of claim 5 which is a mammalian host cell.

7. An isolated non-human mammalian host cell containing the nucleic acid molecule of claim 1.

8. A method for producing a polypeptide comprising culturing the isolated host cell of claim 5 under conditions in which the nucleic acid molecule is expressed.

9. An isolated nucleic acid molecule comprising a nucleotide sequence that is the complement of the isolated nucleic acid molecule of claim 1.

10. A method for detecting the presence of a nucleic acid molecule of claim 1 in a sample, comprising the steps of:
    a) contacting the sample with a nucleic acid probe or primer which selectively hybridizes to said nucleic acid molecule of claim 1 under conditions of 6×SSC at 45° C., followed by one or more washes in 0.2×SSC, 0.1% SDS at 50° C.; and
    b) determining whether the nucleic acid probe or primer hybridizes to a nucleic acid molecule in the sample.

11. The method of claim 10, wherein the sample comprises mRNA molecules and is contacted with said nucleic acid probe or primer.

12. A kit comprising the nucleic acid molecule of claim 1 or the complement thereof and instructions for use.

13. An isolated nucleic acid molecule which encodes a polypeptide comprising amino acids 23–312 of SEQ ID NO:5.

* * * * *